US008026226B2

(12) United States Patent
Addis et al.

(10) Patent No.: US 8,026,226 B2
(45) Date of Patent: Sep. 27, 2011

(54) MEDICAL AND NUTRITIONAL APPLICATIONS OF HIGHLY REFINED CELLULOSE

(75) Inventors: Paul Bradley Addis, St. Paul, MN (US);
Rongsheng Roger Ruan, Arden Hills, MN (US); Joseph M. Keenan, Edina, MN (US); Daniela Geleva, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 2077 days.

(21) Appl. No.: 10/270,475

(22) Filed: Oct. 11, 2002

(65) Prior Publication Data

US 2003/0144245 A1 Jul. 31, 2003

Related U.S. Application Data

(60) Provisional application No. 60/329,255, filed on Oct. 12, 2001.

(51) Int. Cl.
*A61K 31/715* (2006.01)
(52) U.S. Cl. .......................................... 514/57; 514/866
(58) Field of Classification Search .................... 514/57, 514/866
See application file for complete search history.

(56) References Cited

U.S. PATENT DOCUMENTS

| | | | |
|---|---|---|---|
| 2,487,114 A | 11/1949 | Dreyfus | |
| 3,539,365 A | 11/1970 | Durand et al. | |
| 3,653,925 A | 4/1972 | Anker et al. | |
| 3,660,183 A | 5/1972 | Knowles et al. | |
| 3,664,844 A | 5/1972 | Miller | |
| 4,226,982 A | 10/1980 | Blount | |
| 4,259,147 A | 3/1981 | Gordy | |
| 4,294,653 A | 10/1981 | Lindahl et al. | |
| 4,307,121 A | 12/1981 | Thompson | |
| 4,341,807 A | 7/1982 | Turbak et al. | |
| 4,374,702 A * | 2/1983 | Turbak et al. ................. 162/100 |
| 4,378,381 A | 3/1983 | Turbak et al. | |
| 4,452,721 A | 6/1984 | Turbak et al. | |
| 4,486,459 A | 12/1984 | Thompson | |
| 4,543,370 A | 9/1985 | Porter et al. | |
| 4,649,113 A | 3/1987 | Gould | |
| 4,652,324 A | 3/1987 | Yamashina et al. | |
| 4,661,359 A | 4/1987 | Seaborne et al. | |
| 4,774,098 A | 9/1988 | Gould et al. | |
| 4,806,203 A | 2/1989 | Elton | |
| 4,806,475 A | 2/1989 | Gould | |
| 4,810,534 A | 3/1989 | Seaborne et al. | |
| 4,915,971 A | 4/1990 | Fennema et al. | |
| 4,957,599 A | 9/1990 | Chou et al. | |
| 4,960,763 A | 10/1990 | Stephens et al. | |
| 4,997,488 A | 3/1991 | Gould et al. | |
| 5,017,319 A | 5/1991 | Shen | |
| 5,023,097 A | 6/1991 | Tyson | |
| 5,023,103 A | 6/1991 | Ramaswamy | |
| 5,057,334 A | 10/1991 | Vail | |
| 5,069,919 A | 12/1991 | Weibel | |
| 5,089,307 A | 2/1992 | Ninomiya et al. | |
| 5,123,962 A | 6/1992 | Komuro et al. | |
| 5,126,152 A | 6/1992 | Feeney et al. | |
| 5,147,670 A | 9/1992 | Cebula et al. | |
| 5,385,640 A | 1/1995 | Weibel et al. | |
| 5,393,333 A | 2/1995 | Trouve | |
| 5,415,804 A | 5/1995 | Minami et al. | |
| 5,503,996 A | 4/1996 | Torget et al. | |
| 5,529,663 A | 6/1996 | Springer | |
| 5,585,366 A | 12/1996 | Gallaher et al. | |
| 5,626,810 A | 5/1997 | Zikeli et al. | |
| 5,643,359 A | 7/1997 | Soroushian et al. | |
| 5,721,221 A | 2/1998 | Gallaher et al. | |
| 5,766,662 A | 6/1998 | Inglett | |
| 5,769,934 A | 6/1998 | Ha et al. | |
| 5,817,381 A | 10/1998 | Chen et al. | |
| 6,083,582 A * | 7/2000 | Chen et al. ................... 428/34.8 |
| 6,248,390 B1 * | 6/2001 | Stillman ....................... 426/590 |
| 6,273,994 B1 | 8/2001 | Creber et al. | |
| 6,506,435 B1 | 1/2003 | Lundberg et al. | |
| 2004/0086626 A1 | 5/2004 | Lundberg et al. | |

FOREIGN PATENT DOCUMENTS

| | | |
|---|---|---|
| BR | 9005762 A | 6/1992 |
| EP | 0337653 A3 | 10/1989 |
| JP | 09071677 A | 3/1997 |
| JP | 09195194 A | 7/1997 |
| WO | WO 00/05310 | 2/2000 |
| WO | WO 01/32978 A1 | 5/2001 |
| WO | WO 03/030916 A1 | 4/2003 |

OTHER PUBLICATIONS

Behall, K. M. Effect of soluble fibers on plasma lipids, glucose tolerance and mineral balance. Advances in Experimental Medicine and Biology (1990), 270(New Dev. Diet. Fiber), 7-16.*
Ang et al. "Multiple Functions of Powdered Cellulose as a Food Ingredient," *Cereal Foods World*, 1991;36(7):558-564.
"Commercially-viable edible coatings face several challenges," *Emerging Food R&D Report*, 1994;1 pg.
"Consider edible collagen film for packaging," *Emerging Food R&D Report*, 1995;1 pg.
"Executives . . . FYI," *Emerging Food R&D Report*, 1995;1 pg.
Fast, "Chapter 2: Manufacturing Technology of Ready-to-Eat Cereals," *Breakfast Cereals and How They are Made*, Fast et al., eds., American Association of Cereal Chemists, Inc., St. Paul, MN 1990;15-42.
Gennadios et al., "Edible Films and Coatings from Wheat and Corn Proteins," *Food Tech.*, 1990;63-69.
Goddard, "Now you can have your pack and eat it," *Packaging Week*, 1994;10(22):28-29.

(Continued)

*Primary Examiner* — Kevin E Weddington
(74) *Attorney, Agent, or Firm* — Mueting Raasch & Gebhardt, P.A.

(57) ABSTRACT

The present invention provides a method for using processed cellulose. Preferably, the processed cellulose is a highly refined cellulose (HRC). The HRC is useful in a number of medical and nutritional applications. These medical and nutritional applications can include, but are not limited to, administering effective amounts of the HRC for lowering values of risk factor measurements for such diseases as arteriosclerotic cardiovascular disease and diabetes. Treatment of other diseases and conditions with the HRC is also possible.

28 Claims, 14 Drawing Sheets

OTHER PUBLICATIONS

Keenan, "Solublized Cellulose Trial," Grant Abstract, Grant No. 2M01RR000400-320483. National Institutes of Health General Clinical Research, National Center for Research Resources, Dec. 1, 1978 to Nov. 30, 2004 [retrieved on Dec. 19, 2003]. Retrieved from the Internet:<URL:crisp.cit.nih.gov/crisp/CRISP_LIB. getdoc?textkey=6409139&p_ grant_num=2M01RR000400-320483&p_query=&ticket...>; 2 pgs.

Kester et al., "Edible films and coatings: a review," *Food Tech.*, 1986;47-59.

Krauss et al., "Intermediate-density lipoproteins and progression of coronary artery disease in hypercholesteralaemic men," *The Lancet*, 1987; 2:62-66.

Krochta et al., "Edible Coatings and Films to Improve Food Quality," *Food Trade Review*, 1994;61(11):753-754.

Long, "Ingredients and Coatings," *Frozen and Chilled Foods*, 1994;48(2):14.

Park et al., "Permeability and Mechanical Properties of Cellulose-Based Edible Films," *Journal of Food Science*, 1993;58(6):1361-1364.

"Precut Produce Sales to Soar—Edible Coating has Wide Application," *Food Institute Report*, Nov. 20, 1995;68:3.

Ruan et al., "Structure-Function Relationships of Highly Refined Cellulose Made from Agricultural Fibrous Residues," *Applied Engineering in Agriculture*, 1996;12(4):465-468.

Turbak et al., "Microfibrillated cellulose, a new cellulose product: properties, uses, and commercial potential," *Journal of Applied Polymer Science: Applied Polymer Symposium*, 1983;37:815-827.

Anderson, "Dietary fibre, complex carbohydrate and coronary artery disease," *Can. J. Cardiol.*, 1995; 11(suppl. G):55G-62G.

Anderson et al., "High Density Lipoprotein Distribution; Resolution and Determination of Three Major Components in a Normal Population Sample," *Atherosclerosis*, 1978; 29:161-179.

Anderson et al., "Impact of Nondigestible Carbohydrates on Serum Lipoproteins and Risk for Cardiovascular Disease," *J. Nutr.*, 1999; 129(7S):1457S-1466S.

Appel et al., "A Clinical Trial of the Effects of Dietary Patterns on Blood Pressure," *N. Engl. J. Med.*, 1997; 336(16):1117-1124.

Ascherio et al., "A Prospective Study of Nutritional Factors and Hypertension Among US Men," *Circulation*, 1992; 86(5):1475-1484.

Austin et al., "Low-Density Lipoprotein Subclass Patterns and Risk of Myocardial Infarction," *JAMA*, 1988: 260(13):1917-1921.

Austin et al., "Epidemiology of Triglycerides, Small Dense Low-Density Lipoprotein, and Lipoprotein(a) as Risk Factors for Coronary Heart isease," *Med. Clin. N. Am.*, 1994; 78(1):99-115.

Bergman, "ToWard Physiological Understanding of Glucose Tolerance: Minimal-Model Approach," *Diabetes*, 1989; 38:1512-1527.

Bergman et al., "Quantitative estimation of insulin sensitivity," *Am. J. Physiol.*, 1979; 236(6):E667-E677.

Bergman et al., "Physiologic Evaluation of Factors Controlling Glucose Tolerance in Man: Measurement of Insulin Sensitivity and β-Cell Glucose Sensitivity from the Response to Intravenous Glucose," *J. Clin. Invest.*, 1981; 68:1456-1467.

Bergman et al., "Assessment of Insulin Sensitivity in Vivo," *Endocr. Rev.*, 1985; 6(1):45-86.

Bourdon et al., "Postprandial lipid, glucose, insulin, and cholecystokinin responses in men fed barley pasta. enriched with β-gulcan," *Am. J. Clin. Nutr.*, 1999; 69:55-63.

Brown et al., "Regression of Coronary Artery Disease as a Result of Intensive Lipid-Lowering Therapy in Men with High Levels of Apolipoprotein B," *N. Engl. J. Med.*, 1990; 323(19):1289-1298.

Brown et al., "Cholesterol-lowering effects of dietary fiber: a meta-analysis," *Am. J. Clin. Nutr.*, 1999; 69:30-42.

Buchwald et al., "Effect of Partial Beal Bypass Surgery on Mortality and Morbidity from Coronary Heart Disease in Patients with Hypercholesterolemia: Report of the Program on the Surgical Control of the Hyperlipidemias (POSCH)," *N. Engl. J. Med.*, 1990; 323(14):946-955.

Campos et al., "Predominance of Large LDL and Reduced $HDL_2$ Cholesterol in Normolipidemic Men with Coronary Artery Disease," *Arterioscler. Thromb. Vasc. Biol.*, 1995;15(8):1043-1048.

Carleton et al., "Report of the Expert Panel on Population Strategies for Blood Cholesterol Reduction: A Statement from the National Cholesterol Education Program, National Heart, Lung, and Blood Institute, National Institutes of Health," *Circulation*, 1991; 83(6):2154-2232.

Castelli et al., "Incidence of Coronary Heart Disease and Lipoprotein Cholesterol Levels: The Framingham study," *JAMA*, 1986; 256(20):2835-2838.

Castelli, "Cardiovascular Disease in Women," *Am. J. Obstet. Gynecol.*, 1988; 158(6):1553-1560.

Cavallo-Perin et al., "Myocardial Infarction Before the Age of 40 Years is Associated with Insulin Resistance," *Metabolism*, 2001; 50(1):30-35.

Charles et al., "Risk factors for NIDDM in White Population: Paris Prospective Study," *Diabetes*, 1991; 40(7):796-799.

Collins et al., "Blood pressure, stroke, and coronary heart disease. Part 2, short-term reductions in blood pressure: overview of randomised drug trials in their epidemiological context," *Lancet*, 1990; 335:827-838.

Davidson et al., "The Hypocholesterolemic Effects of B-glucan in Oatmeal and Oat Bran: a Dose-controlled Study," *JAMA*, 1991; 265(14):1833-1839.

Després et al., "Hyperinsulinemia as an Independent Risk Factor for Ischemic Heart Disease," *N. Engl. J. Med.*, 1996; 334(15):952-957.

Ducimentiere et al., "Relationship of Plasma Insulin Levels to the Incidence of Myocardial Infarction and Coronary Heart Disease Mortality in a Middle-aged Population," *Diabetologia*, 1980;19:205-210.

Eliasson et al., "A dietary fibre supplement in the treatment of mild hypertension. A randomized, double-blind, placebo-controlled trial," *J. Hypertens.*, 1992; 10(2):195-199.

The Expert Committee on the Diagnosis and Classification of Diabetes Mellitus, "Report of the Expert Committee on the Diagnosis and Classification of Diabetes Mellitus," *Diab. Care*, 1997; 20:1183-1197.

The Expert Panel, "Report of the National Cholesterol Education Program Expert Panel on Detection, Evaluation, and Treatment of High Blood Cholesterol in Adults," *Arch. Int. Med.*, 1988;148:36-69.

Expert Panel on Detection, Evaluation, and Treatment of High Blood Cholesterol in Adults, Executive Summary of the Third Report of the National Cholesterol Education Program (NCEP) Expert Panel on Detection, Evaluation, and Treatment of High Blood Cholesterol in Adults (Adult Treatment Panel III), *JAMA*, 2001; 285(19):2486-2497.

Falk et al., "On the Relation between Turgor Pressure and Tissue Ridigity. I Experiments on Resonance Frequency and Tissue Rigidity," *Physiol. Plantarum*, 1958,11:802-837.

Feillet et al., "Evidence for a Short-term Stimulatory Effect of Insulin on Cholesterol Synthesis in Newly Insulin-treated Diabetic Patients," *Metabolism*, 1994; 43(10):1233-1240.

Ferrannini et al., "Insulin Resistance in Essential Hypertension," *N. Engl. J. Med.*, 1987; 317(6):350-357.

Flack et al., "Blood Pressure and Mortality among Men with Prior Myocardial Infarction,"*Circulation*, 1995; 92(9):2437-2445.

Frey-Wyssling, "Chapter III; Deformation of Plant Cell Walls," *Deformation and Flow in Biological Systems*, Amsterdam, 1952:195-254.

Frick et al., "Helsinki Heart Study: Primary-Prevention Trial with Gemfibrozil in Middle-aged Men with Dyslipidemia," *N. Engl. J. Med.*, 1987; 317(20):1237-1245.

Fried et al., "Physiological role of cholecystokinin on postprandial insulin secretion and gastric meal emptying in man. Studies with the cholecystokinin receptor antagonist loxiglumide," *Diabetologia*, 1991; 34:721-726.

Friedewald et al., "Estimation of the Concentration of Low-density Lipoprotein Cholesterol in Plasma, Without Use of the Preparative Ultracentrifuge," *Clin. Chem.*, 1972; 18(6):499-502.

Fuller et al., "Mortality from coronary heart disease and stroke in relation to degree of glycaemia: the Whitehall study," *Br. Med. J.*, 1983; 287:867-870.

Geleva, "Effects of Solubilized Cellulose (a Viscous Dietary Fiber) on Serum Lipid Concentrations, Blood Pressure, Glucose Tolerance, Insulin Metabolism and Plasma Cholecystokinin," Ph.D. thesis, University of Minnesota, 2001.

Geleva et al., "Acute and chronic effects of a solubilized cellulose fiber on fasting and postprandial glucose and cholecystokinin concentrations in hypercholesterolemic men and women," *FASEB Journal*, 2002; Abstract from Experimental Biology 2002, New Orleans, Louisiana: A656.

Geleva et al., "The Effects of a Novel Solubilized Cellulose Supplement on Serum Cholesterol and Blood Pressure," *Journal of the American College of Nutrition*, Abstract, 2000; 19(5):699.

Genest et al., "Prevalence of Lipoprotein (a) [Lp(a)] Excess in Coronary Artery Disease," *Am. J. Cardiol.*, 1991; 67(13):1039-1045.

Genest et al., "Lipoprotein Cholesterol, Apolipoprotein A-I and B and Lipoprotein (a) Abnormalities in Men with Premature Coronary Artery Disease," *J. Am. Coll. Cardiol.*, 1992; 19(4):792-802.

Glore et al., "Soluble fiber and serum lipids: A literature review," *J. Am. Diet. Assoc.*, 1994; 94(4):425-436.

Gordon et al., "High Density Lipoprotein as a Protective Factor Against Coronary Heart Disease: The Framingham Study," *Am. J. Med.*, 1977; 62:707-714.

Gordon et al., "High-Density Lipoprotein Cholesterol and Cardiovascular Disease: Four Prospective American Studies," *Circulation*, 1989; 79(1):8-15.

Grundy et al., "Two Different Views of the Relationship of Hypertriglyceridemia to Coronary Heart Disease: Implications for Treatment," *Arch. Intern. Med.*, 1992;152:28-34.

Gu, *Structure-Function Relationships of Highly Refined Cellulose*, M.S. thesis, University of Minnesota, May 2000.

Gu et al., "Structure-Function Relationships of Highly Refined Cellulose," *Transactions of the ASAE*, 2001; 44(6):1707-1712.

Haffner, "Prospective Analysis of the Insulin-resistance Syndrome (Syndrome X)," *Diabetes*, 1992; 41:715-722.

Haffner, "Epidemiology of Insulin Resistance and its Relation to Coronary Artery Disease," *Am. J. Cardiol.*, 1999; 84:11J-14J.

Hasegawa et al., "Oral Glucose Ingestion Stimulates Cholecystokinin Release in Normal Subjects and Patients with Non-Insulin-Dependent Diabetes Mellitus," *Metabolism*, 1996; 45(2):196-202.

Hearn et al., "Predictive Value of Lipoprotein (A) and Other Serum Lipoproteins in the Angiographic Diagnosis of Coronary Artery Disease," *Am. J. Cardiol.*, 1990; 66:1176-1180.

Hermansen, "Effects of Cholecystokinin (Cck)-4, Nonsulfated CCK-8, and Sulfated CCK-8 on Pancreatic Somatostatin, Insulin, and Glucagon Secretion in the Dog: Studied in Vitro," *Endrocrinology*, 1984; 114:1770-1775.

Holme, "An Analysis of Randomized Trials Evaluating the Effect of Cholesterol Reduction on Total Mortality and Coronary Heart Disease Incidence," *Circulation*, 1990; 82(6):1916-1924.

Holme, "Effects of lipid-lowering therapy on total and coronary mortality," *Curr. Opin. Lipid*, 1995; 6(6):374-378.

Holt et al., "Relationship of Satiety to Postprandial Glycaemic, Insulin and Cholecystokinin Responses," *Appetite*, 1992; 18:129-141.

Kahn et al., "Quantification of the Relationship Between Insulin Sensitivity and β-Cell Function in Human Subjects: Evidence for a Hyperbolic Function," *Diabetes*, 1993; 42:1663-1672.

Kannel et al., "Serum Cholesterol, Lipoproteins and the Risk of Coronary Heart Disease: The Framingham Study," *Ann. Intern. Med.*, 1971; 74(1):1-12.

Kannel et al., "Atherosclerosis Risk Factors," *Pharmac. Ther.*, 1987; 32:207-235.

Katsanidis et al., "Solubilized Cellulose and Dehydrated Potato Extract in Cooked, Low-fat Comminuted Beef," *J. Food Sci.*, 2001; 66(5):758-761.

Keenan et al., "Soluble Fiber and Hypertension," *Dietary Fiber in Health and Disease*, New York, 1997:79-87.

Keys et al., "Serum Cholesterol Response to Changes in the Diet. IV. Particular Saturated Fatty Acids in the Diet," *Metabolism*, 1965;14(7):776-787.

Kottke et al., "Apolipoproteins and Coronary Artery Disease," *Mayo Clin. Proc.*, 1986; 61:313-320.

Kramarow et al., Health and Aging Chartbook, Health, United States, Hyattsville, MD: National Center for Health Statistics, 1999:8-9.

Lamarche et al., "Fasting Insulin and Apolipoprotein B Levels and Low-Density Lipoprotein Particle Size as Risk Factors for Ischemic Heart Disease," *JAMA*, 1998; 279(24):1955-1961.

La Rosa et al., The Cholesterol Facts: A Summary of the Evidence Relating Dietary Fats, Serum Cholesterol, and Coronary Heart Disease. A Joint Statement by the American Heart Association and the National Heart, Lung, and Blood Institute, *Circulation*, 1990; 81(5):1721-1733.

Lerner et al., "Relationships Between Intravenous Glucose Loads, Insulin Responses and Glucose Disappearance Rate," *J. Clin. Endocrinol. Metab.*, 1971; 33:409-417.

Lichtenstein et al., "Systolic and diastolic blood pressures as predictors of coronary heart disease mortality in the Whitehall study," *Br. Med. J.*, 1985; 291:243-245.

Liddle et al., "Regulation of Gastric Emptying in Humans by Cholecystokinin," *J. Clin. Invest.*, 1986; 77(3):992-996.

Liddle et al., "Physiological Role for Cholecystokinin in Reducing Postprandial Hyperglycemia in Humans," *J. Clin. Invest.*, 1988. 81:1675-1681.

Lillioja et al., "Insulin Resistance and Insulin Secretory Dysfunction as Precursors of Non-Insulin-Dependent Diabetes Mellitus: Prospective Studies of Pima Indians,"*N. Engl. J. Med.*, 1993; 329(27):1988-1992.

Lipid Research Clinics Program, "The Lipid Research Clinics Coronary Primary Prevention Trial Results. I. Reduction in Incidence of Coronary Heart Disease," *JAMA*, 1984; 251(3):351-364.

Lipid Research Clinics Program, "The Lipid Research Clinics Coronary Primary Prevention Trial Results. II. The Relationship of Reduction in Incidence of Coronary Heart Disease to Cholesterol Lowering," *JAMA*, 1984; 251(3):365-374.

Ludwig et al., "Dietary Fiber, Weight Gain, and Cardiovascular Disease Risk Factors in Young Adults," *JAMA*, 1999; 282(16):1539-1546.

Lundberg, *Development of a New Process to Make Highly Refined Cellulose*, M.S. thesis, University of Minnesota, Jan. 2000.

Maciejko et al., Apolipoprotein A-I as a Marker of Angiographically Assessed Coronary-Artery Disease, *N. Engl. J. Med.*, 1983; 309(7):385-389.

MacMahon et al., "Blood pressure, stroke, and coronary heart disease. Part 1, prolonged differences in blood pressure: prospective observational studies corrected for the regression dilution bias," *Lancet*, 1990; 335:765-774.

Manninen et al.,"Lipid Alterations and Decline in the Incidence of Coronary Heart Disease in the Helsinki Heart Study," *JAMA*, 1988; 260(5):641-651.

Manninen et al., "Joint Effects of Serum Triglyceride and LDL Cholesterol and HDL Cholesterol Concentrations on Coronary Heart Disease Risk in the Helsinki Heart Study," *Circulation*, 1992; 85(1):37-45.

Matthews et al., "Analysis of serial measurements in medical research," *Br. Med. J.*, 1990; 300:230-235.

McLaughlin et al., "Fatty Acid Chain Length Determines Cholecystokinin Secretion and Effect on Human Gastric Motility," *Gastroenterology*, 1999; 116:46-53.

Miller et al., "Plasma-High-Density-Lipoprotein Concentration and Development of Ischaemic Heart Disease," *Lancet*, 1975; 1:16-19.

Miller et al., "Relation of angiographically defined coronary artery disease to plasma lipoprotein subfractions and apolipoproteins," *Br. Med. J.*, 1981; 282:1741-1744.

Naito, "Serum Apolipoprotein Measurements: An Improved Discriminator for Assessing Coronary Heart Disease Risk," *Comp. Ther.*, 1987; 13(11):43-52.

National Cholesterol Education Program, "Second Report of the Expert Panel on Detection, Evaluation, and Treatment of High Blood Cholesterol in Adults (Adult Treatment Panel II)," National Institutes of Health, National Heart, Lung, and Blood Institute, NIH Publication No. 93/3096; 1993:4-28.

NIH Consensus Conference, "Triglyceride, High-Density Lipoprotein, and Coronary Heart Disease; NIH Consensus Development Panel on Triglyceride, High-Density Lipoprotein, and Coronary Heart Disease," *JAMA*, 1993; 269(4):505-510.

Neaton et al., "Serum Cholesterol Level and Mortality Findings for Men Screened in the Multiple Risk Factor Intervention Trial," *Arch. Intern. Med.*, 1992; 152(7):1490-1500.

Newman et al., "Relation of Serum Lipoprotein Levels and Systolic Blood Pressure to Early Atherosclerosis: The Bogalusa Heart Study," *N. Engl. J. Med.*, 1986; 314(3):138-144.

Pacini et al., "Computer Modelling for Quantitative Assessment of Metabolic States," *Proceedings AAMSI Congress 83*, 1983:170-174.

Pacini et al., "MINMOD: A computer program to calculate insulin sensitivity and pancreatic responsivity from the frequently sampled intravenous glucose tolerance test," *Comput. Methods Programs Biomed.*, 1986; 23:113-122.

Parrott et al., "Functional Properties of Various Fibers: Physical Properties," *J. Food Sci.*, 1978; 43:759-763.

Pocock et al., "Concentrations of high-density lipoprotein cholesterol, triglycerides, and total cholesterol in ischaemic heart disease," *Br. Med. J.*, 1989; 298:998-1002.

Pyöräläet al., "Plasma Insulin as Coronary Heart Disease Risk Factor: Relationship to Other Risk Factors and Predictive Value During 9½Year Follow-Up of the Helsinki Policemen Study Population," *Acta Med. Scand. (Suppl. 701)*, 1985:38-52.

Raybould et al., "Integration of Postprandial Function in the Proximal Gastrointestinal Tract: Role of CCK and Sensory Pathways,"*Ann. Ny Acad. Sci.*, 1994; 713:143-156.

Reaven, "Role of Insulin Resistance in Human Disease," *Diabetes*, 1988; 37:1595-1607.

Reiser et al., "Effect of the Type of Dietary Carbohydrate on Small Intestinal Functions," *Prog. Biochem. Pharmacol.*, 1986; 21:135-159.

Ripsin et al., "Oat Products and Lipid Lowering: A Meta-analysis," *JAMA*, 1992; 267(24):3317-3325.

Rossouw et al., "The Value of Lowering Cholesterol after Myocardial Infarction," *N. Engl. J. Med.*, 1990; 323(16):1112-1119.

Ruan et al., "Structure-Function Relationships of Highly Refined Cellulose Made from Agricultural Fibrous Residues," *Appl. Engineer. Agric.*, 1996; 12(4):465-468.

Rushakoff et al., "Physiological Concentrations of Cholecystokinin Stimulate Amino Acid-Induced Insulin Release in Humans," *J. Clin. Endocrinol. Metab.*, 1987; 65(3):395-401.

Saad et al., "A Comparison Between the Minimal Model and the Glucose Clamp in the Assesment of Insulin Sensitivity Across the Spectrum of Glucose Tolerance," *Diabetes*, 1994; 43:1114-1121.

Sacks et al., "Effects on Blood Pressure of Reduced Dietary Sodium and the Dietary Approaches to Stop Hypertension (DASH) Diet, " *N. Engl. J. Med.*, 2001; 344(1):3-10.

Saltzman et al., "An Oat-Containing Hypocaloric Diet Reduces Systolic Blood Pressure and Improves Lipid Profile Beyond Effects of Weight Loss in Men and Women," *J. Nutr.*, 2001; 131(5):1465-1470.

Sato et al., "Experimental Atherosclerosis-Like Lesions Induced by Hyperinsulinism in Wistar Rat," *Diabetes*, 1989; 38:91-96.

Scandinavian Simvastatin Survival Study Group, "Randomised trial of cholesterol lowering in 4444 patients with coronary heart disease: the Scandinavian Simvastatin Survival Study (4S)" *Lancet*, 1994; 344:1383-1389.

Schlamowitz et al., "Treatment of Mild to Moderate Hypertension with Dietary Fibre," *Lancet*, 1987; 2:622-623.

Schneeman, "Dietary Fiber: Physical and Chemical Properties, Methods of Analysis, and Physiological Effects," *Food Technol.*, 1986; 40(2):104-110.

Scoppola et al., "Effects of Insulin on Cholesterol Synthesis in Type Ii Diabetes Patients," *Diabetes Care*; 1995; 18(10):1362-1369.

Sempos et al., "Prevalence of High Blood Cholesterol Among US Adults: An Update Based on Guidelines from the Second Report of the National Cholesterol Education Program Adult Treatment Panel," *JAMA*, 1993; 269(23):3009-3014.

Shepherd et al., "Prevention of Coronary Heart Disease with Pravastatin in Men with Hypercholesterolemia," *N. Engl. J. Med.*, 1995; 333(20):1301-1307.

Singh et al., "Can guafa fruit intake decrease blood pressure and blood lipids?" *J. Hum. Hypertens.*, 1993; 7:33-38.

The Sixth Report of the Joint National Committee on Prevention, Detection, Evaluation, and Treatment of High Blood Pressure, *Arch. Intern. Med.*, 1997; 157(20:2413-2445.

Slavin, "Dietary fiber: Classification, chemical analyses, and food sources," *JADA*, 1987; 87(9):1164-1171.

Slavin, "Dietary Fiber," *Contemporary Nutrition Support Practice; A Clinical Guide*; 1998:174-182.

Smith, "Carbohydrates, fat, and insulin action," *Am. J. Clin. Nutr.*, 1994; 59 (*suppl*):686S-689S.

Stamler et al., "Effect of Insulin in the Induction and Regression of Atherosclerosis in the Chick," *Circ. Res.*, 1960; 8:572-576.

Stout, "Development of Vascular Lesions in Insulin-treated Animals Fed a Normal Diet," *Br., Med. J.*, 1970; 3:685-687.

Stout, "The Effect of Insulin and Glucose on Sterol Synthesis in Cultured Rat Arterial Smooth Muscle Cells," *Atherosclerosis*, 1977; 27:271-278.

Stout et al., "Insulin and Atheroma," *Lancet*, 1969;1:1078-1080.

Superko et al., "Coronary Artery Disease Regression: Convincing Evidence for the Benefit of Aggressive Lipoprotein Management," *Circulation*, 1994; 90(2):1056-1069.

Swislocki et al., "Insulin Resistance, Glucose Intolerance and Hyperinsulinemia in Patients with Hypertension," *Am J. Hypertens.*, 1989; 2(2):419-423.

Truswell et al., "Dietary Fibre and Plasma Lipids: Potential for Prevention and Treatment of Hyperlipidaemias," *Dietary Fibre—A Component of Food*, New York; 1992:295-332.

VanHorn et al., "Serum lipid response to oat product intake with a fat-modified diet," *J. Am. Diet Assoc.*, 1986; 86(6):759-764.

VanHorn et al., "Serum Lipid Response to a Fat-modified, Oatmeal-enhanced Diet," *Prev. Med.*, 1988; 17:377-386.

Verspohl et al., "Evidence that Cholecystokinin Interacts with Specific Receptors and Regulates Insulin Release in Isolated Rat Islets of Langerhans," *Diabetes*, 1986; 35:38-43.

Williams, "Cholecystokinin: A Hormone and a Neurotransmitter," *Biomed. Res.*, 1982; 3(2):107-121.

Wilson et al., "High Density Lipoprotein Cholesterol and Mortality: The Framingham Heart Study," *Arteriosclerosis*, 1988; 8(6):737-741.

Wilson et al., "The Impact of Triglycerides on Coronary Heart Disease: The Framingham Study," *Atheroscler. Rev.*, 1991; 22:59-63.

World Health Organization European Collaborative Group, "Multifactorial trial in the prevention of coronary heart disease: 3. Incidence and mortality results," *Eur. Heart J.*, 1983; 4:141-147.

Wright et al., "Dietary fibre and blood pressure," *Br. Med., J.*, 1979; 2:1541-1543.

Yang et al.,"Modified protocols improve insulin sensitivity estimation using the minimal model," *Am. J. Physiol.*, 1987; 253(6):E595-E602.

Yi, *Preparation and Properties of a New Food Hydrocolloidal Material, Refined Cellulose (RC), Made from Corn Cobs and Husks*, M.S. thesis, University of Minnesota, May 1997.

Zavaroni et al., "Prevalence of hyperinsulinaemia in patients with high blood pressure," *J. Int. Med.*, 1992; 231:235-240.

\* cited by examiner

MEDICAL AND NUTRITIONAL APPLICATIONS OF HIGHLY REFINED CELLULOSE

This application claims the benefit of U.S. Provisional Application Ser. No. 60/329,255, filed 12 Oct. 2001, which is incorporated herein by reference in its entirety.

GOVERNMENT FUNDING

This invention was made with government support under a grant from the National Institutes of Health General Clinical Research Center grant no. M01-RR00400 from the National Center for Research Resources. The U.S. Government may have certain rights in this invention.

FIELD OF THE INVENTION

The invention relates generally to the use of cellulose, and more specifically to the use of processed cellulose for medical and nutritional applications.

BACKGROUND

Cardiovascular disease (CVD) continues to be the leading cause of death in the United States and is associated with a growing economic and personal burden (1999 Heart and Stroke Statistical Update, Dallas, Tex.: American Heart Association, 1998). Despite numerous advances in modern medical treatments, the most effective strategy for combating the disease remains prevention. Research efforts since the 1960s have identified elevated total serum cholesterol and low-density lipoprotein-cholesterol (LDL-cholesterol) concentrations as powerful risk factors for CVD (Pocock and Shaper, Br. Med. J., 298, 998 (1989); National Cholesterol Education Program, Second Report of the Expert Panel on Detection, Evaluation, and Treatment of High Blood Cholesterol in Adults (Adult Treatment Panel II), Bethesda: National Institutes of Health, National Heart, Lung, and Blood Institute, National Cholesterol Education Program, 1993).

Additionally, observational studies and randomized trials have demonstrated a positive and continuous relationship between diastolic blood pressure (DBP) and CVD (MacMahon et al., Lancet, 335, 765 (1990); Collins et al., Lancet, 335, 827 (1990)). The age-adjusted prevalence of hypertension (systolic blood pressure (SBP)>140 millimeters mercury (mm Hg), or diastolic blood pressure>90 mm Hg, or use of hypertensive medication) among U.S. adults 20-74 years of age has been estimated to be 23% (Kramarow et al., Health and Aging Chartbook, Health, United States, Hyattsville: National Center for Health Statistics, 9, 222 (1999)). Reductions of as little as 5-6 mm Hg in diastolic blood pressure maintained over a 5-year period can decrease CVD risk by 20-25% and stroke risk by 35-40% (MacMahon et al., Lancet, 335, 765 (1990)).

The National Cholesterol Education Program (NCEP) advocates diet therapy as the primary intervention for lowering serum cholesterol concentrations, whereas drug therapy is reserved only for those individuals not responding adequately to diet and who exhibit a high risk cardiovascular disease profile (National Cholesterol Education Program, Second Report of the Expert Panel on Detection, Evaluation, and Treatment of High Blood Cholesterol in Adults (Adult Treatment Panel II), Bethesda: National Institutes of Health, National Heart, Lung, and Blood Institute, National Cholesterol Education Program, 1993). Based on these guidelines, it has been estimated that 29% of all adults in the US would require dietary therapy (Sempos et al., JAMA, 269, 3009 (1993)).

Pharmacological therapy is generally recommended for the treatment of hypertension (The Sixth Report of the Joint National Committee on Prevention, Detection, Evaluation, and Treatment of High Blood Pressure, Arch. Intern. Med., 157, 2413 (1997)). Yet because of its cost and adverse side effects various dietary approaches to the treatment and prevention of hypertension have been gaining growing acceptance and popularity (Appel et al., N. Engl. J. Med., 336, 1117 (1997); Sacks et al., New Engl. J. Med., 344, 3 (2001); Eliasson et al., J. Hypertens., 10, 195 (1992)).

The use of viscous (soluble) fibers is one of the diet strategies shown to decrease serum cholesterol concentrations (Glore et al., J. Am. Diet. Assoc., 94, 425 (1994)). Based on data from controlled clinical trials it has been estimated that daily intake of 2-10 grams per day (g/d) of soluble fiber significantly decreases total and LDL-cholesterol (Brown et al., Am. J. Clin. Nutr., 69, 30 (1999)). Specifically, consumption of β-glucan-containing oat products leads to an average cholesterol reduction of 5.9 milligrams per deciliter (mg/dL) (Ripsin et al., JAMA, 267, 3317 (1992)). On the other hand, intake of insoluble, non-viscous fibers, such as cellulose, does not lower lipid concentrations (Truswell and Beynen, Dietary Fiber and Plasma Lipids: Potential for Prevention and Treatment of Hyperlipidemias, In: Schweizer and Edwards, eds., Dietary Fiber—A Component of Food, New York: Springer Verlag, 295-332 (1992)).

Besides a hypolipidemic effect, there is a growing body of literature suggesting that viscous (soluble) fibers also lower blood pressure (Keenan et al., Adv. Exp. Med. Biol., 427, 79 (1997)) and CVD risk in general (Anderson, Can. J. Cardiol., 11, 55G (1995); Anderson and Hanna, J. Nutr., 129, 145S (1999)). Soluble, dietary fiber consumption has been inversely related to hypertension (Ascherio et al., Circulation, 86, 1475 (1992)) and diastolic blood pressure (Ludwig et al., JAMA, 282, 1539 (1999)) and several intervention studies of viscous fibers have reported blood pressure reductions in both hypertensive and normotensive individuals (Wright et al., Br. Med. J., 2, 1541 (1979); Schlamowitz et al., Lancet, 2, 622 (1987); Singh et al., J. Hum. Hypertens., 7, 33 (1993); Saltzman et al., J. Nutr., 131, 1465 (2001)). However, the practical utility of viscous fibers as hypocholesterolemic and hypotensive agents is often limited by the lower gastrointestinal side effects associated with increased consumption and related to their fermentability.

As early as the 1960s individuals who secreted abnormally large amounts of insulin in response to dietary carbohydrate were shown to have high incidence of vascular disease, suggesting that insulin may play a major role in the pathogenesis of arteriosclerosis (Stout and Vallence-Owen, Lancet, 1, 1078 (1969)). Epidemiological studies since then have supported an independent association between hyperinsulinemia and cardiovascular disease (CVD) (Ducimentiere et al., Diabetologia, 19, 205 (1980); Pyörälä et al. Acta Med Scand Suppl., 701, 38 (1985); Després et al., N. Engl. J. Med., 334, 952 (1996); Cavallo-Perin et al., Metabolism, 50, 30 (2001)). Individuals with fasting insulin concentrations above the median level have 5.5 times the odds of developing heart disease than those without hyperinsulinemia after adjustment for a variety of lifestyle and genetic factors (Lamarche et al., JAMA, 279, 1955 (1998)).

Diabetes is a disease in which the body does not produce or properly use insulin, the hormone needed to convert sugar, starches and other food into energy needed for daily life. Type I diabetes and type II diabetes are the two major types of diabetes. Type I diabetes is a disease where the body fails to produce insulin. As a result, people with type I diabetes must take daily insulin shots to stay alive. Type II diabetes results from insulin resistance, which is a condition in which the body fails to make enough or properly use insulin. This insulin resistance is also combined with relative insulin deficiency in type II diabetes. Often, type II diabetes can be controlled through diet, nutrition and lifestyle changes, but many people may also need oral medications and/or insulin to control their diabetes. The cause of diabetes at present is unknown, although both genetics and environmental factors such as obesity and lack of exercise appear to play roles.

Insulin resistance is a state of reduced insulin sensitivity, characterized by an inability of insulin to lower plasma glucose concentrations through suppression of hepatic glucose production and stimulation of glucose utilization in skeletal muscle and adipose tissue. Insulin resistance appears to be involved in the etiology and progression of CVD, type II diabetes and hypertension (Reaven, *Diabetes*, 37, 1595 (1988)). Epidemiological studies have confirmed the predictive role of hyperinsulinemia and insulin resistance in type II diabetes (Charles et al., *Diabetes*, 40, 796 (1991); Haffner et al., *Diabetes*, 41, 715 (1992); Lillioja et al., *N. Engl. J. Med.*, 329, 1988 (1993)) and their strong relationship to hypertension (Haffner et al., *Diabetes*, 41, 715 (1992); Ferranninni et al., *N. Engl. J. Med.*, 317, 350 (1987)); Swislocki et al., *Am. J. Hypertens.*, 2, 419 (1989); Zavaroni et al., *J. Int. Med.*, 231, 235 (1992)).

Studies in experimental animals have noted that treatment with insulin results in lipid-containing lesions (Stout, *Br. Med. J.*, 3, 685 (1970)), thickening of the arterial wall (Sato et al., *Diabetes*, 38, 91, (1989)), as well as inhibition of the regression of diet-induced arteriosclerosis (Stamler et al., *Circ. Res.*, 8, 572 (1960)). Furthermore, insulin has been shown to stimulate cholesterol synthesis in cultured arterial smooth muscle cells (Stout, *Arteriosclerosis*, 27, 271 (1977)) and monocytes, as well as in insulin-treated diabetic patients (Feillet et al., *Metabolism*, 43, 1233 (1994); Scoppola et al., *Diabetologia*, 18, 1362 (1995)). Hyperinsulinemia appears to be at the center of metabolic abnormalities including elevated triacylglycerol, depressed HDL-cholesterol, small, dense LDL particles, abdominal obesity and hypertension, and may thus mediate their effect on risk for CVD, type II diabetes and hypertension.

Immigrants representing Asian, African and Hispanic ethnic groups are displaying alarming prevalence of type II diabetes mellitus (AODM) within short periods of time after entering the United States. The Native American populations within the United States presently display nearly 100% prevalence of type II diabetes on some Tribal reservations. Because of an aging immigrant population, Native American population and an aging Caucasian population, researchers have predicted that type II diabetes, and diseases such as cardiovascular disease, kidney disease and blindness, will be seen in epidemic proportions.

Intervention studies in the last several decades have investigated the possibility that the above-mentioned conditions are modifiable and their modification can reduce the incidence and mortality from these conditions. Many trials have investigated the effects of soluble, dietary fiber on these conditions. For example, several trials have been conducted to test the effectiveness of various soluble, dietary fibers to modify cardiovascular disease. Results, however, have been highly variable. Furthermore, despite multiple theories of the mechanism by which soluble fiber acts to decrease serum cholesterol levels and attenuate glucose and insulin response, it is still unclear how such fibers exert their effects.

Dietary fiber is a mixture of three major fractions: structural polysaccharides, structural non-polysaccharides and nonstructural polysaccharides (Schneeman, *Food Technol.*, 40, 104 (1986)). The main components of dietary fiber are further classified based on their solubility in water. The insoluble components include cellulose, lignin, and most hemicelluloses, while the soluble or viscous components are the mucilages (gums), pectin and some hemicelluloses. Fermentability is another property that distinguishes fibers and seems to be linked to their physiologic effects. Generally, very viscous, soluble fibers, such as gums, oat bran and pectin are highly fermentable whereas insoluble fibers, such as cellulose, are only slightly fermentable (Slavin, Dietary Fiber, In: Matarese L S, Gottschlich M M, eds. Contemporary Nutrition Support Practice, New York: W B Saunders, 174-182 (1998)).

Categorization of dietary fiber is related to the method by which fibers are quantified and their respective retrieval under certain physicochemical conditions (Slavin, *JADA*, 87, 1164 (1987)). However, classifications of fibers have not proved to be especially useful in predicting their behavior in the intact organism, making it important to study various fibers individually and comparatively.

Many food and agricultural byproducts contain a substantial amount of cellulose fibers. Cellulose, a polymer made by plants having an empirical formula $((C_6H_{10}O_5)_n)$, is an important basic molecular unit of plant fibers and the major polysaccharide in plant cell walls (Falk, S. et al., *Physiol. Planetarium*, 11, 802 (1958); Frey-Wyssling, A., Deformation and Flow in Biological Systems, Interscience Publishers, Inc., New York (1952); Parrott, M. E. and Thrall, B. R., *J. Food Sci.*, 43, 759 (1978)). The long, thread-like cellulose chains are composed of thousands of glucose molecules, linked together by glycosidic β-1,4 linkages, with intramolecular hydrogen bonding that makes β-linkages extremely stable.

Because of the spatial orientation of the glucose units, cellulose is a linear polymer that can pack very closely together into large, insoluble polymers, which serve a structural role in the plant. For example, the linear polymer of cellulose can form crystalline structures, where the polysaccharide chains are organized into a regular packing arrangement. In addition to the crystalline structure, cellulose can also have amorphous structures, where the polysaccharide chains are in a disorganized state that does not allow for a regular packing arrangement. Furthermore, individual cellulose chains layer themselves on one another, forming "microfibrils," which contain areas of denser crystalline regions. This arrangement makes cellulose a rather inert entity, unable to participate in chemical reactions unless its fibrous structure is disrupted.

The cellulose fibers can also include lignin, which is a complex polymer of phenylpropane units and hemicellulose. Within the cellulose fibers, cellulose and lignin can be cross-linked. The cross-linking interaction between the glucose molecules of cellulose and lignin makes the cellulose fiber a very stable and resistant material to degradation by weather, microbial attacks and human digestions. Hemicellulose is a polysaccharide that can also be found associated with cellulose, where the branched chains of this molecule bind to cellulose microfibrils, together with pectins, forming a network of cross-linked fibers.

The practical use of soluble fiber is limited by the untoward side effects associated with increased consumption. Studies have reported gastrointestinal discomfort, including flatulence, bloating, nausea, feeling of fullness, and loose stools. In addition, many soluble fibers have marginal palatability (e.g., guar gum) or are difficult to consume frequently because of their energy content (e.g., oatmeal). These issues limit the quantity of soluble fiber a person can consume, and thus, limit the amount of benefit to be experienced.

SUMMARY OF THE INVENTION

The present invention provides a method for using processed cellulose. Preferably, the processed cellulose is a highly refined cellulose (HRC). The HRC is useful in a number of medical and nutritional applications. These medical and nutritional applications can include, but are not limited to, administering effective amounts of the HRC for lowering values of risk factor measurements for such diseases as arteriosclerotic cardiovascular disease and diabetes. Treatment of other diseases and conditions with the HRC is also possible.

The HRC used in the present invention typically displays a substantially insoluble characteristic, a substantially indigestible characteristic and a substantial water retention capacity (WRC). The substantially insoluble characteristic of HRC includes the characteristic that HRC does not significantly dissolve in an aqueous solution, but rather forms a dispersion in solution, where discrete particles of HRC are in the aqueous solution.

As for the being substantially indigestible, the HRC is not substantially broken down by human digestive enzymes, and therefore is not absorbed by the human body. The HRC is also not substantially metabolized by microorganisms in the gastrointestinal (GI) tract of the human. The HRC used in the present invention also displays a substantial water retention capacity and viscosity values that have typically only been associated with soluble fibers, such as β-glucans. The HRC used in the present invention, however, does not cause many of the undesirable side effects of these unprocessed fibers, such as intestinal gas, diarrhea, bloating and abdominal discomfort.

In one aspect, the present invention provides a method that includes providing an effective amount of the HRC, where ingesting the HRC can be effective to change at least one risk factor value for diabetes in a mammal. In an additional aspect, the HRC effective to change at least one risk factor according to the present invention can include increasing an insulin sensitivity ($S_I$) of the mammal. In another aspect, the HRC effective to change at least one risk factor for diabetes according to the present invention can include increasing an acute insulin response to glucose (AIRg) of the mammal. In a further aspect, the HRC effective to change at least one risk factor for diabetes according to the present invention can include increasing a disposal index of the mammal, where increasing the disposal index can include changing the AIRg value, the insulin sensitivity value, or a combination thereof, of the mammal.

Another aspect of the present invention, the method includes providing an effective amount of the HRC to the mammal, where ingesting the HRC and a nutritional source is effective to cause an acute decrease in the production of cholecystokinin in a mammal compared to the mammal ingesting the nutritional source. In one aspect, the acute decrease in the production of cholecystokinin in the mammal occurs no less than about twenty minutes after ingesting the effective amount of the HRC.

The present invention is further directed to a method that includes providing an effective amount of the HRC to a mammal, where ingesting the HRC is effective to change at least one risk factor value for arteriosclerotic cardiovascular disease in the mammal. For example, changing at least one risk factor value for arteriosclerotic cardiovascular disease can include decreasing blood pressure in the mammal. In an additional example, changing at least one risk factor value for arteriosclerotic cardiovascular disease can include decreasing serum lipids in blood of the mammal. Decreasing serum lipids for the present invention include, but are not limited to, decreasing the total cholesterol, decreasing HDL-cholesterol, decreasing LDL-cholesterol, decreasing the triglycerides, or a combination thereof, of the mammal.

In some aspects of the present invention, the method includes providing an effective amount of the HRC to the mammal, where ingesting the HRC is effective to decrease serum lipids in blood of a mammal. In an additional aspect of the invention includes providing an effective amount of the HRC to a mammal, where ingesting the HRC increases a disposal index of the mammal. In one aspect, increasing the disposal index of the mammal can include changing the AIRg value, the insulin sensitivity value, or a combination thereof, of the mammal through providing the HRC.

In an additional aspect of the present invention, the method includes providing an effective amount of the HRC to a mammal, where ingesting the HRC is effective to cause a metered release of a nutrient source to a mammal. In one aspect of the invention, the HRC can be mixed with the nutrient source to at least partially saturate the HRC with the nutrient source. Possible nutrient sources are selected from the group consisting of a digestible simple sugar, a digestible complex sugar, a digestible protein, a digestible fat, and a combination thereof. Additional nutrient sources may be a vitamin, minerals, electrolyte, a salt, and a combination thereof.

In another aspect of the present invention, the method includes providing an effective amount of the HRC to the mammal, where ingesting the HRC is effective to decrease blood pressure in a mammal.

Unless otherwise specified, "a," "an," "the," and "at least one" are used interchangeably and mean one or more than one.

DETAILED DESCRIPTION

Figure 1:
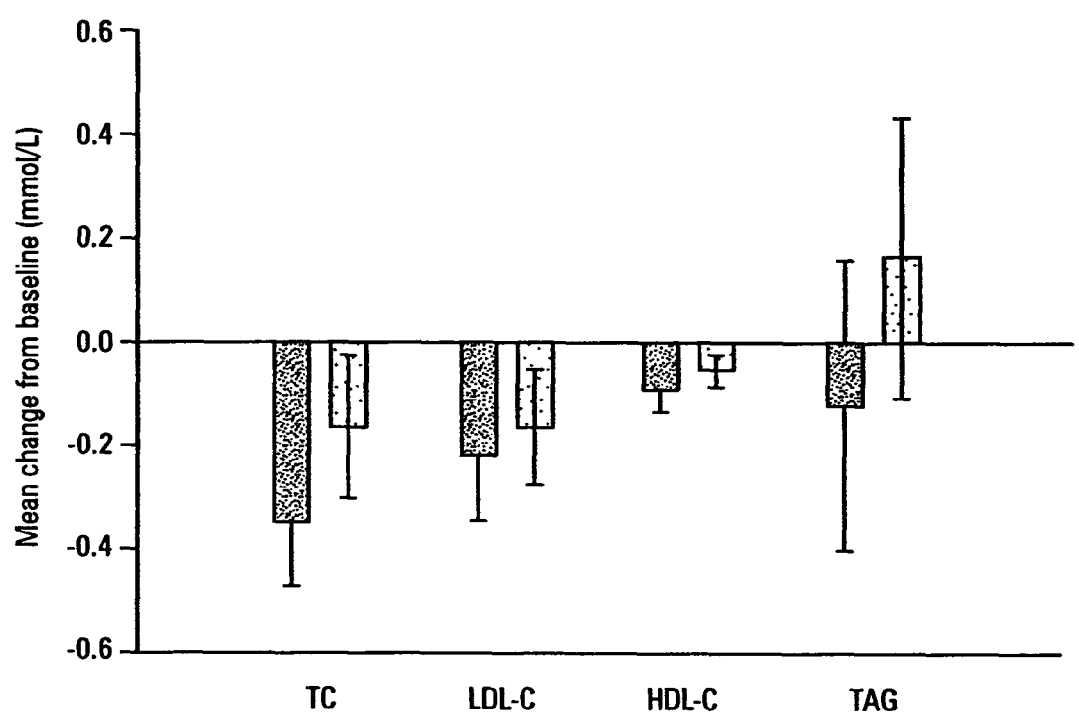
FIG. 1 depicts the mean changes of serum total cholesterol (TC), LDL-cholesterol, HDL cholesterol and triacyglycerol (TAG) (±SEM) from baseline to study end in 16 individuals receiving HRC intervention (black bars) and 16 individuals in the control group (gray bars).

The present invention provides methods for using processed cellulose, preferably a highly refined cellulose (HRC). The HRC typically displays a substantially insoluble characteristic, a substantially indigestible characteristic and a substantial water retention capacity (WRC). The substantially insoluble characteristic of HRC includes the characteristic that HRC does not significantly dissolve in an aqueous solution. Preferably, the HRC does not dissolve in an aqueous solution at all. In either case, the HRC used in the present invention forms a dispersion in solution, where discrete particles of HRC are in the aqueous solution.

The HRC used in the present invention is typically substantially indigestible. For example, the HRC is not substantially broken down by human digestive enzymes, and therefore is not absorbed by the human body. The HRC is also not substantially metabolized by microorganisms in the gastrointestinal (GI) tract of the human. The HRC used in the present invention also typically displays a substantial water retention capacity and viscosity values that have typically only been associated with soluble fibers, such as β-glucans, which are metabolized by the microorganisms of the GI tract, resulting in gas, etc.

Compared to unprocessed insoluble cellulose, the HRC used in the present invention typically has enhanced pore size, internal surface area and water retention capacity. The HRC used in the present invention, however, does not cause many of the undesirable side effects of these unprocessed fibers, such as intestinal gas, diarrhea, bloating and abdominal discomfort. In addition to being substantially insoluble and having a substantial water retention capacity, the HRC used in the present invention can also form highly viscous solutions at relatively low concentrations by weight of the HRC.

Surprisingly, the HRC used in the present invention can be used in a number of medical and nutritional applications, including, but not limited to, administering effective amounts of the HRC for lowering values of risk factor measurements for such diseases as arteriosclerotic cardiovascular disease and diabetes. Treatment of other diseases and conditions with the HRC is also possible.

In addition, a solution or mixture as used herein means that the HRC as used in the present invention can be sufficiently dispersed in water so as to produce transparent, translucent, or opalescent compositions. Such "solutions" generally have no or few visible particles or precipitates of the HRC in the solution, although submicroscopic particles may form to produce a gel. Thus, as used herein "solution" encompasses solutions of various viscosities, including gels.

Throughout the specification, the term "blood lipid" or "serum lipid" designates a lipid present in the blood. The blood lipid can be represented by cholesterol, low-density-lipoproteins, very low-density-lipoproteins (VLDL), intermediate-density-lipoproteins (IDL), and triglycerides carried in the blood.

The terms "high" or "elevated level" of a blood lipid or of blood pressure means higher than normal level varying with specific conditions of a patient, such as age, gender and body weight. A high level of blood lipid and/or high blood pressure can ordinarily be considered to be harmful to health. A constant blood pressure reading of about 140/90 mm Hg or higher is considered high blood pressure, another term for hypertension. Total serum cholesterol of greater than about 200 mg/dL and/or a LDL-cholesterol of greater than about 135 mg/dL can be considered to be high or an elevated level of blood lipids.

As used herein the term "arteriosclerosis" is generally a degeneration of the walls of the arteries due to the formation of foam cells and aortic streaks that narrow the arteries. This limits blood circulation and predisposes an individual to thrombosis. As used herein the term "atherosclerosis" is generally a disease of the arteries in which fatty plaques develop on the inner walls, with eventual obstruction of blood flow.

As used herein the term "hypercholesterolemia" is generally a condition with elevated levels of circulating total cholesterol, low-density lipoproteins (LDL)-cholesterol and/or VLDL-cholesterol as per the guidelines of the Expert Panel Report of the National Cholesterol Educational Program (NCEP) of Detection, Evaluation of Treatment of high cholesterol in adults (see, *Arch. Int. Med.*, 148, 36 (1988); NCEP, (1993); and Expert Panel on Detection, Evaluation, and Treatment of High Blood Cholesterol in Adults, *JAMA*, 285, 2486 (2001).

As used herein, the term "hyperlipidemia" is generally a condition where the blood lipid parameters are elevated in the blood. For example, elevated blood lipid values can include total serum cholesterol of greater than about 200 mg/dL and/or a LDL-cholesterol of greater than about 135 mg/dL.

This condition manifests an abnormally high concentration of fats. The lipid fractions in the circulating blood include total cholesterol, low-density-lipoproteins, very low-density-lipoproteins (VLDL), IDL, and triglycerides.

As used herein, the phrase "arteriosclerotic cardiovascular disease" is intended to encompass those diseases that tend to be associated with high blood pressure and/or high serum lipids. These diseases include, for instance, coronary heart disease, arteriosclerosis, atherosclerosis, thrombotic stroke, cerebrovascular disease, peripheral vascular disease, hypertension, congestive heart failure, coronary artery disease, and ischemic heart disease.

As used herein the term "lipoprotein" such as VLDL, LDL, IDL and high-density lipoproteins (HDL), refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

As used herein the term "triglyceride" means a lipid or neutral fat consisting of glycerol combined with three fatty acid molecules.

A used herein the term "cholesterol" refers to a white crystalline substance, empirical formula $C_{27}H_{45}OH$, that occurs naturally in animal tissues and various foods, that can normally be synthesized by the liver and can be important as a constituent of cell membranes and a precursor to steroid hormones (vitamin D and bile acids that help digest fat). It only takes a small amount of cholesterol in the blood to meet these needs. A high level in the bloodstream is thought to be related to various pathogenic conditions, such as the development of arteriosclerotic plaque and coronary artery disease (where it is believed to contribute to the narrowing and blockages of the coronary arteries).

The present invention provides for, besides other things, the use of processed cellulose in medical and nutritional applications. Preferably, the processed cellulose for use in the methods of the present invention can be derived from cellulose fibers and/or hemicellulose. More preferably, the processed cellulose for use in the methods of the present invention can be derived from cellulose fibers. Preferably, the processed cellulose used in the present invention can be a highly refined cellulose (HRC). As will be discussed below, there are a variety of processes for making highly refined cellulose products from cellulose fiber sources, including even minor amounts of wood fibers as additives. Preferably, HRC can be a hydrocolloidal material manufactured from insoluble and non-fermentable cellulose, as will be discussed more fully below. During the manufacturing, there may be a physical modification of the polymer structure of cellulose that results in hydrophilic regions of the cellulose being exposed, allowing for, besides other things, HRC to absorb increased amounts of water.

Preferably, the HRC used in the present invention can be made from a suitable cellulose fiber source, such as harvest residue crop fiber and other crop waste fiber sources such as silage, stalks, leaf (including tree leaves), and the like. Other cellulose fiber sources are also possible. In one example, the process converts raw fibrous materials, such as corn cobs, husks and stalks, or other cellulose fiber sources, into a fibrous slurry and by using pressure mixing, such as homogenization, the fibrous slurry can then be processed into the highly refined cellulose (HRC).

Generally, making HRC involves physically modifying the cellulose fibers to alter the crystalline structure of the cellulose fibers. Preferably, the modification process disrupts the crystalline structure of the cellulose fibers to produce a more highly amorphous cellulose fiber structure as compared to the starting cellulose fibers. The results of disrupting the crystalline structure of the cellulose fibers to produce HRC include exposing additional hydrophilic regions in the HRC. In addition, the disruption process also forms a porous network substantially throughout the HRC. While not wishing to be bound by theory, it is believed that in addition to being present on the outer surface of the HRC, the hydrophilic regions also line the porous network that extends through the HRC.

The HRC used in the present invention has different physical characteristics than the starting cellulose fibers. For example, HRC has a higher water retention capacity and oil retention capacity as compared to the starting cellulose fibers (Gu et al., Transactions of the American Society of Agricultural Engineers, Vol. 44(6), 1707-1712, 2001). HRC also has a larger surface area than the starting cellulose fibers on a per weight basis (Gu et al., Transactions of the American Society of Agricultural Engineers, Vol. 44(6), 1707-1712, 2001).

HRC also displays increased viscosity values for cellulose solutions having comparable amounts of cellulose material on a weight basis. For instance, HRC materials display a 1% water retention capacity (WRC) of 45 grams of water per gram of HRC, and a 1% concentration (99% water) viscosity of 1200 centipoise (cP) when measured at 10 rpm using a Brookfield LVDV++viscometer (Middleboro, Mass.) with cylindrical spindles at 25 degrees Celsius. For the unprocessed cellulose starting material, the WRC was 7.7 grams of water per gram of cellulose solid, and the 1% concentration viscosity was less than 10 cP.

Preferably, the HRC used in the present invention can have viscosity values for a 1% concentration by weight in water at 25 degrees Celsius of no less than about 5,000 cP. In an additional preferred embodiment, the HRC used in the present invention can have viscosity values for a 1% concentration by weight in water at 25 degrees Celsius of no greater than about 40,000 cP.

The particle size of the HRC used in the present invention can vary depending upon the process conditions and the extent of shearing the particles encounter. Preferably, the particle size of the HRC used in the present invention is no less than about 50 microns. Also preferably, the particle size of the HRC used in the present invention is no greater than about 100 microns. More preferably, the particle size of the HRC used in the present invention is about 70 microns.

HRC microstructure (e.g., porosity, surface area) effects the water retention capacity (WRC) of the HRC. The WRC values for HRC as used herein were determined in accordance with Method 56-10 of the American Association of Cereal Chemists (AACC). Using this procedure, the WRC of a 1% HRC dispersion was measured. In one example, the WRC was measured from the amount of water retained under standard centrifuge at 1000 g.

HRC microstructure varies depending upon both the process parameters and the starting cellulose material. Generally, the WRC of the HRC increases as both BET surface area and Langmuir surface area increase. Preferably, the WRC of the HRC is greater than about 10 grams of water per gram of dry HRC, where dry HRC has substantially no water. More preferably, the WRC of the HRC is at least about 20 grams of water per gram of dry HRC. In a further preferred embodiment, the WRC of the HRC is at least about 30 grams of water per gram of dry HRC. Preferably, the WRC of the HRC is no greater than about 70 grams of water per gram of dry HRC. In a further preferred embodiment, the WRC of the HRC is no greater than about 60 grams of water per gram of dry HRC. More preferably, the WRC of the HRC is no greater than about 50 grams of water per gram of dry HRC.

The HRC used in the present invention further includes a substantially amorphous structure, with little to no crystalline morphology. As discussed above, the cellulose fiber starting material typically has a high degree of crystallinity in the cellulose. Decreasing the crystalline morphology in the HRC can be due in part to the processing conditions and operating parameters used in producing the HRC. Once this occurs, the molecular structure of the HRC is altered to the extent that recrystallization of the cellulose does not occur to any significant extent. As such, the HRC used in the present invention has a substantially amorphous morphology.

In one example, the crystallinity index of unprocessed (ball milled) cellulosic fibers is about 1.62, whereas the crystallinity index of HRC has a value of about 0.99, where the lower the crystallinity index number the more amorphous the material. In an additional example, unprocessed ball milled cellulosic fibers with an average particle size of about 100 microns was found to have a crystallinity index of about 1.62, and a surface area of about 0.9 sq. meters per gram. In contrast, one example of the HRC used in the present invention was found to have an average particle size of about 200 microns, a crystallinity index of about 0.99, and a surface area of about 37 sq. meters per gram.

Surprisingly, the crystalline structure of the cellulose fibers can be decreased in producing HRC without destroying either the cellulose molecule or substantially changing the chemical composition of the cellulose fiber. Thus, under certain processing conditions the HRC can have modified physical characteristics, but substantially the same chemical composition as the starting cellulose fibers (Gu et al., Transactions of the American Society of Agricultural Engineers, Vol. 44(6), 1707-1712, 2001).

In addition, HRC has a highly porous structure with a large surface area that provides hydroxyl groups accessibility to water and other chemicals (Gu et al., Transactions of the American Society of Agricultural Engineers, Vol. 44(6), 1707-1712, 2001). For example, as compared to the starting cellulose fibers, the HRC used in the present invention has a much larger surface area as determined using both BET and Langmuir surface area determinations. (Gu et al., Transactions of the American Society of Agricultural Engineers, Vol. 44(6), 1707-1712, 2001).

The pore size and the surface area of the HRC may be measured using a MICROMERITICS 2000 from Micromeritice Instrument Co. For instance, the HRC can be exposed to 6 mm Hg vacuum at 85° C. to degas and remove moisture and other contaminants from the HRC. The HRC may then be analyzed in a nitrogen gas environment and the average pore diameter, BET surface area and Langmuir surface area measured. The BET surface area values are typically determined by calculating the monolayer volume of adsorbed gas from the isotherm data. The Langmuir surface area values are typically obtained by relating the surface area to the volume of gas adsorbed as a monolayer.

In one example, the BET surface area and Langmuir surface area of the starting cellulose fibers were about 1.01 $m^2$/g sample and about 1.68 $m^2$/g, respectively. The HRC produced from this starting material had peak surface area values of about 6.35 $m^2$/g for BET surface area and about 10.48 $m^2$/g for Langmuir surface area. These were observed at 0.0071 g/g water sodium hydroxide concentration, where the sodium hydroxide present in the water remained after processing the starting cellulose to form the HRC.

The HRC useful in the methods described herein also typically contains pores within the cellulose molecules, which would theoretically enable increase bonding interactions (e.g., hydrogen bonding interactions) and entrapment of water, oil, and other compounds, resulting in a highly viscous product as described herein. Pore structure determines the internal accessible surface area of a cellulose substrate and thus affects its accessibility or reactivity. Cellulosic materials contain pores of various sizes.

The HRC may have an average pore diameter of about 39 Angstroms to about 49 Angstroms. The HRC having this average pore diameter occurred in a cellulose sample processed by using 0.0125 g/g water sodium hydroxide concentration. HRC used in the present invention can also have average pore diameters that are preferably from at least about 20, to at least about 60 Angstroms. While not wishing to be bound by theory, it is believed that the lignin concentration of the starting cellulose material may have an influence on the resulting pore size of the HRC. This may be beneficial in tailoring pore sizes for specific purposes for the HRC. For example, it may be possible to have larger pore sizes for the HRC to allow for a higher release rate of materials (e.g., a nutrient source, a drug or other compound) from the HRC. Alternatively, it may be possible to have smaller pore sizes for the HRC to allow for a slower release rate of materials (e.g., a nutrient source, a drug or other compound) from the HRC. Thus, pore size may influence release rates of compounds from the HRC.

The HRC used in the present invention can be created through the use of different processes. In one example, the manufacturing process for HRC is described in U.S. Pat. Nos. 5,817,381 and 6,083,582, both to Chen et al. Briefly, the manufacturing process includes both a chemical and a pressure mixing process, such as a homogenization process. In the process, the size of the cellulose fibers can be reduced by mechanical action to less than 2 mm (or less than 10 mesh). Lignin present in the cellulose fibers can then be removed through the use of high temperature and pressure processing conditions. Alternatively, the cellulose fibers can be treated with a base, such as alkali metal hydroxide, at specific temperatures to reduce the amount of lignin present in the cellulose fibers. Lignin can be reduced in the cellulose fibers to less than about 1.0% and potentially down to about 0% lignin by weight of solid.

The result of either process is a first fiber product. The first fiber product can then be mixed in liquid under a pressure of at least 300 lbs./$in^2$, or more. The pressure can then be removed within a time interval sufficient to cause the cellulose fibers to be transformed (e.g., to change) into the HRC used in the present invention. Changes to the cellulose fibers in being transformed into the HRC by this method include, but are not limited to, reducing the percentage of crystalline structure in the cellulose fibers of the starting material, reducing the amount of lignin and lignin cross-linking in the cellulose fibers of the starting material.

Besides the preferred example provided above, it is believed that HRC as described above can be produced by other possible methods and used according to the present invention. These additional HRC products, or cellulose products having comparable physical and chemical structures to HRC as described herein, might be made in any number of ways with any number of comparable HRC products. Preferably, these HRC products might exhibit insolubility, increased WRC, increased surface area, increased porosity, altered crystalline structure and possibly, but not necessarily, lignin concentrations as compared to the starting cellulose material.

In additional preferred example for producing HRC is described in U.S. patent application Ser. No. 09/432,945 entitled "Cellulose Fiber-Based Compositions and Their Method of Manufacture" to Lundberg et al. Briefly, the method includes soaking the cellulose fibers in an alkaline solution (i.e., basic pH). The solution can include pH values of 7 and above. Preferably, the solution has a pH value of about 10 to about 12. In addition, the solution preferably has no greater than a 0.5 molar concentration of the base.

Preferably, the cellulose fibers are soaked in the alkaline solution at a temperature of no less than about 20 degrees Celsius. Alternatively, the cellulose fibers are soaked in the alkaline solution at a temperature of no greater than about 100 degrees Celsius. Soaking time depends upon both the temperature and the concentration of alkaline solution.

After soaking in the alkaline solution, the cellulose fibers are washed with water, optionally bleached and then washed again with water. The cellulose fibers are then shredded (e.g., through the use of a plate refiner) to produce microfibers. The microfibers are then homogenized at high pressure. Preferably, the pressure used during homogenization can be no less than about 5000 psi. As the microfibers exit the homogenizer, the change from a high-pressure environment to atmospheric pressure environment causes a change in the physical structure of the cellulose fibers, leading to a physical change in the cellulose due to the rapid change in pressure upon exiting the homogenizer. In an alternative embodiment, the microfibers could also possibly be released from the homogenizer into a vacuum so as to provide for a pressure change substantial enough to cause the change in the physical structure of the cellulose fibers.

The physical change in the cellulose can be envisioned as a "puffing" (e.g., an expansion in volume) of the cellulose fibers due to the pressure differential. Therefore, the combination of pressure and homogenization and subsequent release causes both a mechanical reduction in the size of the microfibers and at the same time alters the microstructure of the reduced sized microfibers, as discussed above.

The resulting HRC includes a lignin content essentially unchanged from the starting cellulose material, but can include a range of values. Preferably, the lignin content is no less than about 0.1% by dry weight of the HRC. In an additional preferable embodiment, the lignin content is no less than about 1% by dry weight of the HRC. Also preferably, the lignin content is no less than about 5% by dry weight of the HRC. In a further preferred embodiment, the lignin content is no less than about 10% by dry weight of the HRC. Also, preferably, the lignin content is no less than about 15% by dry weight of the HRC. An additional preferred embodiment includes a lignin content of no greater than about 20% by dry weight of the HRC. Also, preferably, the lignin content is no greater than about 15% by dry weight of the HRC. In a further preferred embodiment, the lignin concentration is no greater than about 10% by dry weight of the HRC. Finally, in a preferred embodiment, the lignin concentration is no greater than about 5% by dry weight of the HRC. It is also possible to add additional lignin to the HRC product, thereby increasing the percentage of lignin by dry weight of the HRC.

The methods of the present invention include treating a mammal, preferably a human, for various conditions. The terms "treatment," "treat," and "treating" as used herein refers to the treatment of a disease or medical condition in a patient, such as a mammal (particularly a human) that includes:
  (a) preventing the disease or medical conditions from occurring, e.g., prophylactic treatment of a patient;
  (b) ameliorating the disease or medical condition, e.g., eliminating or causing regression of the disease or medical condition in a patient;
  (c) suppressing the disease or medical condition, e.g., slowing or arresting the development of the disease or medical condition in a patient; or
  (d) alleviating the symptoms of the disease or medical condition in a patient.

For example, treatment of a cardiovascular condition can also include prophylactic treatment thereof to prevent such a condition from occurring or reoccurring. As used herein, "patient" and "subject" refers to animals, including mammals, preferably humans.

Administration of HRC can be performed before, during, or after the occurrence of the conditions described herein. Treatment initiated after the development of a condition may result in decreasing the severity of the symptoms of one of the conditions, or completely removing the symptoms. Non-limiting examples of subjects particularly suited to receiving the composition are those who may have, or be at risk for, developed diabetes, arteriosclerotic cardiovascular disease, obesity, and/or high cholesterol.

HRC provided to a mammal, for example a human, who has or is at risk of developing a condition described herein, includes providing an effective amount of the HRC, as described herein. The term "effective amount" or "therapeutically effective amount" refers to an amount sufficient for effective treatment when administered to a patient in need of treatment. In some aspects, the present invention includes providing an effective amount of HRC to a mammal, where the HRC can be effective to cause changes in values of various risk factor measurements for conditions. The HRC used in the present invention can be used in the preparation of products for the food, pharmaceutical, nutraceutical, and medical industries, to name only a few. Preferably, the HRC, or a mixture of HRC and another fiber(s), can be administered orally to the digestive tract of the mammal.

In some aspects, the invention generally relates to a nutritional or pharmaceutical composition that can be useful for treating arteriosclerotic cardiovascular disease, coronary heart disease, heart disease, arteriosclerosis, or atherosclerosis. In other aspects, the invention relates to a nutritional or pharmaceutical composition that can be useful for treating glucose intolerance and/or diabetes (Type I and/or Type II; for instance by lowering the fasting or postprandial concentration of plasma glucose, or increasing insulin sensitivity, or combinations thereof). The invention further relates to a nutritional or pharmaceutical composition that can be useful for treating GI irregularities and wounds, such as skin wounds including burns.

Preferably the HRC, or a mixture including HRC, can be administered in combination with a pharmaceutically acceptable excipient, carrier or diluent, i.e., in one or more pharmaceutical unit dosage forms, such as tablets, gelatin capsules, pre-measured solutions intended for ingestion, and the like. While the method of administration may vary, the HRC is desirably administered orally and preferably is ingested by a patient as an ingredient of their daily diet, i.e., in combination with a food and/or a liquid vehicle, such as water, milk, juice and the like, or in an ingestible solid or semi-solid matrix, such as in combination with conventional tabletting excipients, or in capsule fills such as polyethylene glycols, natural gels, and the like.

The amount of HRC incorporated into a pharmaceutical unit dosage form can be of almost any value, since taste and rheology are not primary considerations. For example, amounts from at least about 20, to at least about 50 total weight %, and from no greater than about 98, to no greater than about 80 total weight % of HRC can be used. Preferably, effective amounts of the HRC used in the present invention include ingesting from at least about 2 grams HRC (dry weight) per 1,000 kilocalories (kcal) of total food consumed daily, to at least about 30 grams HRC (dry weight) per 1,000 kcal can be appropriate in most circumstances. Preferably, at least about 5 grams HRC (dry weight) per 1,000 kcal can be consumed daily, to at least about 20 grams HRC (dry weight) per 1,000 kcal can be consumed daily. Preferably, at least about 5 grams of HRC will be administered/consumed daily, to at least about 100 grams of HRC can be administered/consumed daily. More preferably, at least about 5 grams of HRC can be administrated daily. In some aspects, the HRC is administered for a treatment interval. A treatment interval may be at least about one (1) week, at least about two (2) weeks, at least about four (4) weeks, or at least about six (6) weeks. Other treatment intervals are also possible.

Examples of conditions include, but are not limited to, arteriosclerotic cardiovascular disease and diabetes. Specific examples of risk factor measurement values that can be changed according to the present invention include, but are not limited to, blood pressure values (e.g., diastolic value and/or systolic value), values for various serum lipids (e.g., triglycerides, total cholesterol, high and low density lipoprotein cholesterol), values for disposal index, acute insulin response to glucose values, insulin sensitivity values, production of cholecystokinin values, to name only a few.

An aspect of the invention includes a method for treating diabetes. Preferably, the present invention relates to the use of HRC in treating diabetes in a mammal (e.g., a human). In treating diabetes, the effective amount of the HRC administered to the mammal may be ingested in one or more doses over the duration of a treatment interval. More preferably, the present invention relates to the use of HRC in treating a mammal with diabetes where the HRC can be effective to change at least one risk factor for diabetes in the mammal. Risk factors for diabetes that can be changed by HRC include, but are not limited to, increasing insulin sensitivity ($S_I$) of the mammal, increasing acute insulin response to glucose (AIRg) of the mammal, and/or increasing a disposal index of the mammal.

Insulin sensitivity ($S_I$) represents the increase in glucose clearance per unit increase in plasma insulin concentration. Higher $S_I$ values indicate greater sensitivity to insulin and the $S_I$ parameter is highly correlated with insulin sensitivity as assessed by the clamp method (Saad et al., *Diabetes*, 43, 1114-21). The acute insulin response to the intravenous glucose (AIRg) represents the first phase insulin response and can be calculated as the increment of plasma insulin above the basal concentrations from 0 to 10 minutes, following a glucose bolus (Lerner et al., *J. Clin. Endocrinol. Metab.*, 33, 409 (1971)). Finally, the relationship between acute insulin response and insulin sensitivity has been determined to be hyperbolic, allowing the use of the insulin sensitivity-secretion product (the "disposal index") (Bergman et al., *J. Clin. Invest.*, 68, 1456 (1981); Bergman et al., *Diabetes*, 38, 1512 (1989); Kahn, *Diabetes*, 42, 1663 (1993)) to be used in the assessment of n-cell compensation for insulin resistance. The disposal index (DI) may be calculated as the product of $S_I$ and AIRg.

The method includes providing an effective amount of an HRC described herein to the mammal to treat diabetes, where ingesting the HRC can be effective to change at least one risk factor value for diabetes in the mammal. Preferably, at least one risk factor for diabetes changed by the use of HRC includes increasing insulin sensitivity ($S_I$) of the mammal. In one example, an $S_I$ value for study participants, discussed below, increased at least about $0.28+/-1.2(x10^{-5} \cdot min^{-1}$ per pmol/L). In an additional preferred embodiment, a risk factor for diabetes changed by the use of HRC includes increasing the acute insulin response to glucose (AIRg) in the mammal through the use of HRC. In one example, an AIRg value for study participants, discussed below, increased AIRg at least about 47.9+/-1,063 pmol·min/L. An additional preferred embodiment includes increasing a disposal index (DI) of the mammal through the use of HRC. Preferably, increasing the disposal index includes changing one or both of the AIRg and/or insulin sensitivity values of the mammal through the use of HRC. In one example, a DI value for study participants, discussed below, increased at least about 795+/-2,699 ($min^{-1}$).

In an additional preferred embodiment, changing at least one risk factor value includes administering to the patient the effective amount of a HRC, where points on a plotted curve of blood glucose level versus time for the patient decrease after the mammal ingests a sugar source and the highly refined cellulose. The decrease is relative to the points on a plotted curve for the patient ingesting just the sugar source. This decrease may be measured by determining the glucose curve, for instance, area under the curve or total area under the curve. Methods for determining a glucose curve are routine and known to the art.

Another aspect of the invention includes a method for treating arteriosclerotic cardiovascular disease. Preferably, this aspect relates to the use of HRC in treating arteriosclerotic cardiovascular disease in a mammal (e.g., a human). The present invention further provides methods for changing at least one risk factor value for arteriosclerotic cardiovascular disease. The method includes providing an effective amount of the HRC as described herein to treat arteriosclerotic cardiovascular disease in a mammal. In treating arteriosclerotic cardiovascular disease, the effective amount of the HRC administered to the mammal may be ingested in one or more doses over the duration of a treatment interval. One example of changing at least one risk factor includes decreasing serum lipids in blood of the mammal. Examples of changing serum lipids values can include, but are not limited to, decreasing total cholesterol, total serum lipid levels, decreasing HDL-cholesterol, decreasing LDL-cholesterol, and/or decreasing triglycerides of the mammal. For the study participants discussed below, total cholesterol dropped at least about 0.35+/-0.5 mmol/L (13.5+/-19.2 mg/dL), LDL-cholesterol dropped at least about 0.22+/-0.5 mmol/L (8.5 mg/dL), HDL-cholesterol dropped at least about 0.09+/-0.2 (3.5 mg/dL), and triglycerides dropped at least about 0.12+/-0.5 (10.5 mg/dL).

Another example of changing a risk factor value includes treating high blood pressure, by decreasing systolic and/or diastolic blood pressure, especially in those individuals who were previously treated for hypertension. Preferably, systolic and/or diastolic blood pressure is decreased by at least about 2.8 mmHg.

Also provided by the present invention are methods for providing an effective amount of the HRC to a mammal to cause an acute decrease in the production of cholecystokinin in the mammal. Cholecystokinin (CCK) is a peptide hormone and neurotransmitter rapidly secreted by cells in the upper part of the small intestine after the ingestion of food. Amino acids, peptones and fatty acids appear to be the most potent stimulators of CCK secretion, while glucose only weakly stimulates it with a less understood overall effect. CCK regulates gut motility, gall bladder contraction and pancreatic enzyme secretion. Additionally, it potentiates the amino-acid induced release of insulin and glucagon (Rushakoff, *J. Clin. Endocrinol. Metab.*, 65, 395 (1987)), slows gastric emptying, thereby enhancing digestion and absorption of nutrients (Liddle et al., *J. Clin. Invest.*, 77, 992 (1986)) and regulating glucose homeostasis (Liddle et al., *J. Clin. Invest.*, 81, 1675 (1988)). In one preferred embodiment, the acute decrease in the production of cholecystokinin in the mammal occurs no less than about twenty minutes after ingesting the effective amount of the highly refined cellulose.

The present invention can also be directed to methods for providing an effective amount of the HRC to cause a metered release of a nutrient source to the mammal. As used herein, "metered release" refers to the decreased movement of a nutrient source from the digestive tract into the blood of a mammal. In one embodiment, the method includes mixing the nutrient source with the HRC to at least partially saturate the highly refined cellulose with the nutrient source. The HRC/nutrient source mixture could then be use, for example, in a beverage (e.g., a metered energy drink). Examples of nutrient sources include, but are not limited to a digestible simple sugar, a digestible complex sugar, a digestible protein, a digestible fat, vitamins, minerals, electrolytes, a salt (or salts), or a combination thereof, where such nutrient sources are released from the HRC over time.

The use of HRC in a metered nutrient source could be beneficial to individuals in need of sustained and substantially uniform release of calories. These individuals might include endurance athletes, military personnel, safety personnel (e.g., fire fighters, EMT workers, police, etc.) or any other persons. HRC used in the present invention can be mixed and/or combined with a nutrient source (e.g., digestible simple and/or complex sugars, digestible protein, digestible fat, vitamins, minerals, electrolytes, salts or combination of any of the foregoing). The nutrient source can be mixed with the HRC used in the present invention in such a way that the porous structures of the HRC are at least partially filled with and/or bound with the nutrient source. In one example, the nutrient source can be bound to the HRC through non-covalent bond interactions (e.g., hydrogen boding, Van der Waals forces, and/or electrostatic interactions). Alternatively, the nutrient source can be passively present in the porous structure of the HRC.

While not wishing to be bound by theory, it is believed, that when ingested, the nutrient source associated with the HRC leaches from the amorphous cellulose. The leaching process can allow for a slower release of the nutrient source as compared to simply ingesting the nutrient source without HRC, thereby preventing, for example, spikes in blood glucose levels and the subsequent, and usually precipitous, drop in blood sugar levels. As such, the use of HRC might allow for a more uniform and sustained release of the nutrient source. In addition, different nutrient source combinations can be included in the solubilized cellulose. So, for example, two or more carbohydrate sources can be included with the HRC such that a first nutrient source (e.g., simple sugars) that can be released simultaneously, or can be followed by the release, of a second nutrient source (e.g., more complex sugars).

The HRC as used in the present invention also exhibits potential value as a treatment of gastrointestinal (GI) conditions. For example, the HRC used in the present invention might be used as a laxative and/or to increase stool volumes. Used as a laxative, the HRC may be used in maintaining regularity, decreasing transit time, and helping in preventing hemorrhoids, diverticular disease and diverticulitis. Examples of studies to investigate the use of HRC as a laxative would include persons that have displayed a high occurrence of constipation, where the persons would be randomized into either treatment with HRC or as control without HRC. Measurements might include stool transit time, bulk (volume), weight, water content, frequency, and hardness, as well as subjective ratings of difficulty/discomfort with defecation and perceived change in bowel function. With respect to enlarged stool bulk, while not wishing to be bound by theory, it is believed that the enlarged stool bulk is the result of enhanced water uptake by the HRC while in the GI tract. In addition, HRC may be beneficial in treating individuals with irritable bowel syndrome, nervousness/anxiety, among other conditions. Long-term usage of HRC may also result in the prevention of colorectal cancers.

The HRC may also have an additional benefit of increasing the volume and mass in the GI tract, thereby leading to a patient having the feeling of fullness (satiety), which can have an impact on appetite suppression. While not wishing to be bound by theory, it is believed that the HRC used in the present invention binds sugar and fats, thereby making them less available to be absorbed by body. This binding action also may prevent blood sugar levels from dropping, so the individual does not feel hungry too soon after eating. This action may also explain why the over production of insulin can be minimized as the amount of sugar is more slowly and consistently released into the individuals body. Thus, the present invention may also include a method for delaying and lessening the postprandial serum glucose elevation of an individual and/or a method for delaying the absorption of carbohydrates in an individual. Accordingly, the use of HRC according to the present invention may be useful in a weight-reducing diet for overweight or obese subjects.

In a further preferred embodiment, the HRC may also be useful in wound healing applications. For example, the HRC of the present invention can be incorporated into bandages, dressings, tapes, clotting solutions/gels/or packings, sprays, topical ointments, injectables, besides other medical products. In addition to being present in these products, the HRC might also be impregnated with one or more compounds that would be beneficial for the application in which the medical product is being used. For example, antibiotic and/or antimicrobial compounds could be mixed with the HRC, where the HRC absorbs the compounds. In use, the compounds could then leach from the HRC into the surrounding environment. In treating skin disorders, the HRC is preferably administered topically at and around the affected area(s).

Preferably, the HRC used in the present invention would be useful in the preparation of products for the food, pharmaceutical, nutraceutical (also referred to as phytochemicals or functional foods), and medical industries, to name only a few. Nutraceuticals include, but are not limited to, those natural, bioactive compounds that have, or are believed to have, health promoting, disease preventing or medicinal properties.

HRC can be administered directly (preferably in solution) or in powder form, or may be combined with other food ingredients. For example, it may be mixed into foods such as beverages, shakes (i.e., milk shakes), breakfast drinks, juices and flavored drinks, water, yogurt, puddings, ice cream, ice milk, frozen yogurt, cheesecake filling, candy bars, including "health bars" such as granola and fruit bars, gums, hard candy, pastry fillings such as fruit fillings, cereals, breads, prepared stuffing and instant potatoes. Preferably, the HRC used in the present invention might also be used in prepared foods as a replacement for meat or other food stuff, thereby effecting both the fat, cholesterol and calorie content of the food stuff.

Effective amounts of HRC can also be used as a fat substitute in salad dressings, frosting, soups, sauces, gravies, mayonnaise and other spreads. Also, the HRC used in the present invention may be formulated as tablets, granules, capsules and the like. Therefore, "food ingredients", as the term is used herein, includes those ingredients commonly employed in recipes for the above foodstuffs, including flour, fruits, milk, eggs, starch, soy protein, sugar, sugar syrups, vegetable oils, butter, emulsifying agents such as lecithin, and the like.

The foodstuffs described above are preferably formulated to comprise from at least about 0.01, more preferably at least about 0.1, to at least about 20, more preferably to at least about 50% total HRC by weight. In one embodiment, the percentage of HRC will depend on the desired viscosity of the foodstuff. Combinations of concentration and viscosity can be determined experimentally. For example, in a milk shake or pudding, the weight-% can be from at least about 0.1, to at least about 50%. However, in baked goods, a range of from at least 2, to at least about 25 wt-% might be possible, without deleteriously affecting the rheological characteristics of the product.

The present invention is illustrated by the following examples. It is to be understood that the particular examples, materials, amounts, and procedures are to be interpreted broadly in accordance with the scope and spirit of the invention as set forth herein.

EXAMPLES

The following examples were derived from a pilot study conducted on 34 subjects. The data derived from this pilot study was not designed to provide statistically significant data, but rather to identify trends resulting from the use of HRC.

Example 1

Lipid and Blood Pressure Effects of HRC

Study Design

A double blind, placebo-controlled, parallel study was conducted and involved a six-week intervention, preceded by a dietary adaptation period with a minimum of six-week duration. At the beginning of the dietary adaptation period, all subjects who met the inclusion criteria (the reverse of the exclusion criteria provided below, and included meeting the lipid levels mentioned below) received training for the American Heart Associate (AHA) Step I diet (Carleton et al., *Circulation*, 83, 2154 (1991)). Subjects followed the diet for a minimum of six weeks. At the end of the dietary adaptation period, a baseline lipid screen was performed and subjects with total cholesterol (TC)>220 mg/dL or LDL-cholesterol>130 mg/dL were enrolled in the study.

The enrolled subjects were then randomly assigned to the active treatment (referred to herein as the "HRC group") or control group using a fixed allocation randomization scheme with permuted blocks of four and six. Subjects in the HRC group received about 5 grams (g) of HRC daily for 6 weeks, whereas subjects in the control group did not. All subjects followed the AHA Step I diet. Subjects were seen twice within a three-day period before the start of intervention (visits 1 and 2), once weekly during the intervention (visits 3-7) and twice in a three-day period after the end of intervention (visits 8 and 9).

Subjects

Men and women subjects with hypercholesterolemia between the ages of 20 and 75 were recruited. Exclusion criteria included unstable vascular disease, use of hypolipidemic agents within the last 30 days or regularly, diabetes mellitus, uncontrolled hypothyroidism, history of active peptic ulcers, liver or gall bladder disease, major intestinal surgery, malabsorption, or stenosis of the gastrointestinal tract, chronic use of antacids or bulk laxatives, fasting triacylglycerol concentration>4.52 mmol/L (400 mg/dL), excessive alcohol use, body mass index (BMI; in $kg/m^2$)>35, and soluble fiber intake>6 g/d as estimated by a baseline dietary questionnaire. Women subjects who were pregnant, planned to become pregnant, or received an unstable dose of hormone replacement therapy were also excluded from the study.

Thirty-four subjects qualified to participate after the initial lipid screen. Seven subjects were hypertensive and had been receiving treatment for at least 6 months prior to randomization. Two subjects were taking ACE inhibitors, two-beta-blockers, one subject was on a diuretic, another subject received both a beta-blocker and a diuretic, and another subject was on a combination of an ACE inhibitor, a calcium channel blocker and a diuretic. Results of a routine biochemical panel were normal for all subjects. The study protocol specified that subjects maintain their baseline body weight and exercise habits, as well as comply with the Step I diet throughout the study.

Experimental Treatment

All subjects followed the AHA Step I Diet during the dietary adaptation period and throughout the study. This diet provides <30% of energy as fat, <10% of energy as saturated fatty acids, 55% of energy as carbohydrate, 15% of energy as protein and <300 milligram (mg) cholesterol daily. During the intervention period, subjects in the HRC group received weekly supplies of a low-energy fruit-flavored beverage (sold under the trade designator FIERCE MELON GATORADE, Quaker Oats Company, Chicago, Ill.), providing about 2.5 g of HRC, as described above, per 240 mL of the beverage. The beverage also included 50 kcal of total calories, 14 g carbohydrate, 0 g fat and protein, 110 mg sodium and 30 mg potassium per serving. Subjects in the control group received the same serving sizes of beverage that did not contain the HRC. All subjects were instructed to drink one serving (240-mL) of the beverage twice daily before, with or after their two largest meals of the day for 6 weeks. Subjects recorded time and amount of the beverage consumed on daily calendars throughout the study. Compliance was assessed by review of these calendars at each follow-up visit and by counting unopened serving cups at the end of the study. Blinding of the subjects was deemed successful as judged by an informal interview at the end of the study.

Study and Analytical Procedures

Blood for a complete blood chemistry panel was drawn on the first visit and analyzed commercially (Quest Diagnostics Inc., Wood Dale, Ill.) to assess the overall health of all subjects. Duplicate serum samples for determining baseline lipid concentrations were collected during visits 1 and 2. End-of-study duplicate lipid samples were obtained six weeks later, on visits 8 and 9. All blood draws occurred after subjects had been fasting for 12 to 16 hours and samples were collected in standard serum separator tubes. They were then refrigerated and analyzed within 24 hours by a commercial laboratory certified to meet NCEP (National Choleterol Education Program) performance criteria (Quest Diagnostics Inc., Wood Dale, Ill.). Serum lipid profiles, including total, high-density lipoprotein-cholesterol (HDL-cholesterol) and triacylglycerol concentrations were measured enzymatically, using an Olympus AU5200 instrument (Olympus America Inc., Melville, N.Y.). LDL-cholesterol concentrations were calculated from total and HDL-cholesterol concentrations by using the Friedewald equation (Friedewald et al., *Clin. Chem.*, 18, 499 (1972)).

Blood pressure was also measured in duplicate both at baseline (visits 1 and 2) and after the completion of the intervention period (visits 8 and 9). Additionally, weekly blood pressure measurements were taken during intervention visits 3 through 7, at approximately the same time of the day. Readings from subjects taking hypertensive medication were obtained approximately 24 hours following last medication dose. Measurements were obtained after subjects had rested quietly in the seated position for at least five minutes in an examination room and prior to blood draws on sample collection visits. All readings were taken on the right arm, using an automated sphygmomanometer device (Press-Mate 8800, Collin Medical Instruments Corp., San Antonio, Tex.). Cuff size was used consistently within subjects. Measurements were repeated four times in two-minute intervals. The mean of all four readings was calculated and used in subsequent analyses.

Weekly body weight measurements without shoes were taken on an electronic scale (Scale-Tronix model 5005 Stand-On-Scale). Height was measured in the beginning of the study for verification of the subjects' BMI using a wall-mounted stadiometer.

Subjects were asked not to change their habitual levels of physical activity during the study. All subjects completed lifestyle questionnaires before and after the intervention, answering questions about their smoking habits and rating their exercise frequency on a 4-point scale with 1 being "never", 2="rarely", 3="once or twice weekly" and 4="three or more times per week." The selected number was used to calculate an average exercise frequency score for each group at baseline and study end. Additionally, the percent of subjects who exercised at least once weekly (exercise status) was calculated for within and between group comparisons.

Adverse events related to the HRC used in the present invention, non-study medication use and overall health changes were solicited by open-ended questions at each weekly clinic visit during the six-week intervention period. Moreover, subjects completed a side-effect questionnaire at baseline and study end, rating the occurrence and frequency of eleven gastrointestinal symptoms on a hierarchical 5-point scale from 0 (none) to 4 (extremely), with 2 being "moderately." A side effect score could be calculated from the questionnaire as a multiple of the number and frequency of side effects and could be between zero and 44.

To assess changes in dietary intake, three 3-day food records (2 weekdays and 1 weekend) were collected from all subjects at baseline (visit 2), end of week 3 (visit 5), and after the last week of intervention (visit 9). All food records were reviewed for completeness and analyzed using the Nutrition Data System for Research, version 4.02, database 30 (Nutrition Coordinating Center, University of Minnesota, Minneapolis, Minn.). For each record the average intake of total energy, the percent energy from total, saturated, monounsaturated and polyunsaturated fat, carbohydrate, protein and alcohol; the intake of total and soluble fiber, cholesterol, total trans fatty acids, the ratio of polyunsaturated to saturated fat, as well as the intake of sodium, potassium, calcium and magnesium were calculated. The average of all these variables for each of the three 3-day food records was calculated for each individual and used in subsequent statistical analyses. The approximately 5 grams (g) of fiber that each of the subjects in the HRC group consumed daily with their treatment beverages were not entered as part of subjects' dietary intake due to lack of an appropriate fiber substitute and a desire to monitor only "background" diet.

Data Analysis

All data are presented as mean±standard deviation (SD) unless otherwise stated and significance was defined as $P \leq 0.05$. A change (final value minus baseline value) in LDL-cholesterol at week 6 compared to baseline was the primary efficacy variable. Baseline data and mean change scores (end minus baseline) between the two groups for all continuous study parameters were compared using Student's t test for unpaired data. Within group differences from baseline to end were also assessed using paired t tests. A Chi-square test was used to determine if the frequency of smoking and exercise, exercise status, or side effect incidence differed by treatment group. A second comparison of treatments used a linear regression to adjust for baseline differences in age, BMI, lipids, as well as baseline dietary intakes of total fat, saturated fat, total dietary fiber and soluble fiber. Changes in dietary data within and between treatments were made based on comparisons of data for weeks 0, 3 and 6 using repeated measures analysis of variance (ANOVA). Data from thirty-two subjects of the 34 subjects were assessed on an intent-to-treat basis. All analyses were performed using The SAS System for Windows, release 6.12 (SAS Institute Inc., Cary, N.C.).

Results

Subject Characteristics

Thirty-three subjects completed the study. Of the thirty-four subjects who were randomized, one subject from the HRC group dropped out of the study after the third week of intervention for personal reasons. After the end of the study a review of the plasma fasting and postprandial glucose concentrations revealed that a subject in the HRC group had non-insulin dependent diabetes mellitus (an exclusion criteria) based on current American Diabetes Association criteria (The Expert Committee on the Diagnosis and Classification of Diabetes Mellitus, *Diab. Care,* 20, 1183 (1997)). Both of these individuals were excluded from the data analysis. Two other subjects (one in the HRC, the other in the control group) had very high concentrations of plasma total and LDL-cholesterol at baseline (9.9/7.6 mmol/L and 8.9/6.3 mmol/L, respectively). Analysis of the lipid data after exclusion of these two individuals however did not change the conclusions.

Compliance to the research protocol was excellent, with subjects in both groups consuming 97% of their beverages on the average.

Baseline characteristics of the sixteen subjects in each of the groups are summarized in Table 1. The groups were well matched for most demographic and lifestyle characteristics, with subjects in the control group being slightly but not significantly older compared to subjects in the HRC group (P=0.08). Ninety-one percent of all participants were of Caucasian heritage and 59.4% were women. The average body weight in either group did not change significantly during the study and the groups remained comparable at study end (HRC group, 80.2±17.0 kg; control group 76.6±13.7 kg). Additionally, subjects in both groups maintained their exercise status and frequency, as well as smoking habits and did not differ significantly from each other in any of these variables at baseline or at week 6.

TABLE 1

Baseline demographic and lifestyle characteristics[1,2]

| | HRC[3] (n = 7 M, 9 F) | CONTROL (n = 6 M, 10 F) |
|---|---|---|
| Age (years) | 41.2 ± 12 | 48.1 ± 9.6 |
| BMI (kg/m$^2$) | 27.7 ± 4.6 | 26.7 ± 3.7 |
| Weight (kg) | 79.9 ± 16.8 | 76.5 ± 13.3 |
| Soluble fiber intake (g/d) | 3.9 ± 1.1 | 4.2 ± 1.4 |
| Smoking habits (% smokers) | 12.5 | 18.8 |
| Exercise frequency score[4] | 3.3 ± 0.8 | 3.1 ± 0.9 |
| Exercise status (% exercising ≥ once weekly) | 81.3 | 81.3 |
| Systolic Blood Pressure (mm Hg) | 124.2 ± 11.4 | 122.2 ± 11.1 |
| Diastolic Blood Pressure (mm Hg) | 73.3 ± 7.7 | 73.2 ± 8.3 |

[1]Mean ± SD.
[2]No significant differences at $P \leq 0.05$.
[3]HRC = highly refined cellulose.
[4]Exercise frequency score was determined from subject responses on a four-point frequency scale as described above.

Dietary Data

Baseline, mid-study and week 6 dietary intakes of both groups are reported in Table 2. Both groups were compliant with AHA Step I diet guidelines. There were no significant within-group changes in any of the macronutrient intakes from baseline to study end. At baseline the HRC group had a significantly lower energy intake (P=0.02) (total calories from food and beverage), total fat intake (dietary lipid) (P=0.004) including lower saturated (P=0.002), monounsaturated (P=0.01) and total trans fat intake (P=0.05), and a higher polyunsaturated to saturated fat ratio (P=0.03). However, the difference in energy intake between the groups disappeared by the end of the study. Both groups, despite the difference at baseline, maintained their energy intake throughout the study.

The HRC group had a significantly lower intake of total fat as percent of energy at baseline, compared to the control group (P=0.004) and at study end (P=0.01). Identical pattern describes the changes in the percent of energy from saturated and monounsaturated fat intake. The differences between the groups in P:S ratio and total trans fat intake seen at baseline disappeared during the rest of the study. The control group experienced a significant drop in total cholesterol intake from beginning to study end (P=0.05), but a trend of a slightly lower cholesterol intake at each assessment point was characteristic of both groups. There were no differences in the percent energy from polyunsaturated fat or alcohol between the groups.

The HRC group had a significantly lower total and soluble dietary fiber intake at week 3 (P=0.001), but intakes at baseline and study end were similar between the groups. The control group experienced a significant decrease in calcium intake from baseline to week 6 (P=0.03). Total potassium intake in the HRC group dropped significantly at week 3, compared to the group's baseline intake (P=0.02) and to the control group's potassium intake (P=0.03).

TABLE 2

Selected daily dietary intakes[1]

| | HR CELLULOSE (n = 16) | | | CONTROL (n = 16) | | |
|---|---|---|---|---|---|---|
| | Baseline | Week 3 | Week 6 | Baseline | Week 3 | Week 6 |
| Energy | | | | | | |
| (MJ) | 6.94 ± 2.1* | 7.05 ± 1.9* | 7.41 ± 1.5 | 8.02 ± 2.4*[a b] | 8.06 ± 2.0*[b] | 7.2 ± 2.0[a] |
| (kcal) | 1659 ± 507* | 1684 ± 465* | 1771 ± 355 | 1916 ± 575*[a b] | 1925 ± 482*[b] | 1722 ± 488[a] |
| Protein (% of total energy) | 17.4 ± 4.3 | 16.3 ± 3.6 | 16.0 ± 4.2 | 15.7 ± 3.0 | 15.2 ± 3.8 | 15.1 ± 2.3 |
| Carbohydrate (% of total energy) | 58.4 ± 9.9 | 59.3 ± 8.7 | 60.7 ± 10.9 | 54.0 ± 7.8 | 57.8 ± 9.9 | 56.8 ± 7.4 |
| Total dietary fiber (g) | 18.4 ± 6.6 | 15.6 ± 6.7** | 16.9 ± 5.1 | 18.4 ± 6.8 | 21.3 ± 6.6** | 18.4 ± 8.1 |
| Soluble dietary fiber (g) | 6.3 ± 2.2 | 5.3 ± 2.1** | 5.5 ± 1.8 | 6.9 ± 2.4 | 7.3 ± 2.3** | 6.5 ± 2.8 |
| Fat (% of total energy) | 25.0 ± 7.2** | 24.7 ± 7.4 | 23.6 ± 8.6** | 30.7 ± 7.4** | 27.5 ± 8.8 | 28.4 ± 6.5** |
| Total cholesterol (mg) | 180 ± 138 | 172 ± 83 | 169 ± 97 | 208 ± 105[a] | 197 ± 111[a,b] | 151 ± 72[b] |
| Saturated fat (% of total energy) | 8.0 ± 2.5** | 7.9 ± 2.4 | 7.7 ± 3.2** | 10.5 ± 3.5** | 9.1 ± 3.5 | 9.8 ± 3.1** |
| Monounsaturated fat (% of total energy) | 9.1 ± 2.8** | 9.1 ± 3.5 | 8.4 ± 3.4** | 11.5 ± 3.5** | 10.2 ± 3.4 | 10.7 ± 2.8** |
| Polyunsaturated fat (% of total energy) | 5.7 ± 2.5 | 5.4 ± 2.3 | 5.4 ± 3.2 | 6.3 ± 2.5 | 5.8 ± 2.3 | 5.5 ± 1.6 |
| P:S | 0.89 ± 0.4* | 0.74 ± 0.3 | 0.78 ± 0.4 | 0.69 ± 0.4* | 0.80 ± 0.5 | 0.69 ± 0.3 |
| Total trans fat (g) | 2.5 ± 1.5* | 2.9 ± 2.2 | 2.9 ± 1.9 | 3.7 ± 1.8* | 3.3 ± 1.7 | 3.0 ± 2.0 |
| Alcohol (% of total energy) | 0.9 ± 1.5 | 1.3 ± 2.6 | 1.4 ± 2.4 | 1.6 ± 2.2 | 1.6 ± 2.6 | 1.8 ± 2.4 |
| Calcium (mg) | 798 ± 409 | 705 ± 342 | 829 ± 345 | 944 ± 322[a] | 741 ± 327[b] | 769 ± 342[b] |
| Magnesium (mg) | 284 ± 82.3 | 257 ± 91.9** | 275 ± 67.4 | 296 ± 80.9 | 312 ± 63** | 280 ± 70.2 |
| Sodium (mg) | 2989 ± 1236 | 2890 ± 1107 | 3132 ± 869 | 3125 ± 868 | 3188 ± 686 | 2878 ± 807 |
| Potassium (mg) | 2930 ± 1095[a] | 2470 ± 1002*[b] | 2737 ± 766[a,b] | 2941 ± 761 | 2918 ± 743* | 2586 ± 596 |

[1]Mean ± SEM. Baseline, week 3 and 6 values are based on 3-day foods. The HRC fiber was not included in the total and soluble fiber averages. Values in the same row with different superscript letters are significantly different within group, P ≤ 0.05.
*P ≤ 0.05 for between group comparison at respective time point.
**P ≤ 0.01 for between group comparisons at respective time points Effects of HRC on Lipids The two groups had comparable baseline lipid concentrations as shown in Table 3. Changes in serum lipids are also shown in Table 3. During the intervention period subjects in the HRC group had significantly lower total and HDL-cholesterol concentrations at the end of the study as compared to baseline (P=0.01 and P=0.05, respectively).

TABLE 3

Serum lipid concentrations and responses[1, 2]

| | HR CELLULOSE (n = 16) | | | CONTROL (n = 16) | | |
|---|---|---|---|---|---|---|
| | Baseline | End | Change | Baseline | End | Change |
| Total cholesterol[3] | | | | | | |
| (mmol/L) | 6.42 ± 1.01[a] | 6.07 ± 1.05[b] | −0.35 ± 0.5 | 6.44 ± 0.93 | 6.28 ± 0.95 | −0.16 ± 0.6 |
| (mg/dL) | 248.2 ± 38.9[a] | 234.7 ± 40.6[b] | −13.5 ± 19.2 | 249.2 ± 36.1 | 243.0 ± 36.6 | −6.2 ± 21.2 |

TABLE 3-continued

| | Serum lipid concentrations and responses[1, 2] | | | | | |
|---|---|---|---|---|---|---|
| | HR CELLULOSE (n = 16) | | | CONTROL (n = 16) | | |
| | Baseline | End | Change | Baseline | End | Change |
| LDL-cholesterol[3] | | | | | | |
| (mmol/L) | 4.29 ± 1.05 | 4.07 ± 1.12 | −0.22 ± 0.5 | 4.23 ± 0.75 | 4.07 ± 0.69 | −0.16 ± 0.5 |
| (mg/dL) | 165.7 ± 40.7 | 157.2 ± 43.4 | −8.5 ± 18.9 | 163.5 ± 28.9 | 157.4 ± 26.8 | −6.1 ± 17.7 |
| HDL-cholesterol[3] | | | | | | |
| (mmol/L) | 1.31 ± 0.34[a] | 1.22 ± 0.28[b] | −0.09 ± 0.2 | 1.45 ± 0.27 | 1.39 ± 0.3 | −0.05 ± 0.1 |
| (mg/dL) | 50.7 ± 13.0[a] | 47.2 ± 11.0[b] | −3.5 ± 6.4 | 55.9 ± 10.5 | 53.9 ± 11.7 | −2 ± 5.3 |
| Triacylglycerol[3] | | | | | | |
| (mmol/L) | 1.83 ± 0.91 | 1.71 ± 0.77 | −0.12 ± 0.5 | 1.68 ± 0.93 | 1.85 ± 1.21 | 0.17 ± 0.5 |
| (mg/dL) | 162.3 ± 80.4 | 151.8 ± 68.3 | −10.5 ± 43.9 | 148.9 ± 82.4 | 164.1 ± 107.1 | 15.1 ± 41.7 |
| Total:HDL-cholesterol[3] | 5.2 ± 1.4 | 5.2 ± 1.5 | 0.06 ± 0.5 | 4.6 ± 1.0 | 4.7 ± 1.0 | 0.07 ± 0.3 |

[1]Mean ± SD. No significant differences between groups at $P \leq 0.05$.
[2]Values in the same row with different superscript letters are significantly different within group, $P \leq 0.05$
[3]Baseline and end concentrations represent the average of values taken at visits 1 and 2 (during the week preceding intervention) and visits 8 and 9 (week following the 6-week intervention).

On the average, mean serum LDL-cholesterol decreased by 5.1% in the HRC group and 3.7% in the group receiving the control treatment. Similarly total cholesterol concentrations decreased 5.4% in the HRC group and 2.5% in the control group. The HRC group experienced a 6.5% drop in triacylglycerol, whereas on the average, a 10% increase in triacylglycerol concentration was noted in the control group from baseline to study end. The average concentration of HDL-cholesterol was lower after 6 weeks of intervention in both groups, but the change was not significantly different between the groups (P=0.50). The reduction in HDL-cholesterol resulted in a corresponding slight increase in the ratio of total to HDL-cholesterol in both groups. Adjustment for baseline lipid concentrations, gender, or exercise did not change any of the conclusions above. Furthermore, an analysis of covariance showed no age-gender interaction with regards to lipid changes in the two treatment groups.

The influence of age was assessed by comparing the lipid responses in younger (age 19-30) and older (age 55-75) subjects. Younger subjects in the control group had a significantly greater total cholesterol reduction than did younger subjects in the HRC group (P=0.043). The influence of hypertension on lipid response was also assessed by an ANOVA. Treated hypertensive individuals in the HRC group experienced a significantly greater reduction in triacylglycerol compared to treated hypertensives in the control group (P 0.0007).

Lastly, subjects with a BMI in the healthy range (<25) tended to have a greater reduction in total cholesterol, followed by overweight (25<BMI<30) and obese (BMI>30) individuals.

Adjusting the lipid changes for baseline dietary intakes of total fat, saturated fat, total dietary fiber and soluble fiber also did not show any significant effect of these variables. Analysis of HRC beverage consumption data in the HRC group showed no significant effect of the time of beverage consumption on the change in any of the lipid concentrations measured.

Finally, within the HRC group, the characteristics of responders (defined as subjects experiencing a drop in LDL-cholesterol greater than 0.15 mmol/L, or 5.9 mg/dL) and non-responders were compared. Responders were more likely to exercise at least twice per week (P=0.13), had a significantly higher exercise level at baseline (P=0.05) and study end (P=0.02), had slightly lower triacylglycerol concentrations (P=0.21), were normotensive (P=0.06, although there were only 3 hypertensives in the HRC group), and had twice the intake of dietary cholesterol (P=0.09), compared to non-responders. Furthermore, subjects who were obese (BMI>30) were more likely to be non-responders (P=0.11).

Effects of HRC on Blood Pressure

Blood pressure data are shown in Table 4. The HRC group experienced slightly greater decreases in both systolic and diastolic blood pressure, compared to the control group (2.3% and 1.8% versus 1.6% and 1.5%, respectively). Analysis of data from a subset of the six hypertensive subjects who completed the study and were evenly distributed in each group, showed a greater benefit from HRC on systolic blood pressure in that subset (6.1% decrease in the HRC group versus 1.5% in the control group) (P=0.13). Adjustment for dietary intake of calcium, magnesium, sodium, potassium and percent energy from fat did not change any of the above results. Analysis of HRC beverage consumption data in the HRC group showed that subjects who consumed a greater percent of their beverages within 30 min after a meal, as opposed to before or with (during) a meal, experienced a somewhat greater lowering of both their systolic and diastolic blood pressure (P=0.11 and P=0.07, respectively).

TABLE 4

| | Blood pressure responses[1, 2] | | | | | |
|---|---|---|---|---|---|---|
| | HR CELLULOSE (n = 16) | | | CONTROL (n = 16) | | |
| | Baseline | End | Change | Baseline | End | Change |
| Systolic blood pressure[3] (mm Hg) | 124.3 ± 11.4 | 121.5 ± 10.0 | −2.8 ± 7.9 | 122.2 ± 11.1 | 120.3 ± 11.6 | −1.9 ± 5.0 |

TABLE 4-continued

Blood pressure responses[1, 2]

| | HR CELLULOSE (n = 16) | | | CONTROL (n = 16) | | |
|---|---|---|---|---|---|---|
| | Baseline | End | Change | Baseline | End | Change |
| Diastolic blood pressure[3] (mm Hg) | 73.3 ± 7.7 | 71.9 ± 6.6 | −1.3 ± 5.4 | 73.2 ± 8.3 | 72.1 ± 9.7 | −1.1 ± 4.2 |

[1]Mean ± SD.
[2]No significant differences between and within groups at $P \leq 0.05$.
[3]Baseline values represent an average of readings taken at visits 1 and 2 (during week prior to intervention start); end values represent an average of readings taken at visits 8 and 9 (during week following 6-week intervention.

Side Effects

About 81% of subjects in the HRC group and 75% of subjects in the control group reported at least one of the eleven gastrointestinal side effects on the baseline side effect questionnaire. The eleven gastrointestinal side effects include diarrhea, loose stools, constipation, stomach pain, nausea or vomiting, heartburn, gas, loss of appetite, feeling of fullness in stomach, indigestion, bloating. Both the frequency and number of side effects experienced during, and reported after the intervention decreased slightly in both groups by similar amounts. At the end of the intervention, 75% of subjects in the HRC group and 56% of subjects in the control group reported having experienced at least one of the eleven side effects, a non-significant difference. Subjects in the HRC group reported twice the number and frequency of side effects as subjects in the control group, but the mean number was 2.8 (out of 11) and the mean side effect score only 4.1 (out of 44) ($P=0.14$ and $P=0.17$, respectively).

Subjects in the HRC group reported greater number of side effects related to the lower gastrointestinal tract (e.g. flatulence) and to satiety (e.g. feeling of fullness in the stomach). The differences, however, were not statistically significant.

No serious adverse effects related to treatment were reported in either group during any of the five visits throughout the 6-week intervention.

Subjects in the HRC group experienced a greater reduction of total and LDL-cholesterol, triacylglycerol as well as systolic blood pressure compared to the control group (FIG. 1). The net percent reductions of these outcome variables in the HRC group were 2.9%, 1.4%, 16.5% for the respective lipids and 0.7% for blood pressure.

Surprisingly, the magnitude of the lipid reductions noted in the HRC group in this study was similar to what studies of oat products using comparable amounts of soluble fiber along with a Step I diet have reported (VanHorn et al., *J. Am. Diet Assoc.*, 86, 759 (1986); VanHorn et al., *Prev. Med.*, 17, 377 (1988); Davidson et al., *JAMA*, 265, 1833 (1991)).

There was a decrease in blood pressure in the HRC group. Furthermore, the possibility of a differential ability of fiber to lower blood pressure in hypertensive individuals was investigated by analysis of a hypertensive subgroup (n=6). A net reduction of 4.6% in systolic and 1.7% in diastolic blood pressure was detected in those hypertensives that were in the HRC group. The decrease was greater than that seen in the complete sample (i.e., the 32 subjects) (0.7% and 0.3%). Statistical analyses in this study showed that the two groups were not comparable with regards to total energy intake, percent energy from total, saturated and monounsaturated fat, total trans fat, as well as total and soluble dietary fiber. These differences existed despite the fact that both groups fell within desirable ranges for all macronutrients and total cholesterol as instructed according to the AHA Step I diet. It is likely that the differences in these dietary components between the groups at baseline, week 3 and study end was responsible for the inability to separate the effect of HRC from that of background diet. The control group had a higher mean energy intake at baseline, but by the end of the study it had dropped by about 10% while the HRC group had a 6.7% increase in energy intake. It should be noted that the energy intake reported by subjects in both groups was low, possibly suggesting an underreporting of food intake. Given the significant difference in energy intake between the groups at baseline and week 3 of the study, it is difficult to know whether the reporting bias was similar in both groups.

The contribution of total fat intake to overall energy was higher in the control group at baseline by 5.7% and this significant difference persisted until the end of intervention. Both groups reported a decreasing percent of energy from total fat throughout the study but the change was greater in the control group than in the HRC group (7.5% versus 5.6%). The same was true of the percent of energy from saturated fat (6.7% versus 3.8%). As could be expected, the total cholesterol intake, which was not significantly different between the groups at baseline or study end, also declined from week 1 to week 6. This decline was once again greater in the control group than in the HRC group (27.4% versus 6.5%).

From baseline to week 6, the HRC group also had a 16% increase in the intake of total trans fat, while the control group decreased their trans fat intake by 19%. Using the Keys equation it was calculated that the changes in fat and cholesterol intake between baseline and week 6 of intervention seen in the control group would result in a 0.2 mmol/L (7.7 mg/dL) drop in serum total cholesterol (0.18 mmol/L/6.9 mg/dL from baseline to week 3 and 0.09 mmol/L/3.4 mg/dL from week 3 to week 6) (Keys et al., *Metabolism*, 14, 776 (1965)). The equation predicted reductions in serum cholesterol in the HRC group as well, but of smaller magnitude (0.15 mmol/L/5.9 mg/dL from baseline to week 6, 0.1 mmol/L/3.7 mg/dL from baseline to week 3 and 0.12 mmol/L/4.6 mg/dL from week 3 to week 6). Given the actual changes in lipid concentrations that the groups experienced from baseline to week 6, it may be estimated that the difference in serum cholesterol reduction between the groups, not attributable to the background dietary changes would be about 0.24 mmol/L (9.1 mg/dL). This raises the possibility that had subjects been fully compliant with the request not to modify their diets during the study, the lipid changes observed in the groups may have been significantly different.

Individuals in the HRC group decreased both their total and soluble fiber intakes by 8.2% and 13.9%, respectively. This may have been an unconscious attempt to compensate for the 5 g of HRC added daily during the intervention.

The control group, on the other hand, had no overall change in total fiber intake from baseline to week 6, but a non-significant 15.8% increase was noted at week 3 (P=0.08). Overall, the control group showed a 5.8% decline in soluble fiber.

In summary, these data are the first to assess the hypolipidemic and hypotensive effects of the HRC as used in the present invention in humans. Consumption of about 5 g of the HRC daily results in moderate reductions in total and LDL-cholesterol, triacylglycerol and blood pressure. It can be estimated that the 2.9% net reduction that the HRC group experienced can result in a 6-9% reduction of cardiovascular disease risk in people with hypercholesterolemia (Lipid Research Clinics Program, *JAMA,* 251, 365 (1984)). Similarly, the blood pressure changes observed may be of value in the treatment and prevention of hypertension and other cardiovascular conditions.

Example II

Effect of HRC on Measures of Insulin Sensitivity and Glucose Tolerance

Materials And Methods
Subjects
The subjects were the same as those described in Example I.
Study Design
A double blind, placebo-controlled, parallel-arm study design was used. The trial involved two frequently sampled intravenous glucose tolerance tests (FSIGT; Yang et al., *Am. J. Physiol.,* 253, E595 (1987)), one at baseline and another following the six-week intervention period.

After the initial lipid screen to confirm eligibility, subjects were seen once before the start of intervention (visits 1), once weekly during the intervention (visits 2-6) and once on the day following the last day of intervention (visit 7). At visit 1 all subjects underwent an FSIGT. Subjects were then randomly assigned to the active treatment (HRC group) or control group using a fixed allocation randomization scheme with permuted blocks of four and six. During the next 6 weeks, subjects in the HRC group received 2.5 g of HRC twice daily for 6 weeks, whereas subjects in the control group did not. All subjects were free-living and followed the AHA Step I diet. At the end of the 6-week intervention (visit 7), subjects underwent another FSIGT.
Experimental Treatment
The Experimental Treatment was similar to that described in Example I, above.
Frequently Sampled Intravenous Glucose Tolerance Test (FSIGT)
Subjects fasted for 12-16 hours before both FSIGTs. A serum pregnancy test was performed on all female subjects prior to testing. With the subject recumbent, an intravenous saline lock catheter was placed in the antecubital vein of each arm. One of the catheters was used for blood sampling, and the other for the glucose and Tolbutamide injections. Baseline glucose and insulin samples were obtained 30, 20, 10, and 5 minutes prior to injection of glucose. The mean of these samples for each subject was used for the fasting glucose and insulin analyses. A bolus injection of 0.3 g/kg 50% (wt/vol) dextrose (glucose) solution was then initiated and was infused over 1 min, with 0-time being the mid-point of the bolus.

Further blood samples were taken at 2, 3, 4, 5, 6, 8, 10, 12, 14, 16, and 19 minutes after injection. At t=20 min, an injection of Tolbutamide solution (Orinase Diagnostic®, Pharmacia & Upjohn Company, Kalamazoo, Mich.) was administered intravenously over 30 seconds at a dose of 300 mg if BMI was less than 30 and 500 mg if BMI was greater than or equal to 30. The Tolbutamide causes additional endogenous insulin secretion beyond that of glucose alone, which enhances the ability of a computer program to estimate the model parameters (Yang et al., *Am. J. Physiol.,* 253, E595-E602 (1987)). Subsequent blood samples for glucose and insulin were drawn at 22, 24, 25, 27, 30, 40, 50, 60, 70, 90, 100, 120, 140, 160, 180, 190, 200, 210, 220, 230, and 240 minutes. During the testing period, subjects refrained from food intake but had free access to water.

Bergman's minimal model technique was used for determination of glucose effectiveness ($S_G$), insulin sensitivity ($S_I$) and acute insulin response to glucose (AIRg) (Bergman et al., *Am. J. Physiol.,* 236, E667-E677 (1979))). The exact time of each sample along with the values of glucose and insulin concentrations from the FSIGT were submitted to a program for parameter calculation (MINMOD, version 3.0, G M Steil and R N Bergman, University of Southern California) (Pacini and Bergman, *Comput. Methods Programs Biomed.,* 23, 113-122 (1986)). The program is based on a mathematical model that uses the glucose and insulin measurements to deduce in vivo insulin sensitivity (Pacini et al., Computer Modeling for Quantitative Assessment of Metabolic States. In: Lindberg et al., eds. Proceedings AAMSI Congress 83. Bethesda: AAMSI Publications, 170-4 (1983); Bergman et al., *Endocr. Rev.,* 6, 45 (1985)).

Glucose effectiveness represents the efficiency by which glucose can restore its own concentration independent of insulin response, while the insulin sensitivity index represents the increase in glucose clearance per unit increase in plasma insulin concentration. Higher $S_I$ values indicate greater sensitivity to insulin and the $S_I$ parameter is highly correlated with insulin sensitivity as assessed by the clamp method (Saad et al., *Diabetes,* 43, 1114-21). The acute insulin response to the intravenous glucose (AIRg) represents the first phase insulin response and was calculated by the computer program as the increment of plasma insulin above the basal concentrations from 0 to 10 minutes, following the glucose bolus (Lerner et al., *J. Clin. Endocrinol. Metab.,* 33, 409 (1971)). Finally, the relationship between acute insulin response and insulin sensitivity has been determined to be hyperbolic, allowing the use of the insulin sensitivity-secretion product (the "disposal index") (Bergman et al., *J. Clin. Invest.,* 68, 1456 (1981); Bergman et al., *Diabetes,* 38, 1512 (1989); Kahn, *Diabetes,* 42, 1663 (1993)) to be used in the assessment of β-cell compensation for insulin resistance. The disposal index (DI) was calculated in this study as the product of $S_I$ and AIRg.

The average fractional standard deviations (FSD) of $S_I$ and $S_G$ were calculated by the MINMOD program to be 3.5% and 13.9%, respectively.
Study and Analytical Procedures
Study and Analytical procedures were similar to those in Example I, except as noted below.

Blood samples for glucose analysis were collected in lithium heparin-coated Vacutainer tubes (Becton Dickinson, Rutherford, N.J.), centrifuged at 4° C. (1800×g, 10 min) and refrigerated at 2° C. until assayed. Plasma glucose was determined using the glucose oxidase colorimetric method and a Vitros 950 Analyzer (Johnson and Johnson Clinical Diagnostics, Rochester, N.Y.).

Blood for insulin analysis was collected in serum Vacutainer tubes (Becton Dickinson, Rutherford, N.J.), promptly centrifuged at 4° C. (1800×g, 10 min), after which serum was aliquoted, and stored at −20° C. until assayed. Insulin was measured with a competitive double antibody radioimmunoassay with human proinsulin cross-reactivity less than 0.2% using a $^{125}$I-labeled human insulin (LINCO Research, Inc., St. Charles, Mo.). Radioactivity was counted in a Cobra II Auto-Gamma counter, model 5010 for 3 minutes (Packard Instruments, Downers Grove, Ill.). To reduce the effects of inter-assay variability, all samples from each subject were analyzed in duplicate in the same run, along with standardized controls. Intra-assay variability based on the counts was 1.9% and inter-assay variability was 12.9% and 5.6% for controls with low and high insulin concentration, respectively. A small number of insulin values were off the standard curve and were thus extrapolated by a third order polynomial regression using SigmaPlot 4.0 (SPSS, San Rafael, Calif.) and final concentrations calculated in Microsoft Excel 97.

Statistical Analyses

Statistical analyses are as described for Example I, above.

Results

Subject Characteristics

Subject characteristics are as described for Example I, above.

Dietary Data

Dietary data are as described for Example I, above.

Fasting Glucose and Fasting Insulin Responses

The two groups had comparable basal fasting glucose concentrations as can be noted in Table 5 (P=0.2). Basal fasting insulin was slightly lower in the control group at baseline (P=0.52). Changes in fasting glucose and insulin are also shown in Table 5. Mean fasting concentrations of glucose remained virtually unchanged from baseline to study end in both groups. The mean fasting insulin concentration in the HRC group increased slightly, but there was a large within-group variability (P=0.42). Adjusting the comparison of changes in basal glucose and insulin for baseline concentrations of fasting glucose, fasting insulin and hypertension, as well as for changes in blood pressure and serum lipids did not change the conclusions.

FSIGT Responses

There were significant differences in the AIRg between the groups at baseline (P=0.01). The HRC group, on the average, had more than double the mean response of the control group as can be seen in Table 5. However, there was a great within-group variability resulting in a large standard deviation. The AIRg in both groups remained largely unchanged from baseline to study end (P=0.89 for difference in change).

Figure 2A:
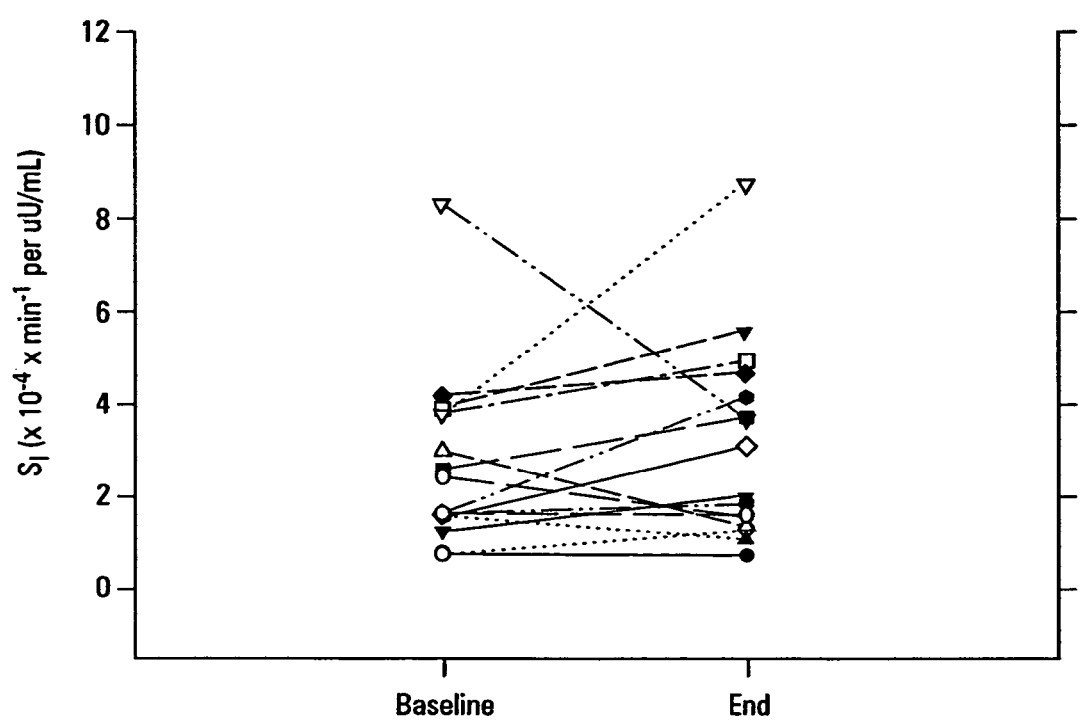
FIGS. 2A-B depict change in insulin sensitivity ($S_I$) from baseline to study end in individuals in the (A) actively treated (HRC) group (n=16) and (B) the control group (n=16).
Figure 2B:
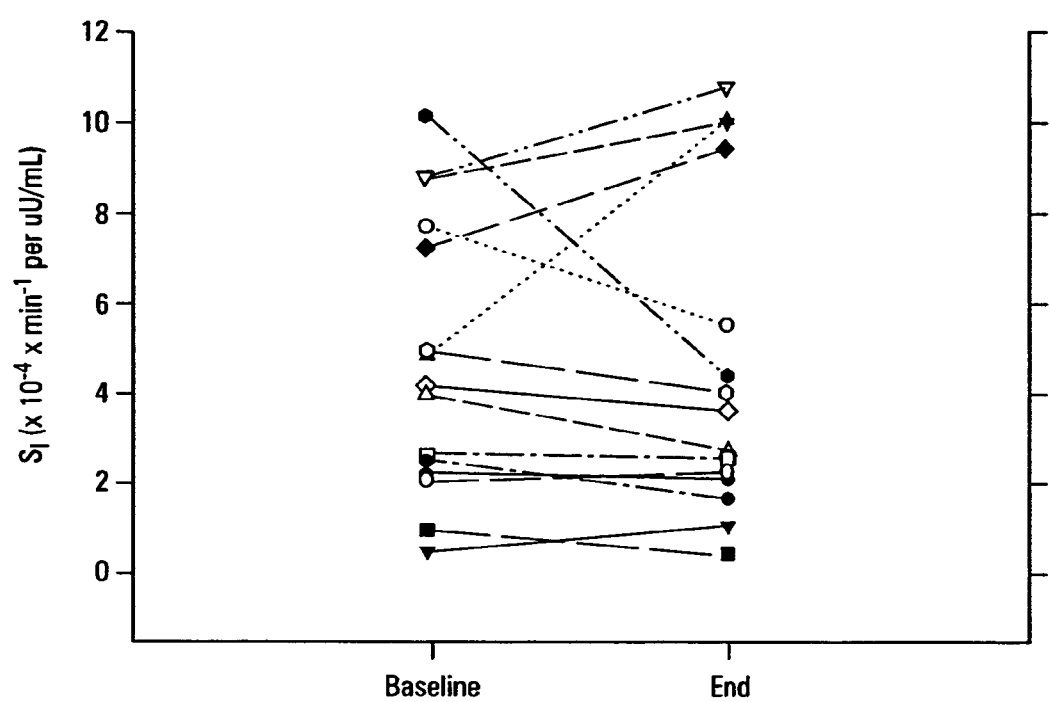

Glucose effectiveness ($S_G$) was almost identical between the groups at baseline and remained that way throughout the study. Unfortunately, there were between group differences in insulin sensitivity at baseline. On the average, subjects randomized to the control group were shown to have almost twice the insulin sensitivity of subjects in the HRC group (P=0.03). When comparing the mean changes between baseline and study end between the groups, $S_I$ in the HRC group slightly increased, whereas in the control group it remained the same. Individual responses are depicted in FIGS. 2A-B. This however, was a very small and statistically insignificant difference (P=0.55). Finally, the disposal indices calculated for the two groups, although comparable at baseline, remained unchanged in the control group by study end, but increased by 21.5% in the HRC group. The difference in this change was not significant (P=0.36), but again demonstrated a trend.

Adjusting the changes in AIRg, $S_I$, $S_G$ and DI from baseline to end for age category, gender, BMI, exercise category at baseline, basal fasting glucose, fasting insulin and hypertension status, as well as for changes in blood pressure and serum lipids did not yield treatment differences. Furthermore, adjustments for baseline dietary intakes of total energy, total cholesterol, percent energy from saturated, monounsaturated and polyunsaturated fat, total trans fat, total dietary fiber and total soluble fiber did not show any significant effects of these variables on the changes in FSIGT parameters from baseline to study end. Analysis of HRC beverage consumption data in the HRC group showed that subjects, who consumed a greater percent of their beverages within 30 min after a meal, as

TABLE 5

Results from FSIGT at baseline and study end[1]

| | HR CELLULOSE (n = 16) | | | CONTROL (n = 16) | | |
|---|---|---|---|---|---|---|
| | Baseline | End | Change | Baseline | End | Change |
| Insulin sensitivity | | | | | | |
| $S_I$ ($\times 10^{-5} \cdot min^{-1}$ per pmol/L) | 1.60 ± 1.1* | 1.87 ± 1.3 | 0.28 ± 1.2 | 2.88 ± 1.9* | 2.87 ± 2.2 | −0.01 ± 1.4 |
| ($\times 10^{-4} \cdot min^{-1}$ per µU/mL) | 2.66 ± 1.9* | 3.12 ± 2.1 | 0.46 ± 2.0 | 4.80 ± 3.1* | 4.78 ± 3.6 | −0.02 ± 2.4 |
| β-Cell function | | | | | | |
| Basal fasting insulin[2] | | | | | | |
| (pmol/L) | 64.8 ± 41.4 | 73.8 ± 49.8 | 9.0 ± 44.4 | 55.8 ± 33.0 | 61.8 ± 31.2 | 5.9 ± 10.8[a] |
| (µU/mL) | 10.8 ± 6.9 | 123 ± 8.3 | 1.5 ± 7.4 | 9.3 ± 5.5 | 10.3 ± 5.2 | 0.99 ± 1.8[a] |
| AIRg (pmol · min/L) | 1,933 ± 1,616** | 1,982 ± 1,408 | 47.9 ± 1,063 | 773 ± 364** | 809.7 ± 461 | 86.9 ± 219 |
| Glucose and glucose tolerance | | | | | | |
| Basal fasting glucose[2] | | | | | | |
| (mmol/L) | 4.9 ± 0.5 | 4.8 ± 0.5 | −0.9 ± 0.5 | 5.1 ± 0.7 | 5.1 ± 0.5 | −0.06 ± 0.4 |
| (mg/dL) | 87.5 ± 8.2 | 86.2 ± 8.7 | −1.3 ± 8.6 | 92.2 ± 11.7 | 91.1 ± 9.2 | −1.1 ± 6.4 |
| SG ($\times 10^2 \cdot min^{-1}$) | 1.78 ± 0.46 | 1.86 ± 0.43 | 0.08 ± 0.52 | 1.81 ± 0.36 | 1.85 ± 0.5 | 0.04 ± 0.5 |
| β-Cell compensation | | | | | | |
| DI (Si × AIRg) ($min^{-1}$) | 3,687 ± 2,135 | 4,482 ± 2,670 | 795 ± 2,699 | 3,006 ± 1,802 | 3,080 ± 2,222 | 74.7 ± 1,353 |

[1]Mean ± SD.
[2]Basal insulin and glucose values are the average of the fasting measurements during the FSIGT before dextrose injection.
*Denotes a significant difference between groups at P ≦ 0.05.
**Denotes a significant difference between groups at P ≦ 0.01.
[a]Denotes within-group significant differences P ≦ 0.05 opposed to before or with a meal, experienced a significantly lesser increase in insulin sensitivity (P=0.01).

Side Effects

The side effects are as described above in Example I, above.

Discussion

It has been suggested that in non-diabetic individuals significant changes in $S_I$ related to one's genetic make-up or environment may occur without accompanying changes in $S_G$ (Bergman, *Diabetes*, 38, 1512 (1989)). On the contrary, in an individual with type II diabetes a decline of $S_G$ may be pathogenic as defects in both $S_I$ and $S_G$ are observed in NIDDM (Bergman, *Diabetes*, 38, 1512 (1989)). Computer simulations have demonstrated that no single defect in $S_I$, $S_G$, or AIRg is sufficient to lead to glucose tolerance within the diabetic range, whereas combined defects appear highly synergistic (Bergman, *Diabetes*, 38, 1512 (1989)).

It is now fairly well accepted that there is a hyperbolic relationship between insulin sensitivity (action) and insulin secretion (β-cell function) (Kahn et al., *Diabetes*, 42, 1663 (1993)). A decrement in insulin sensitivity leads to a reciprocal compensatory increase in β-cell glucose sensitivity and secretion (responsiveness), such that glucose tolerance remains within a normal range (sensitivity× secretion=constant) (Bergman, Diabetes, 38, 1512 (1989)). The high AIRg values in the HRC group, along with the corresponding low $S_I$ values are consistent with this assertion. Because of this relationship, it is clear that knowing only insulin sensitivity would not be adequate to indicate whether a given individual is in good or impaired glucose tolerance; β-cell responsiveness must also be known. Conversely, if the product of these two parameters (disposal index) is known, it can serve as a predictor of diabetes risk. DI was calculated in the current study for individuals in both groups in an effort to address that question. Despite the lack of significant differences between the groups, there was a 21.5% increase in DI in the HRC group. An improvement in the sensitivity-secretion relationships of only 2.5% was observed in the control group (P=0.36).

Example III

Acute and Chronic Effects of HRC on Fasting and Postprandial Concentrations of Glucose and Cholecystokinin Materials and Methods Subjects The subjects are as described in Example I, above.

Study Design

The study design is as described in Example 1, above.

Test meals and Experimental Treatment

The test meals and experimental treatment are as described in Examples I and II, above, with the following exceptions.

The liquid test meal (502 g) administered on visits 1 and 8 consisted of a chocolate-flavored shake providing 500 kcal, 80 g carbohydrate, 12 g fat, 18 g protein and 50% of the reference daily intake (RDI) for 24 vitamins and minerals (sold under the trade designator ENSURE, Ross Product Division, Abbott Laboratories, Columbus, Ohio). The test meal consumed on visit 2 was identical to that on visits 1 and 8 but was co-homogenized with about 5 g of HRC and had a slightly larger volume to account for the addition of the fiber (529 g).

Study and Analytical Procedures

Study and analytical procedures were as described in Example I with the following exceptions.

Subjects fasted for 12-16 hours before all three meal-testing periods. An intravenous saline lock catheter was placed in the antecubital vein and a baseline (−5-min) blood sample was drawn for determination of insulin, glucose and cholecystokinin concentrations. The subjects then had 2 minutes to consume the test meal. A blood sample was drawn immediately at the completion of the drink (O-min) and additional samples were drawn at 10, 20, 30, 45, 60, 90, 120 and 180 min for cholecystokinin. Samples for measurement of plasma glucose concentration were drawn at 30, 60, 90, 120 and 180 min after the consumption of the meal. During the testing period, subjects refrained from food intake but had free access to water.

Blood for CCK analysis was collected in chilled EDTA-coated Vacutainer tubes (Becton Dickinson, Rutherford, N.J.) to which 0.385 TIU (500 KIU) of 0.9% NaCl and 0.9% benzyl alcohol solution of aprotinin (Sigma-Aldrich, Inc., St. Louis, Mo.) per mL of whole blood had been added with a disposable 1 mL syringe. Samples were kept on ice during collection, promptly centrifuged at 4° C. (1800×g, 10 min), plasma was aliquoted, flash frozen on dry ice and stored at −70° C. until assayed. Plasma samples for CCK determination underwent extraction with 95% ethanol and were evaporated using a Centrivap concentrator (Labconco, Kansas City, Mo.).

Extraction recovery was controlled for during each extraction and these control samples were assayed along with unknowns. Analysis was performed using a highly sensitive and specific competitive double antibody radioimmunoassay with cross-reactivity to gastrin <0.5%, using a $^{125}$I-labeled CCK-8 (Alpco Diagnostics, Windham, N.H.). Radioactivity was counted in a Cobra II Auto-Gamma counter, model 5010 for 3 minutes (Packard Instruments, Downers Grove, Ill.). To reduce the effects of inter-assay variability, all samples from each subject were analyzed in duplicate in the same run, along with standardized controls. Intra-assay variability based on the counts was 1.3% and inter-assay variability was 5.8% and 4.8% for controls with low and high CCK concentration, respectively. CCK values below the lowest standard of 0.195 pmol/L were arbitrarily assigned a value of 0.1 pmol/L before all sample concentrations were corrected for extraction recovery.

Statistical Analyses

The primary outcome measures were the changes in the glucose and CCK incremental area under the curve (AUC) responses, following the tests meals consumed at baseline, within three days of baseline, and at the end of the intervention. AUC data were converted to increments by subtracting baseline values from values at each time point and were calculated using the trapezoid rule (Matthews et al., *Br. Med. J.*, 300, 230 (1990)). Total area under the curve (tAUC) values for both glucose and CCK were also calculated from the series of time points without adjustment for baseline. Summary data from the acute postprandial study were analyzed by paired Student's t tests and those from the long-term study were compared by two-sample Student's t tests.

Peak glucose and peak CCK were selected as the first highest postprandial values during a testing period, immediately preceding a lower value. The change in average peak was also compared by paired and unpaired Student's t tests. The time to peak medians from the acute study were compared by Wilcoxon signed-rank test, while time to peak medians from the long-term study were analyzed using the Wilcoxon two-sample test.

The change in average CCK concentration at 180 min (last time point during a test meal) was also compared. Baseline data and mean change scores (end minus baseline) between the two groups and between sexes for all other continuous study parameters were compared using Student's t test for unpaired data. Within-group changes from baseline to end were also assessed using paired t tests. A Chi-square test was used to determine if gender distribution, the frequency of smoking and exercise, exercise status, or side effect incidence differed at baseline between the two treatment groups. Changes in dietary data within and between treatments were compared at weeks 0, 3 and 6 using repeated measures analysis of variance (ANOVA).

Data were analyzed on an intent-to-treat basis. All data are presented as mean±SD, unless otherwise stated and the probability level at which differences were considered significant was P≦0.05. All analyses were performed using SAS 6.12 (SAS Institute Inc., Cary, N.C.).

Results

Subject Characteristics

Thirty-four subjects underwent the first two test meals and were randomized. One of the subjects from the HRC group dropped out of the study after the third week of intervention for personal reasons. Data from this subject was included only in the analyses of the acute postprandial data, but not in the long-term study comparisons of change.

Thirty-three subjects completed the entire study. After the end of the study however, a review of the plasma fasting and postprandial glucose concentrations revealed that a subject in the HRC group had non-insulin dependent diabetes mellitus (an exclusion criteria) based on current American Diabetes Association criteria. Data from this individual were excluded from all analyses. Compliance to the research protocol was excellent, with subjects in both groups consuming 97% of their beverages on the average.

Baseline characteristics of the subjects participating in the initial acute study and those who underwent the longer-term study after randomization are summarized in Table 6. The two groups were well matched for most demographic and lifestyle characteristics, with subjects in the control group being slightly but not significantly older compared to subjects in the HRC group (P=0.08). On the average, subjects were normotensive, with six of them receiving hypertensive medication. Subjects were also moderately hypercholesterolemic as required by the study inclusion criteria.

Ninety-one percent of all subjects were of Caucasian heritage and 59.4% were women. The average body weight in either group did not change significantly during the study and the groups remained comparable at study end (HRC group, 80.2±17.0 kg; control group 76.6±13.7 kg). Additionally, subjects in both groups maintained their exercise status and frequency, as well as smoking habits, and did not differ significantly from each other in any of these lifestyle variables at baseline or at week 6.

TABLE 6

Baseline demographic and lifestyle characteristics[1]

| | Initial acute study | Long-term study of adaptive changes | |
|---|---|---|---|
| | ALL[2] (n = 14 M, 19 F) | HRC[3] (n = 7 M, 9 F) | CONTROL (n = 6 M, 10 F) |
| Age (years) | 44.4 ± 11.2 | 41.2 ± 12 | 48.1 ± 9.6 |
| BMI (kg/m$^2$) | 27.3 ± 4.1 | 27.7 ± 4.6 | 26.7 ± 3.7 |
| Weight (kg) | 78.7 ± 15.1 | 79.9 ± 16.8 | 76.5 ± 13.3 |
| Soluble fiber intake (g/d) | 4.0 ± 1.3 | 3.9 ± 1.1 | 4.2 ± 1.4 |
| Smoking habits (% smokers) | 18.2 | 12.5 | 18.8 |
| Exercise frequency score[4] | 3.1 ± 0.9 | 3.3 ± 0.8 | 3.1 ± 0.9 |
| Exercise status (% exercising ≧ once weekly) | 78.8 | 81.3 | 81.3 |
| SBP (mm Hg) | 122.9 ± 11.1 | 124.3 ± 11.4 | 122.2 ± 11.1 |
| DBP (mm Hg) | 72.8 ± 8.1 | 73.3 ± 7.7 | 73.2 ± 8.3 |
| Total cholesterol (mmol/L)[5] | 6.4 ± 0.9 | 6.4 ± 1.0 | 6.4 ± 0.9 |
| LDL-cholesterol (mmol/L)[5] | 4.3 ± 0.9 | 4.3 ± 1.1 | 4.2 ± 0.8 |
| HDL-cholesterol (mmol/L)[5] | 1.4 ± 0.3 | 1.3 ± 0.3 | 1.5 ± 0.3 |
| Triacylglycerol (mmol/L)[5] | 1.8 ± 0.9 | 1.8 ± 0.9 | 1.7 ± 0.9 |
| Insulin sensitivity ($\times 10^{-4} \cdot min^{-1}$ per pmol/L) | 3.65 ± 2.7 | 1.60 ± 1.1 | 2.88 ± 1.9 |
| Acute insulin response to glucose (pmol · min/L) | 1,346 ± 1,290 | 1,933 ± 1,616 | 773 ± 364 |

[1]Mean ± SD. No significant differences at P ≦ 0.05.
[2]One subject who participated in the initial acute study dropped out during intervention and is thus not included in any group analyses.
[3]HRC = highly refined cellulose.
[4]Exercise frequency score was determined from subject responses on a four-point frequency scale as described in the text.
[5]To convert values of cholesterol from mmol/L to mg/dL, multiply by 38.7; for triacylglycerol, multiply by 88.6.

Dietary Data

The dietary data is similar to that described in Example I, above.

Acute Postprandial Study

Figure 3:
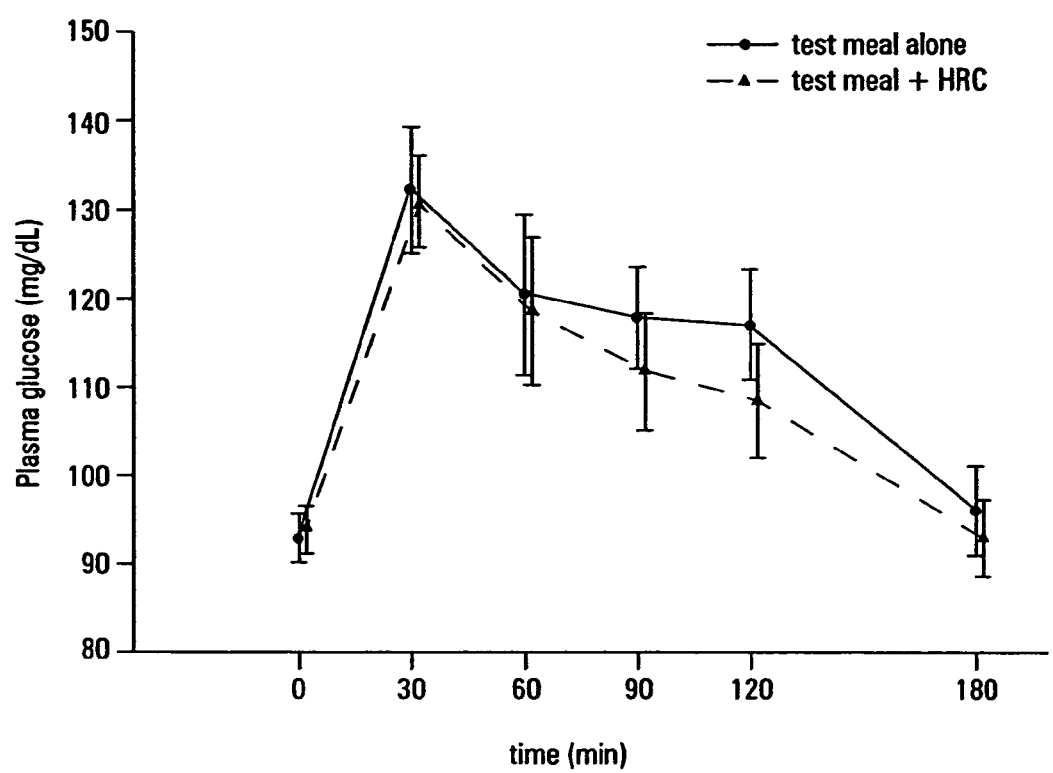
FIG. 3 demonstrates the mean plasma glucose concentrations in response to the baseline meal, not containing HRC (solid line) and after the meal with HRC (dashed line) during the acute postprandial study (n=33).

Mean fasting glucose concentration at baseline was within normal range as shown in Table 7, and was virtually identical after both test meals (P=0.43). Postprandial glucose concentration after each of the two test meals was similar (P=0.51) and peaked at 30 min (FIG. 3). There were no significant differences in the incremental or total area under the glucose curve (AUC and tAUC) between the meals, although there was a trend towards a decrease in both responses also shown in Table 7 (P=0.16 and P=0.22, respectively).

Figure 4A:
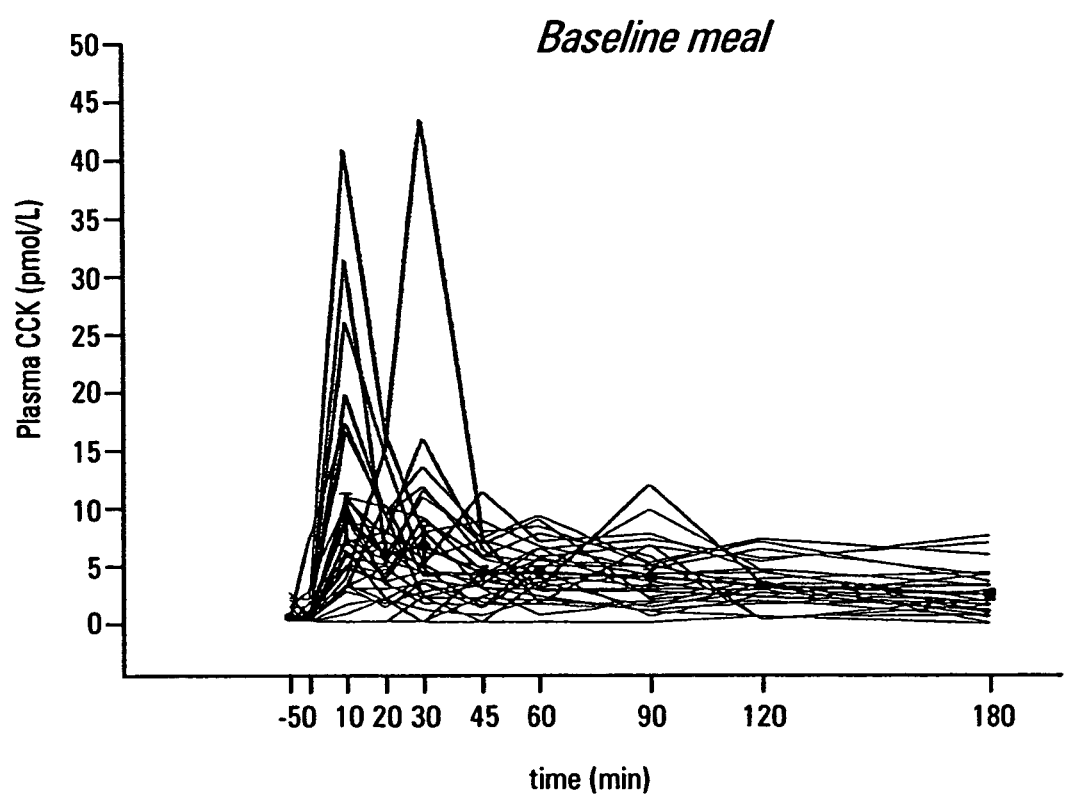
FIGS. 4A-B depict plasma cholecystokinin (CCK) concentrations after (A) baseline meal not containing HRC or (B) containing HRC consumed during the acute postprandial study. Thick line represents mean response (±SEM), while background lines show all 33 individual responses.
Figure 4B:
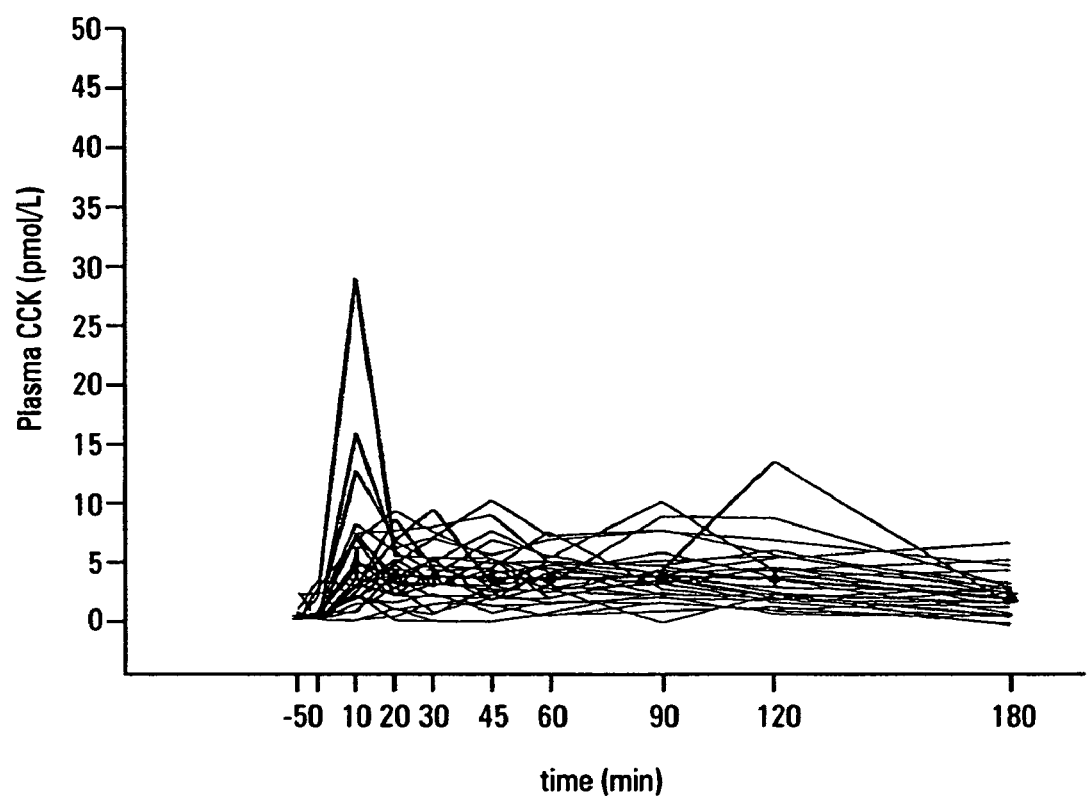
Figure 5A:
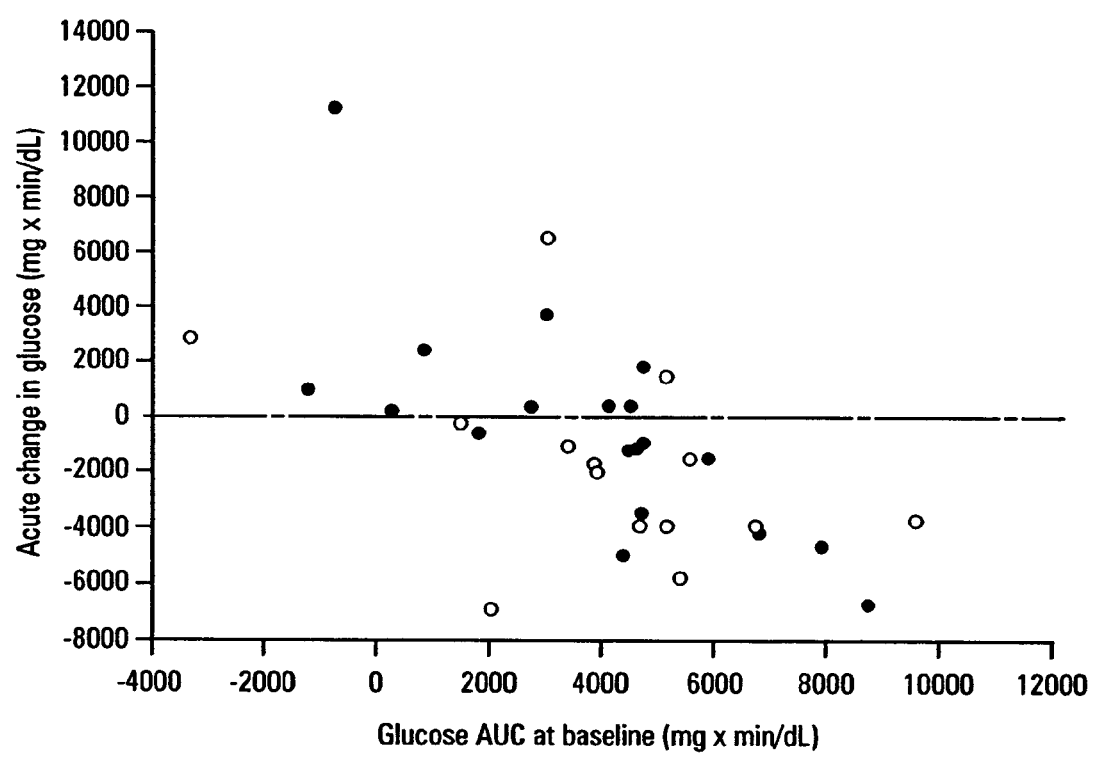
FIGS. 5A-B show change in AUC for glucose against baseline glucose AUC during the acute postprandial study for men (○) and women (●) (total n=33)(A); change in AUC for cholecystokinin (CCK) against baseline CCK AUC during the acute postprandial study for men (○) and women (●) (total n=33) is depicted in FIG. 5B.
Figure 5B:
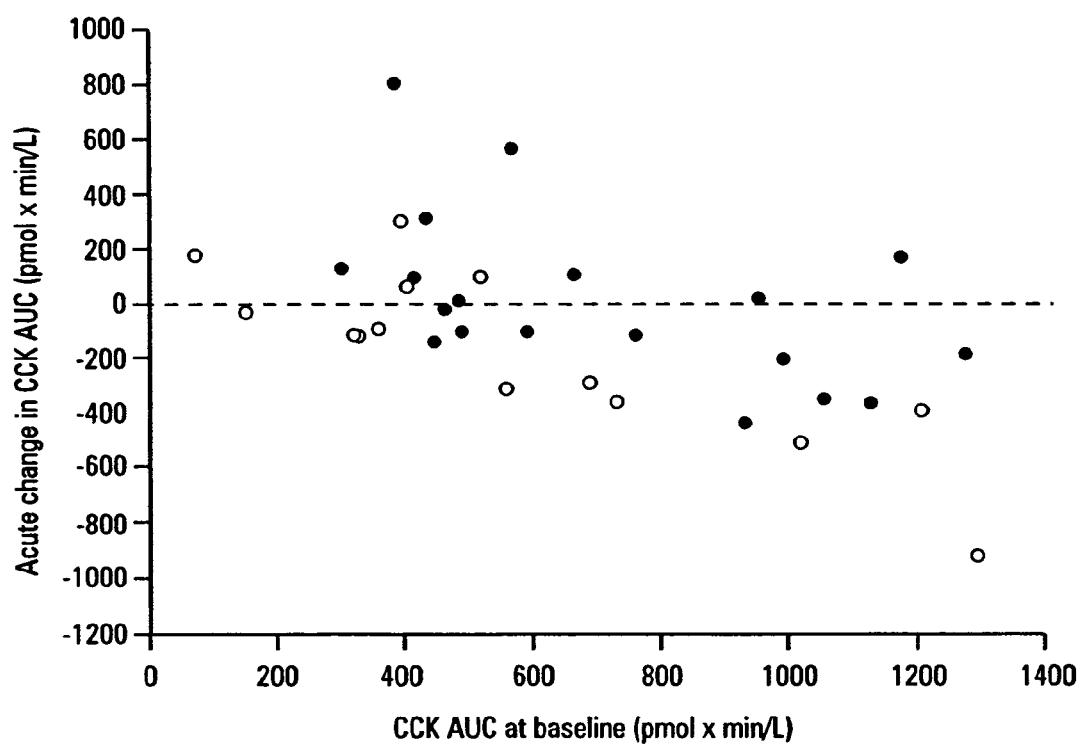

Both meals resulted in increases in CCK from very low fasting concentrations of about 0.5 pmol/L to a mean peak of 11.1 pmol/L after the baseline meal and 6.2 pmol/L after the fiber-containing meal. This decrease in mean peak CCK value was statistically significant (P=0.01). Additionally, these first CCK peaks occurred at 10 min after the first meal, but at 20 min after the fiber-containing second meal. However, this change was not significant (P=0.32). The average CCK concentration at 180 min was almost identical between the meals (P=0.64). The incremental CCK AUC and tAUC tended to be lower after the fiber-containing meal, but the decreases were not significant (P=0.19 and P=0.08, respectively) (FIGS. 4A-B). A correlation analysis showed that the change in glucose and CCK AUC responses was inversely related to baseline glucose and CCK AUCs, respectively (FIGS. 5A-B). The higher the baseline AUC response was, the greater the change in acute response appeared to be (Spearman's r=−0.613, P=0.001 for glucose and r=−0.581, P=0.0004 for CCK).

TABLE 7

Results from acute postprandial study (n = 33)[1]

| | Baseline meal test (no HRC[2]) | Meal test with HRC[2] | Change | P-value |
|---|---|---|---|---|
| Fasting plasma glucose | | | | |
| mmol/L | 5.2 ± 0.6 | 5.2 ± 0.7 | 0.05 ± 0.4 | 0.43 |
| mg/dL | 92.9 ± 11.1 | 93.8 ± 11.9 | 0.9 ± 6.6 | |
| Glucose AUC[3] | | | | |
| mmol · min/L | 220.0 ± 153.9 | 168.6 ± 167.5 | −51.4 ± 207.4 | 0.16 |
| mg · min/dL | 3,964 ± 2,773 | 3,037 ± 3,018 | −926.4 ± 3,736 | |
| Glucose tAUC[4] | | | | |
| mmol · min/L | 1,148 ± 189 | 1,106 ± 211 | −42.3 ± 195.6 | 0.22 |
| mg · min/dL | 20,682 ± 3,404 | 19,919 ± 3,797 | −762.7 ± 3,523 | |
| Glucose peak | | | | |
| mmol/L | 7.7 ± 1.8 | 7.6 ± 1.5 | −0.2 ± 1.4 | 0.51 |
| mg/dL | 139.3 ± 31.6 | 136.5 ± 27.9 | −2.9 ± 24.9 | |
| Time to glucose peak Min | 30 (30; 120)[5] | 30 (30; 60) | 0 (−60; 30) | 0.43 |
| Fasting plasma CCK pmol/L | 0.5 ± 0.7 | 0.4 ± 0.6 | −0.2 ± 0.9 | 0.33 |
| CCK AUC[3] pmol · min/L | 658.2 ± 337.2 | 584.6 ± 307.2 | −73.6 ± 318.7 | 0.19 |
| CCK tAUC[4] pmol · min/L | 756.2 ± 358.0 | 655.9 ± 312.3 | −100.6 ± 318.3 | 0.08 |
| CCK peak pmol/L | 11.1 ± 10.4 | 6.2 ± 5.3 | −4.9 ± 10.7* | 0.01 |
| Time to CCK peak Min | 10 (10; 90)[5] | 20 (10; 45) | 10 (−80; 35) | 0.32 |
| CCK at 180 min pmol/L | 2.6 ± 1.8 | 2.5 ± 1.6 | −0.15 ± 1.8 | 0.64 |

[1]Mean ± SD, unless otherwise noted.
[2]HRC = highly refined cellulose.
[3]AUC = area under the curve, adjusted for baseline.
[4]tAUC = total area under the curve.
[5]Median (range).
*Denotes a significant change at P ≦ 0.05.

Analysis of the data separately for men and women showed significant differences at baseline for a number of parameters (Table 8). Women had lower fasting glucose, compared to men (P=0.01), lower glucose peak concentration (P=0.01) and lower glucose tAUC (P=0.05). Additionally, men experienced significant within-group decreases in CCK AUC, CCK tAUC and CCK peak concentration. Moreover, there was a difference in the mean change in CCK peak concentration after each of the test meals between men and women; men experienced a significantly greater decrease than did women (P=0.05). Lastly, the mean time to CCK peak following both meals was 10 min in women, while for men it was 15 min at baseline (P=0.17) and 20 min after the fiber-containing meal (P=0.99).

Figure 6A:
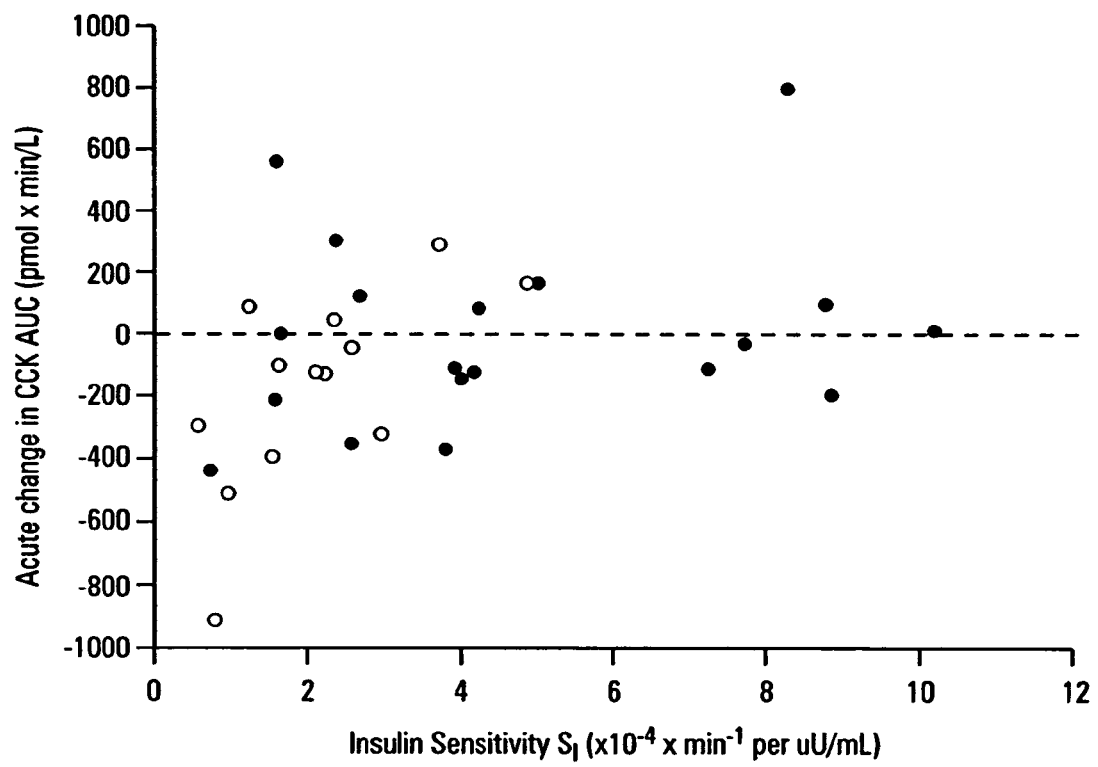
FIGS. 6A-B depict change in AUC for cholecystokinin (CCK)(A) and change in peak cholecystokinin concentration against baseline insulin sensitivity during the acute postprandial study for men (○) and women (●) (total n=33).
Figure 6B:
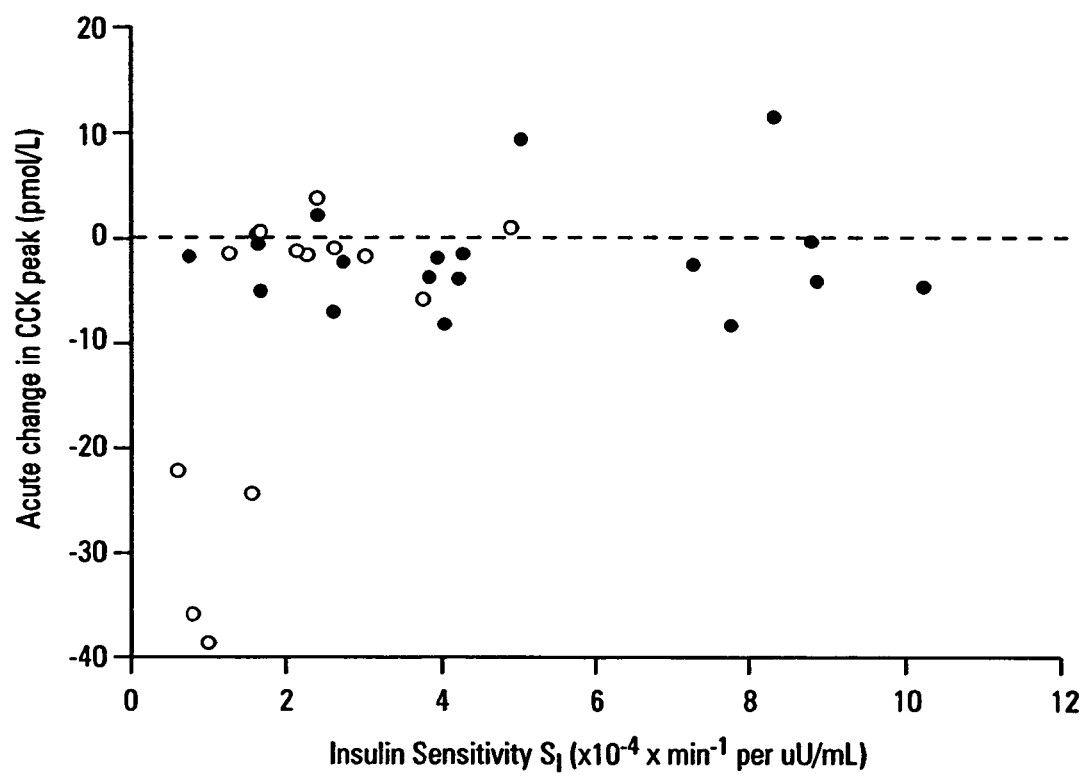

A correlation analysis showed significant inverse relationships between fasting insulin at baseline and the change in CCK AUC and CCK tAUC responses (Pearson's r=−0.396 and −0.508, P=0.02 and 0.003, respectively), as well as the mean acute change in CCK peak (r=−0.510, P=0.0003). Furthermore, insulin sensitivity at baseline was positively correlated with all three of the above parameters as shown in FIGS. 6A-B (r=0.371, 0.367, 0.355; P=0.04, 0.04, 0.05, for CCK AUC, CCK tAUC and CCK peak, respectively). Finally, BMI at baseline appeared to be inversely correlated with the mean change in CCK peak (−0.391, P=0.02).

TABLE 8

Sex differences in metabolic variables during acute postprandial study[1]

| | WOMEN (n = 19) | | | MEN (n = 14) | | | P-value for change |
|---|---|---|---|---|---|---|---|
| | Baseline meal test (no HRC[2]) | Meal test with HRC[2] | Change | Baseline meal test (no HRC) | Meal test with HRC | Change | |
| Fasting plasma glucose | | | | | | | |
| mmol/L | 4.9 ± 0.3* | 5.0 ± 0.4* | 0.1 ± 0.3 | 5.5 ± 0 7* | 5.5 ± 0.8* | −0.02 ± 0.5 | 0.38 |
| mg/dL | 87.9 ± 5.9* | 89.7 ± 6.6* | 1.8 ± 4.8 | 99.6 ± 13.0* | 99.4 ± 15.1* | −0.3 ± 8.5 | |
| Glucose AUC[3] | | | | | | | |
| mmol · min/L | 214 ± 151 | 193 ± 146 | −21.3 ± 215.3 | 228 ± 163 | 136 ± 194 | −92.3 ± 196.4 | 0.34 |
| mg · min/dL | 3,857 ± 2,723 | 3,474 ± 2,625 | −384 ± 3,879 | 4,108 ± 2,936 | 2,445 ± 3,497 | −1,663 ± 3,537 | |
| Glucose tAUC[4] | | | | | | | |
| mmol · min/L | 1,092 ± 167* | 1,089 ± 150 | −3.4 ± 190.5 | 1,224 ± 196* | 1,128 ± 150 | −95.2 ± 196.7 | 0.19 |
| mg · min/dL | 19,678 ± 3,014* | 19,617 ± 2,706 | −61.6 ± 3,432 | 22,044 ± 3,533* | 20,329 ± 5,004 | −1,714 ± 3,543 | |
| Glucose peak | | | | | | | |
| mmol/L | 7.0 ± 1.4** | 7.0 ± 1.1* | −0.07 ± 1.3 | 8.7 ± 1.8** | 8.4 ± 1.7* | −0.3 ± 1.5 | 0.67 |
| mg/dL | 126.7 ± 25.4** | 125.4 ± 19.3* | −1.3 ± 24.0 | 156.5 ± 31.9** | 151.4 ± 31.2* | −5.1 ± 26.7 | |

TABLE 8-continued

Sex differences in metabolic variables during acute postprandial study[1]

| | WOMEN (n = 19) | | | MEN (n = 14) | | | P-value for change |
|---|---|---|---|---|---|---|---|
| | Baseline meal test (no HRC[2]) | Meal test with HRC[2] | Change | Baseline meal test (no HRC) | Meal test with HRC | Change | |
| Time to glucose peak Min | 30 (30; 90)[5] | 30 (30; 60) | 0 (−60; 30) | 30 (30; 120) | 30 (30; 60) | 0 (−60; 30) | 0.29 |
| Fasting plasma CCK pmol/L | 0.5 ± 0.6 | 0.3 ± 0 5 | −0.1 ± 0.6 | 0.6 ± 0.8 | 0.5 ± 0.6 | −0.2 ± 1.1 | 0.93 |
| CCK AUC[3] pmol · min/L | 716 ± 307 | 722 ± 302** | 5.9 ± 306.5 | 580 ± 371 | 398 ± 203** | −182 ± 313[a] | 0.10 |
| CCK tAUC[4] pmol · min/L | 798 ± 302 | 779 ± 296* | −19.0 ± 301.8 | 699 ± 428 | 488 ± 256* | −211 ± 317[a] | 0.09 |
| CCK peak pmol/L | 9.3 ± 4.6 | 7.5 ± 6.4 | −1.8 ± 5.1 | 13.5 ± 15.0 | 4.4 ± 2.3 | −9.1 ± 14.6[a] | 0.09 |
| Time to CCK peak Min | 10 (10; 90)[5] | 10 (10; 45) | 0 (−80; 35) | 15 (10; 30) | 20 (10; 45) | 0 (−20; 25) | 0.99 |
| CCK at 180 min pmol/L | 3.0 ± 2.0 | 3.3 ± 1.5** | 0.2 ± 1.9 | 2.0 ± 1.4 | 1.4 ± 0.8** | −0.6 ± 1.6 | 0.17 |

[1]Mean ± SD, unless noted otherwise. Women and men were compared for differences at baseline, after acute test and in change.
[2]HRC = highly refined cellulose.
[3]AUC = area under the curve, adjusted for baseline.
[4]tAUC = total area under the curve.
[5]Median (range).
*Denotes a significant difference between groups at $P \leq 0.05$.
**Denotes a significant difference between groups at $P \leq 0.005$.
[a]Denotes a significant within-group difference at $P \leq 0.05$.

Long-Term Study of Adaptive Changes

Figure 7A:
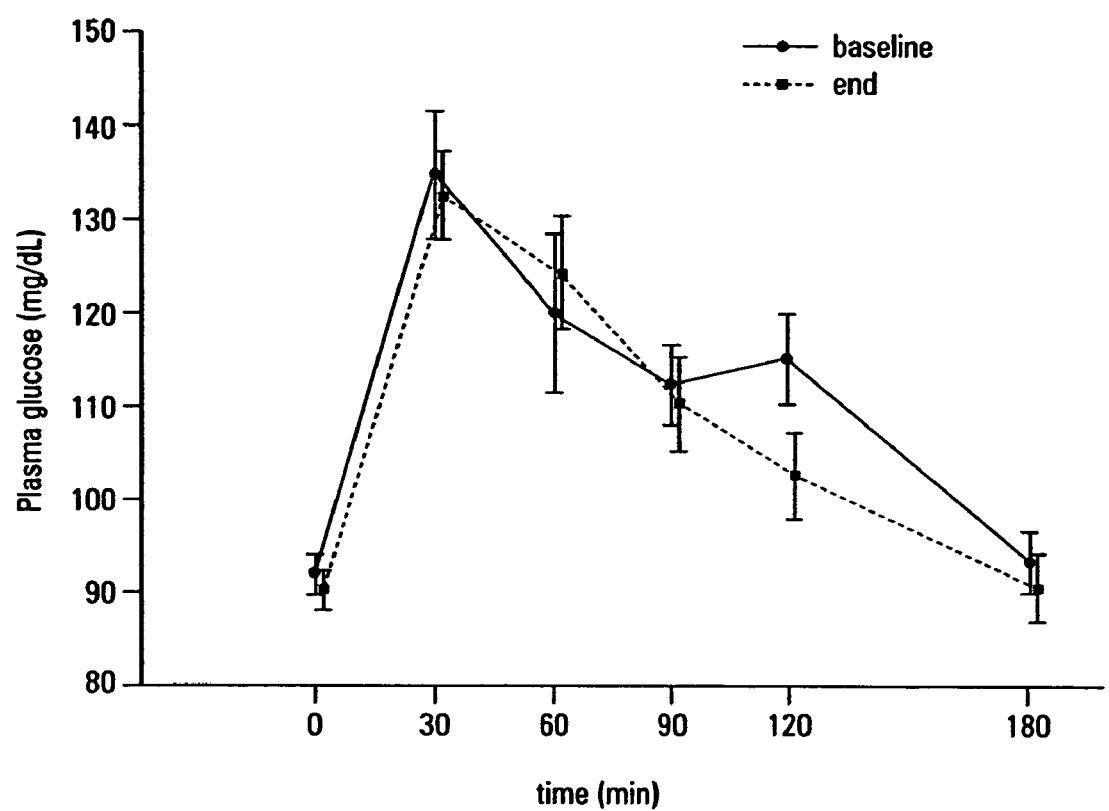
FIGS. 7A-B depict plasma glucose concentrations in the (A) actively treated (HRC) group (n=16) and (B) control group (n=16) after baseline test meal and after final meal, following the 6-week intervention.
Figure 7B:
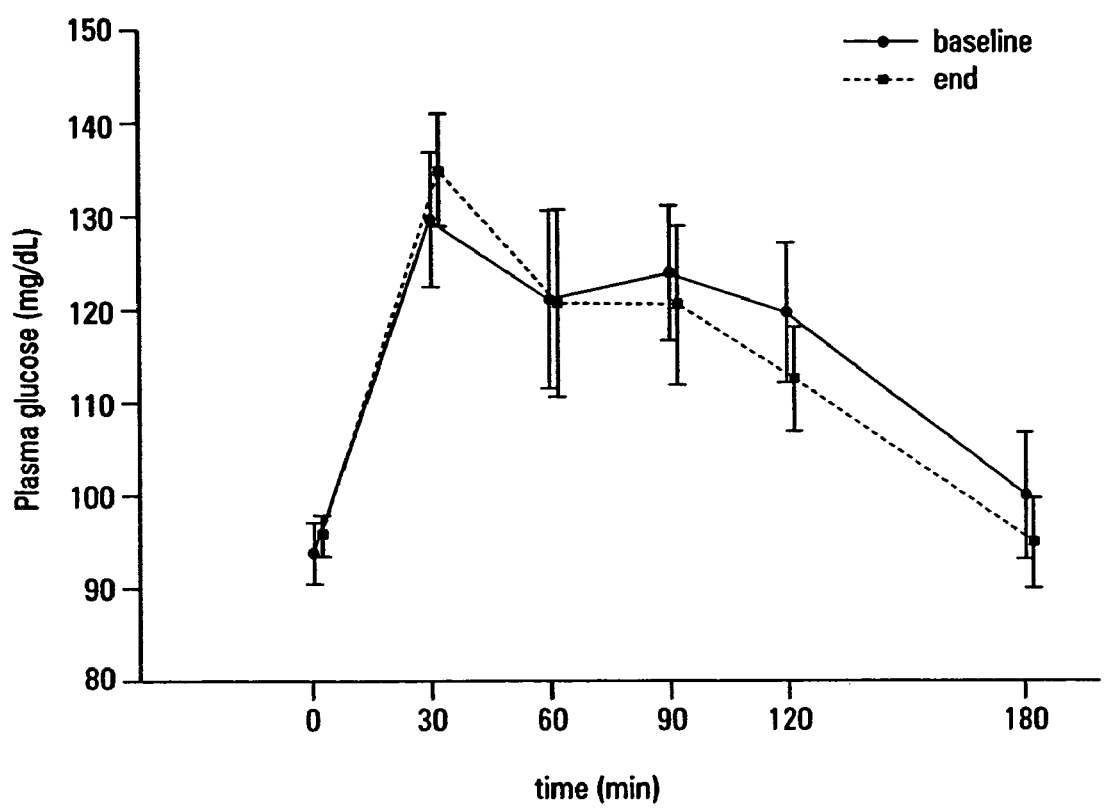

The two groups were comparable with regards to all metabolic variables at baseline as Table 9 demonstrates. Mean fasting insulin concentrations remained unchanged after the 6-week intervention in both groups (P=0.42). The average fasting plasma glucose concentration tended to decrease in the HRC group, while increasing in the control group, but the difference in change between the groups did not reach significance (P=0.13). Glucose values in both groups peaked at 30 min on the average both at baseline (P=0.09 for between-group difference) and at the end of intervention (P=0.18 for difference in change) (FIGS. 7A-B). There was also no change in the mean glucose peak in either of the groups (P=0.75). Glucose AUC and tAUC decreased slightly in both groups, resulting in a change that was not different between the groups.

The mean fasting CCK concentration at baseline was notably higher in the HRC group than in the control group (P=0.09). There were no significant differences in the changes from baseline to end between the groups for any of the CCK parameters as shown in Table 9.

TABLE 9

Metabolic variables at baseline and end of long-term study[1][2]

| | HR CELLULOSE GROUP (n = 16) | | | CONTROL GROUP (n = 16) | | | P-value for change |
|---|---|---|---|---|---|---|---|
| | Baseline | End | Change | Baseline | End | Change | |
| Fasting plasma insulin | | | | | | | |
| pmol/L | 77 1 ± 44.3 | 85 8 ± 50.4 | 8.9 ± 38.3 | 61.8 ± 39.0 | 61.9 ± 38.1 | −0.2 ± 22.9 | 0 42 |
| μU/mL | 12 8 ± 7.4 | 14 3 ± 8.4 | 1 5 ± 6.4 | 10 3 ± 6.5 | 10.3 ± 6.3 | −0.04 ± 3.8 | |
| Fasting plasma glucose | | | | | | | |
| mmol/L | 5.1 ± 0.5 | 5.0 ± 0.5 | −0.1 ± 0.3 | 5.2 ± 0.7 | 5.3 ± 0.5 | 0.1 ± 0.5 | 0 13 |
| mg/dL | 92.7 ± 9.1 | 90.4 ± 8.8 | −2.3 ± 5.7 | 93.8 ± 13 1 | 95.7 ± 8.8 | 1.9 ± 9.4 | |
| Glucose AUC[3] | | | | | | | |
| mmol · min/L | 204.1 ± 163.2 | 189.7 ± 131.4 | −14.3 ± 137.6 | 230.7 ± 151.8 | 189.1 ± 161.0 | −41.6 ± 171.9 | 0.62 |
| mg min/dL | 3,676 ± 2,940 | 3,418 ± 2,367 | −258 ± 2,480 | 4,156 ± 2,735 | 3,406 ± 2,900 | −750 ± 3,097 | |
| Glucose tAUC[4] | | | | | | | |
| mmol · min/L | 1,130 ± 176 | 1,093 ± 111 | −37.4 ± 151.2 | 1,167 ± 211 | 1,145 ± 198 | −22.3 ± 183.4 | 0.80 |
| mg min/dL | 20,360 ± 3,171 | 19,686 ± 2,008 | −674.1 ± 2,724 | 21,031 ± 3,796 | 20,630 ± 3,562 | −401.3 ± 3,304 | |

TABLE 9-continued

Metabolic variables at baseline and end of long-term study[1][2]

| | HR CELLULOSE GROUP (n = 16) | | | CONTROL GROUP (n = 16) | | | P-value |
|---|---|---|---|---|---|---|---|
| | Baseline | End | Change | Baseline | End | Change | for change |
| Glucose peak | | | | | | | |
| mmol/L | 7.7 ± 1.6 | 7.7 ± 1.1 | −0.03 ± 1.4 | 7.8 ± 2.0 | 7.9 ± 1.6 | 0.1 ± 1.6 | 0.75 |
| mg/dL | 139 0 ± 29.5 | 138.5 ± 19 0 | −0.5 ± 24.7 | 140 6 ± 35.3 | 143.1 ± 28.9 | 2.5 ± 28.3 | |
| Time to glucose peak Min | 30 (30; 60)[5] | 30 (30, 90) | 0 (−30; 60) | 30 (30; 120) | 30 (30; 90) | 0 (−60; 30) | 0.18 |
| Fasting plasma CCK Pmol/L | 0.8 ± 0.8 | 0.7 ± 0.9 | −0.04 ± 1.1 | 0.3 ± 0.5 | 0.6 ± 0.8 | 0.2 ± 0.9 | 0.47 |
| CCK AUC[3] Pmol · min/L | 677.0 ± 336.7 | 684.1 ± 336.4 | 7.1 ± 353.6 | 654.7 ± 353.3 | 625.6 ± 372.2 | −29.1 ± 298.9 | 0.76 |
| CCK tAUC[4] Pmol · min/L | 817.3 ± 359 4 | 814.1 ± 378 5 | −3.2 ± 277.6 | 714.9 ± 362.9 | 729.7 ± 354.7 | 14.9 ± 271.7 | 0.85 |
| CCK peak Pmol/L | 10.6 ± 10.4 | 9.3 ± 5.1 | −1.3 ± 10.0 | 12.1 ± 10.8 | 12.2 ± 11.3 | 0.2 ± 14.1 | 0.74 |
| Time to CCK peak Min | 10 (10; 90)[4] | 10 (10; 45) | 0 (−80, 35) | 10 (10; 30) | 10 (10; 60) | 0 (−20; 50) | 0.75 |
| CCK at 180 min Pmol/L | 2.9 ± 1.9 | 3.4 ± 2.1 | 0 5 ± 2.1 | 2 4 ± 1.8 | 2.4 ± 1.6 | 0.1 ± 1.8 | 0.50 |

[1]Mean ± SD, unless noted otherwise.
[2]No significant differences between groups at $P \leq 0.05$.
[3]AUC = area under the curve, adjusted for baseline.
[4]tAUC = total area under the curve.
[5]Median (range).

Figure 8A:
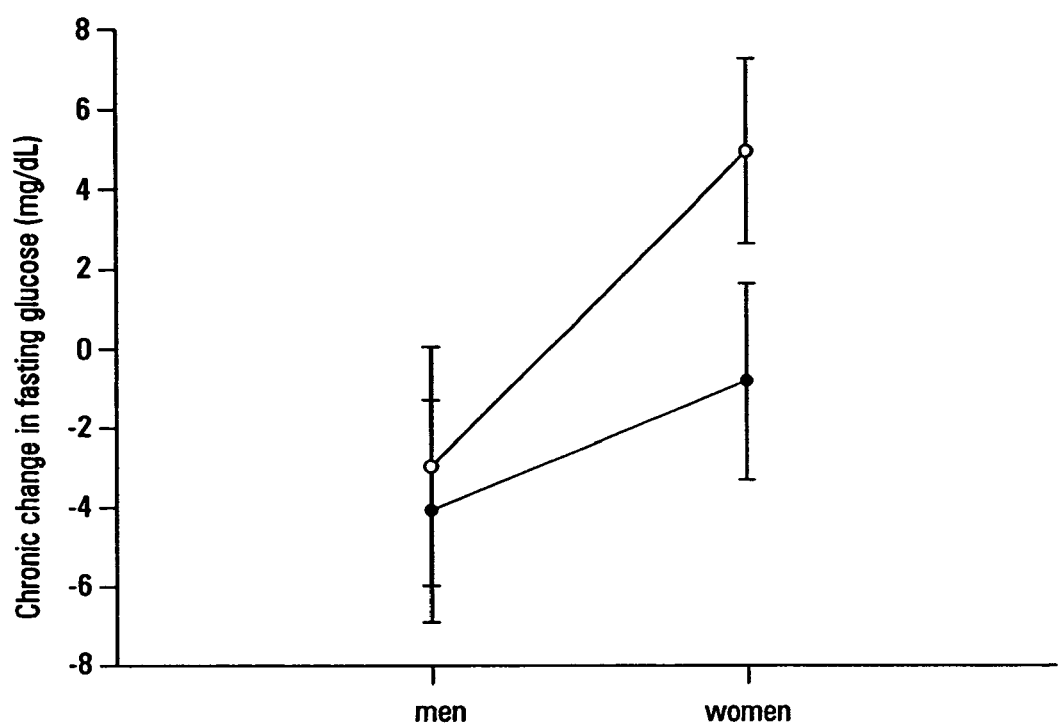
FIG. 8A shows mean fasting plasma glucose concentrations (±SEM) for men and women in the actively treated (HRC) group (●) and the control group (○) following fiber-free test meals at baseline and after 6 weeks of intervention (P-value for main effect of gender=0.038)(A).
Figure 8B:
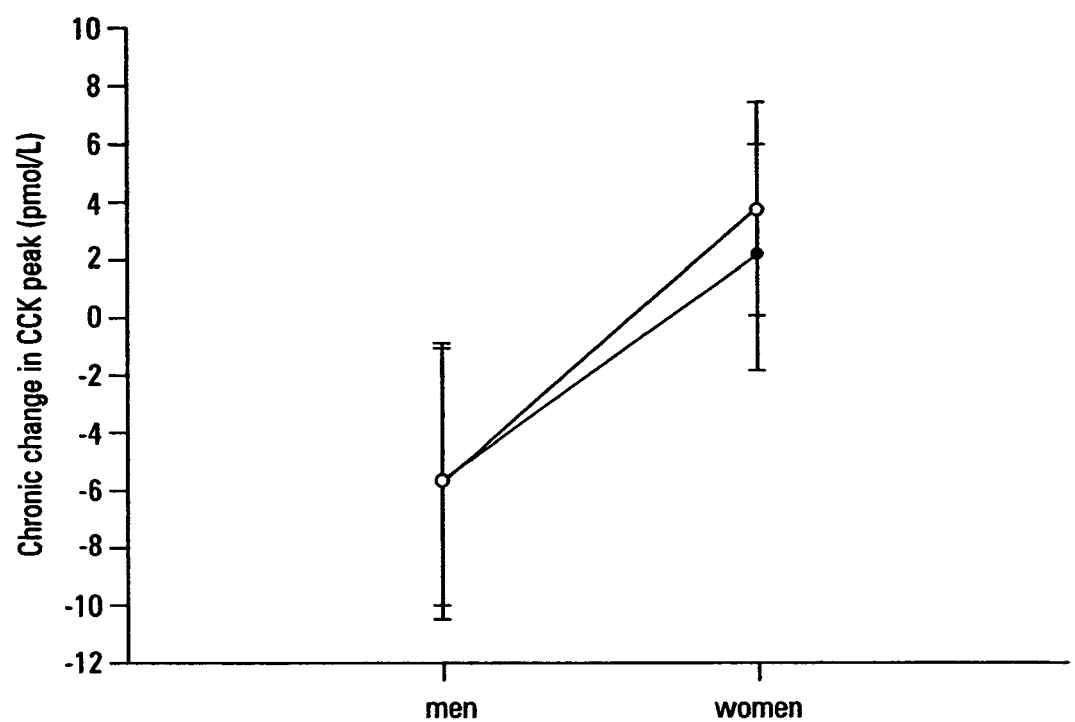
FIG. 8B shows mean plasma cholecystokinin (CCK) peak concentrations (±SEM) for men and women in the actively treated (HRC) group (●) and the control group (○) following fiber-free test meals at baseline and after 6 weeks of intervention (P-value for main effect of gender=0.052).

Because there were no significant differences between treatment groups, a comparison between the long-term responses were made by gender (Table 10). As in the acute postprandial comparisons, there were gender differences at baseline as well as significant main gender effects after intervention. Men experienced greater reductions in both fasting glucose and peak CCK concentrations compared to women as shown in FIGS. 8A-B (P=0.038 and P=0.052, respectively). At baseline, women had a significantly lower mean fasting plasma glucose concentration (P=0.003), glucose tAUC response (P=0.04) and average glucose peak value (P=0.003). Furthermore, after the 6-week intervention, the fasting plasma glucose concentration in men decreased significantly, compared to a slight increase in women (P=0.04). The average CCK peak in men also decreased significantly, while an increase was observed in women (P=0.04). When comparing men and women further by treatment, these differences were no longer significant, but the same trend was evident. The nine women in the HRC group experienced an average decrease in fasting glucose of only 0.9 mg/dL, while the reduction in the seven men receiving treatment was 4.1 mg/dL (P=0.3). Similarly, the seven men showed a drop of 5.6 pmol/L in CCK peak after intervention, while the nine women experienced a 2 pmol/L increase in CCK peak (P=0.13). An identical trend was apparent for the 6-week change in glucose peak (−10 mg/dL for men, 7 mg/dL for women, P=0.18) and the change in mean CCK tAUC response (−135 pmol·min/L for men, 99 pmol·min/L for women, P=0.09). Adjusting variable changes for fasting insulin concentration and insulin sensitivity at baseline did not change any of the conclusions.

TABLE 10

Sex differences in metabolic variables at baseline and end of long-term study[1]

| | WOMEN (n = 19) | | | MEN (n = 13) | | | P-value |
|---|---|---|---|---|---|---|---|
| | Baseline | End | Change | Baseline | End | Change | for change |
| Fasting plasma insulin | | | | | | | |
| pmol/L | 59.6 ± 33.7 | 57.6 ± 28 3* | −2.0 ± 27.9 | 84.2 ± 49.0 | 97.8 ± 55.7* | 13.7 ± 34.9 | 0.17 |
| µU/mL | 9.9 ± 5.6 | 9.6 ± 4.7* | −0.3 ± 4.7 | 14.0 ± 8.2 | 16.3 ± 9.3* | 2.3 ± 5.8 | |
| Fasting plasma glucose | | | | | | | |
| mmol/L | 4.9 ± 0.3** | 5.0 ± 0.4* | 0.1 ± 0.4* | 5.6 ± 0.7** | 5.4 ± 0.5* | −0.2 ± 0.4 | 0.04 |
| mg/dL | 87.9 ± 5.9** | 90.1 ± 8.0* | 2.2 ± 7.9* | 101.0 ± 12.5** | 97.4 ± 9.0* | −3.6 ± 6.8 | |
| Glucose AUC[2] | | | | | | | |
| mmol min/L | 214 ± 151 | 170 ± 118 | −44 3 ± 145.6 | 222 ± 168 | 218 ± 177 | −4.1 ± 168.2 | 0.48 |
| mg min/dL | 3,857 ± 2,723 | 3,059 ± 2,131 | −798 ± 2,623 | 4,002 ± 3,028 | 3,928 ± 3,196 | −73.8 ± 3,030 | |
| Glucose tAUC[3] | | | | | | | |
| mmol min/L | 1,092 ± 167* | 1,070 ± 107* | −22.7 ± 161.6 | 1,231 ± 202* | 1,191 ± 199* | 40.2 ± 177.2 | 0.77 |
| mg · min/dL | 19,678 ± 3,014* | 19,269 ± 1,933* | −410 ± 2,911 | 22,182 ± 3,638* | 21,457 ± 3,579* | −724.6 ± 3,193 | |
| Glucose peak | | | | | | | |
| mmol/L | 7.0 ± 1.4** | 7.2 ± 1.1** | 0 2 ± 1.4 | 8.8 ± 1.8** | 8.7 ± 1.2** | −0.1 ± 1 5 | 0.53 |
| mg/dL | 126.7 ± 25.4** | 130.2 ± 19.4** | 3.5 ± 25.8 | 158.9 ± 31.8** | 156.3 ± 22.5** | −2.6 ± 27.4 | |

TABLE 10-continued

Sex differences in metabolic variables at baseline and end of long-term study[1]

| | WOMEN (n = 19) | | | MEN (n = 13) | | | P-value |
|---|---|---|---|---|---|---|---|
| | Baseline | End | Change | Baseline | End | Change | for change |
| Time to glucose peak Min | 30 (30; 90)[4] | 30 (30; 90) | 0 (−60; 60) | 30 (30; 120) | 30 (30; 90) | 0 (−30; 30) | 0 58 |
| Fasting plasma CCK pmol/L | 0.5 ± 0 6 | 0.7 ± 0.8 | 0 2 ± 0.9 | 0 7 ± 0.8 | 0.6 ± 1.0 | −0.07 ± 1.2 | 0.45 |
| CCK AUC[2] pmol min/L | 716 ± 307 | 747 ± 363 | 31.4 ± 338.6 | 593 ± 383 | 520 ± 293 | −73.0 ± 300.0 | 0.38 |
| CCK tAUC[3] pmol min/L | 798 ± 302 | 867 ± 326 | 68.2 ± 301.0 | 719 ± 438 | 633 ± 384 | −85.4 ± 194.3 | 0.12 |
| CCK peak pmol/L | 9.3 ± 4.6 | 12 2 ± 10.3 | 2.9 ± 10.4 | 14 3 ± 15.4 | 8.6 ± 5.6 | −5.7 ± 12.8 | 0.04 |
| Time to CCK peak Min | 10 (10; 90)[4] | 10 (10, 60) | 0 (−80; 50) | 10 (10; 30) | 10 (10; 45) | 0 (−20; 35) | 0.14 |
| CCK value at 180 min pmol/L | 3.0 ± 2 0 | 3.4 ± 1 6 | 0.4 ± 2.3 | 2.1 ± 1.5 | 2.3 ± 2.2 | 0.2 ± 1.4 | 0.81 |

[1]Mean ± SD, unless noted otherwise Baseline values for women are the same as in Table 4-4; baseline values for men differ from Table 4-4 because of the exclusion of one individual who did not complete the study.
[2]AUC = area under the curve, adjusted for baseline.
[3]tAUC = total area under the curve.
[4]Median (range).
*Denotes a significant difference between groups at P ≦ 0.05
**Denotes a significant difference between groups at P ≦ 0.005

Side Effects

The side effects are reported in Example I, above.

Discussion

In the acute postprandial study, the glucose and CCK responses of hypercholesterolemic subjects to two liquid mixed meals, one of which contained HRC and the other did not, were compared. Additionally, responses to HRC fiber-free test meals were compared before and after a 6-week intervention with HRC in the same individuals. No significant effects of HRC on postprandial glucose and CCK responses were found either acutely, or after a long-term adaptation to the fiber. However, an acute exposure to HRC tended to decrease both glucose and CCK AUC responses, while significantly decreasing the mean CCK peak concentration. Long-term exposure to HRC had no effect on these parameters, except for a small but insignificant reduction of the mean fasting glucose concentration.

While not wishing to be bound by theory, it is believed that the lack of significant long-term effect of the fiber on glucose tolerance CCK release may be related to pancreatic and mucosal adaptation. It has been shown that the activity of pancreatic and intestinal enzymes adapts to the nutrient composition of the diet (Reiser and Lewis, Prog. Biochem. Pharmacol., 21, 135 (1986)). A non-limiting belief is that as the availability of carbohydrates for digestion decreases because they are trapped within the numerous inter-fiber spaces of HRC, pancreatic amylase activity may gradually increase to compensate for a potentially reduced absorption, leading to unchanged plasma glucose concentrations.

On the other hand, the findings of decreased cholecystokinin response with the fiber-containing test meal may suggest an effect of HRC on CCK similar to that of soluble fibers on gastric inhibitory polypeptide (GIP) (Reiser and Lewis, Prog. Biochem. Pharmacol., 21, 135 (1986)). GIP stimulates insulin release (Marks and Turner, Essays Biochem., 3, 109 (1977)) and there is evidence of CCK's involvement in the amino-acid induced secretion of insulin. Thus, decreases in the concentrations of these enterogastrones by HRC would result in lower insulin release, once again resulting in unchanged plasma glucose levels.

Additionally, pancreatic enzyme secretion in response to digestive products requires CCK to stimulate the enzyme's extracellular release from zymogen granules in the cytosol, by enhancing plasma membrane permeability. While not wishing to be bound by theory, this may suggest that when the absorption of digestive products is delayed, less CCK is needed at any given time. Thus, CCK postprandial concentration is decreased, while it may continue to be secreted in small amounts for an extended period of time. The combination of these changes might result in unchanged overall glucose and CCK area under the curve responses.

The findings indicate that HRC decreases the postprandial CCK peak following a HRC-containing meal and that it might have an acute effect on postprandial glucose and CCK responses.

Subjects in the present study were not diabetic, however, data from the larger study, part of which is reported here, indicated that individuals in the HRC group had significantly lower insulin sensitivity and significantly higher acute insulin response to glucose, compared to individuals in the control group. This indicates that subjects in the HRC group were more insulin resistant and had a poorer 13-cell function. This may have confounded the ability to detect a significant effect of long-term HRC intake on both glucose and CCK postprandial responses. Results from the correlation analysis, showing an inverse association between several CCK parameters and fasting insulin, as well as a positive association between the same parameters and insulin sensitivity at baseline further support such a conclusion. Insulin resistant individuals presenting with high fasting insulin concentrations and low insulin sensitivity exhibited lower change in mean CCK AUC, tAUC and peak in response to the fiber-containing meal.

Example IV

Sugar Binding with HRC

The present study evaluated the binding of sugar to the HRC in dispersion. A sugar solution, as described below, was mixed with the HRC. The dispersion was then filtered to separate the sugar from the HRC, and the concentration of the separated sugar solution was then measured. A determination of the amount of sugar bound by the HRC was then made.

In the present example, dextrose (glucose) was used as the sugar. The concentration of the dextrose solutions was measured using a sugar analyzer known under the trade designator of ValuPack glucose analyzer. The present example used a sugar solution having a concentration of 100 g of sugar (e.g., dextrose) per 567.5 g (20 oz) water (a 17.62% sugar sol'n). Various concentrations of HRC were added to the dextrose solution to create a 1.057% HRC solution (e.g., 5 g HRC per 567.5 g (20 oz) of dextrose solution). The HRC used in the present example was obtained from citrus pulp, beet pulp, and corn stover as the raw starting material.

The HRC dextrose solution was homogenized and filtered with 4 micron filter paper under gravity for 30 minutes. The resulting samples of HRC were then diluted to make a diluted one hundred times (by volume) diluted dispersion of the HRC dextrose solution. The sugar content of the diluted filtrate was then analyzed using the Value Pack glucose test kit. The results are as shown in Table 10.

TABLE 10

| Test Raw material | % Fiber | Sugar concentrations Prior to co-processing | Sugar concentrations After co-processing | concentration reduction | sugar available per 20 oz drink (g) |
|---|---|---|---|---|---|
| 1) corn stover | 1.057 | 0% | <0.25% | 0% | 0 |
| 2) corn stover | 1.057 | 17.62% | 14.47% | 17.88% | 82.12 |
| 3) beet pulp | 1.057 | 17.62% | 14.81% | 15.96% | 84.04 |
| 4) Citrus pulp | 1.057 | 17.62% | 14.59% | 17.19% | 82.81 |
| 5) Citrus pulp | 1.057 | 0% | <0.25% | 0.00% | 0 |
| 6) citrus pulp (mixed w/ sugar but not co-processed) | 1.057 | 17.62% | 16.67% | 5.41% | 94.59 |
| 7) Dextrose w/ water | 1.057 | 17.62% | 17.51% | 0.64% | 99.36 |

Theoretical sugar amount=17.62%

The concentration reduction in the last column indicates that from a 20 oz beverage containing 17.62% sugar and no fiber, which is similar to a sports drink concentrate, 100 g of sugar would be available for a rapid absorption. Tests 1 and 5 were done to determine if the fibers themselves contributed sugar at all, but no significant amount of sugar could be detected.

In Test 6, the fiber and sugar were mixed together in the same way as all tests were done, but the sugar concentration was measured prior to the sample being dispersed and homogenized together. The result from Test 6 would indicate that the fiber addition alone makes a 5.4% reduction in sugar concentration, but when processed there is a much greater reduction in concentration (17.2%). Hence, the high shear mixing in the process is an important factor to incorporate the sugar in with our fiber and/or when the fiber is opened up by going through the process it is able to bind glucose more effectively. While not wishing to be bound by theory, it is believed that the HRC fiber has more affinity for dextrose and the dextrose is better incorporated into the fiber when going through the homogenization process. However, this question could possibly be answered by drying processed materials followed by mixing them with sugar and measuring the sugar concentration.

Based on this data, the HRC when processed with the sugar binds the sugar in the solution, which results in a 17.88% reduction in sugar concentration with corn stover as the starting raw material. A non-limiting theory is that the binding capacity of the HRC fiber is likely one of the reasons why a blood glucose reduction/flattening observation is made when the subjects consumed a beverage containing HRC at the same percentages listed above. The viscosity of the materials in the GI could likely be another mechanism.

The complete disclosures of the patents, patent documents, and publications cited herein are incorporated by reference in their entirety as if each were individually incorporated. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method, comprising:
   administering to a mammal an amount of a highly refined cellulose (HRC) effective to change at least one risk factor value for diabetes in the mammal, wherein the HRC is substantially indigestible and comprises a water retention capacity of greater than about 10 grams of water per gram of dry HRC, and wherein the amount of HRC comprises at least two grams dry weight of HRC per 1000 kilocalories consumed daily.

2. The method of claim 1, wherein the HRC comprises no less than about 0.1 percent lignin by dry weight of HRC.

3. The method of claim 1, wherein the amount of HRC effective to change at least one risk factor is an amount effective to increase insulin sensitivity ($S_I$) of the mammal.

4. The method of claim 1, wherein the amount of HRC effective to change at least one risk factor is an amount effective to increase acute insulin response to glucose (AIRg) of the mammal.

5. The method of claim 1, wherein the amount of HRC effective to change at least one risk factor is an amount effective to increase a disposal index of the mammal.

6. The method of claim 5, wherein the amount effective to increase a disposal index is an amount effective to change an AIRg value, an insulin sensitivity value, or a combination thereof, of the mammal.

7. The method of claim 1, wherein administering the effective amount of the HRC comprises administering at least about 5 grams of HRC within about a 24 hour interval to the mammal.

8. The method of claim 1, wherein administering further comprises administering the effective amount of HRC within about 30 minutes postprandially to the mammal.

9. A method, comprising:
   administering to a mammal an amount of an HRC effective to increase insulin sensitivity of the mammal, wherein the HRC is substantially indigestible and comprises a water retention capacity of greater than about 10 grams of water per gram of dry HRC, and wherein the amount of HRC comprises at least two grams dry weight of HRC per 1000 kilocalories consumed daily.

10. The method of claim 9, wherein the HRC comprises no less than about 0.1 percent lignin by dry weight of HRC.

11. The method of claim 9, wherein administering the effective amount of the HRC comprises administering at least about 5 grams of HRC within about a 24 hour interval to a mammal.

12. The method of claim 9, wherein administering further comprises administering the effective amount of HRC within about 30 minutes postprandially to the mammal.

13. A method, comprising:
administering to a mammal an amount of an HRC effective to increase a disposal index of the mammal, wherein the HRC is substantially indigestible and comprises a water retention capacity of greater than about 10 grams of water per to gram of dry HRC, and wherein the amount of HRC comprises at least two grams dry weight of HRC per 1000 kilocalories consumed daily.

14. The method of claim 13, wherein the amount effective to increase a disposal index is an amount effective to change an AIRg value, an insulin sensitivity value, or a combination thereof, of the mammal.

15. The method of claim 13, wherein administering the effective amount of the HRC comprises administering at least about 5 grams of HRC within about a 24 hour interval to a mammal.

16. A method, comprising:
administering to a mammal an amount of a highly refined cellulose (HRC) effective to change at least one risk factor value for diabetes in the mammal, wherein the HRC is substantially indigestible and comprises a water retention capacity of greater than about 10 grams of water per gram of dry HRC, and wherein administering further comprises administering the effective amount of HRC within about 30 minutes postprandially to the mammal.

17. The method of claim 16, wherein the HRC comprises no less than about 0.1 percent lignin by dry weight of HRC.

18. The method of claim 16, wherein the amount of HRC effective to change at least one risk factor is an amount effective to increase insulin sensitivity ($S_I$) of the mammal.

19. The method of claim 16, wherein the amount of HRC effective to change at least one risk factor is an amount effective to increase acute insulin response to glucose (AIRg) of the mammal.

20. The method of claim 16, wherein the amount of HRC effective to change at least one risk factor is an amount effective to increase a disposal index of the mammal.

21. The method of claim 20, wherein the amount effective to increase a disposal index is an amount effective to change an AIRg value, an insulin sensitivity value, or a combination thereof, of the mammal.

22. The method of claim 16, wherein administering the effective amount of the HRC comprises administering at least about 5 grams of HRC within about a 24 hour interval to the mammal.

23. A method, comprising:
administering to a mammal an amount of an HRC effective to increase insulin sensitivity of the mammal, wherein the HRC is substantially indigestible and comprises a water retention capacity of greater than about 10 grams of water per gram of dry HRC, and wherein administering further comprises administering the effective amount of HRC within about 30 minutes postprandially to the mammal.

24. The method of claim 23, wherein the HRC comprises no less than about 0.1 percent lignin by dry weight of HRC.

25. The method of claim 23, wherein administering the effective amount of the HRC comprises administering at least about 5 grams of HRC within about a 24 hour interval to a mammal.

26. A method, comprising:
administering to a mammal an amount of an HRC effective to increase a disposal index of the mammal, wherein the HRC is substantially indigestible and comprises a water retention capacity of greater than about 10 grams of water per to gram of dry HRC, and wherein administering further comprises administering the effective amount of HRC within about 30 minutes postprandially to the mammal.

27. The method of claim 26, wherein the amount effective to increase a disposal index is an amount effective to change an AIRg value, an insulin sensitivity value, or a combination thereof, of the mammal.

28. The method of claim 26, wherein administering the effective amount of the HRC comprises administering at least about 5 grams of HRC within about a 24 hour interval to a mammal.

* * * * *

UNITED STATES PATENT AND TRADEMARK OFFICE
CERTIFICATE OF CORRECTION

| | | |
|---|---|---|
| PATENT NO. | : 8,026,226 B2 | Page 1 of 1 |
| APPLICATION NO. | : 10/270475 | |
| DATED | : September 27, 2011 | |
| INVENTOR(S) | : Addis et al. | |

It is certified that error appears in the above-identified patent and that said Letters Patent is hereby corrected as shown below:

Column 1, Line 14

Delete "The U.S. Government may have certain rights in this invention."
And insert --The U.S. Government has certain rights in this invention.--

Signed and Sealed this
Twenty-second Day of November, 2011

David J. Kappos
*Director of the United States Patent and Trademark Office*